US009765343B2

(12) United States Patent
Godiska et al.

(10) Patent No.: US 9,765,343 B2
(45) Date of Patent: *Sep. 19, 2017

(54) LINEAR VECTORS, HOST CELLS AND CLONING METHODS

(71) Applicant: Lucigen Corporation, Middleton, WI (US)

(72) Inventors: Ronald Godiska, Mt. Horeb, WI (US); David A. Mead, Middleton, WI (US); Nikolai V. Ravin, Moscow (RU)

(73) Assignee: LUCIGEN CORPORATION, Middleton, WI (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/681,591

(22) Filed: Apr. 8, 2015

(65) Prior Publication Data

US 2015/0218565 A1 Aug. 6, 2015

Related U.S. Application Data

(63) Continuation of application No. 12/159,956, filed as application No. PCT/US2007/060500 on Jan. 12, 2007, now Pat. No. 9,029,134.

(60) Provisional application No. 60/747,733, filed on May 19, 2006, provisional application No. 60/758,479, filed on Jan. 12, 2006.

(51) Int. Cl.
| | |
|---|---|
| *C12N 15/70* | (2006.01) |
| *C12N 15/74* | (2006.01) |
| *C12N 15/73* | (2006.01) |
| *C12N 9/90* | (2006.01) |
| *C12P 19/34* | (2006.01) |

(52) U.S. Cl.
CPC .............. *C12N 15/73* (2013.01); *C12N 9/90* (2013.01); *C12N 15/70* (2013.01); *C12P 19/34* (2013.01)

(58) Field of Classification Search
None
See application file for complete search history.

(56) References Cited

U.S. PATENT DOCUMENTS

| 5,470,727 A | 11/1995 | Mascarenhas et al. |
| 2003/0096246 A1 | 5/2003 | Slater et al. |

OTHER PUBLICATIONS

Aihara et al., "An interlocked dimer of the protelomerase TelK distorts DNA structure for the formation of hairpin telomeres" *Mol. Cell*, (2007) 26(6):901-13.
Allardet-Servent et al., "Presence of one linear and one circular chromosome in the Agrobacterium tumefaciens C58 genome" *J. Bacteirol*, 175:7869-7869 (1993).
Casjens, Sherwood R. et al., "The pK02 linear plasmid prophage of Klensiella oxytoca" *Journal of Bacteriology*, vol. 186, No. 6, pp. 1818-1832, (2004)—XP002436436—ISSN: 0021-9193.
Deneke et al., "Catalytic Residues of the Telomere Resolvase ResT a pattern similar to, but distinct from tyrosine recominases and type 1B topoisomerases" (2004) *The Jurnal of Biological Chemistry*, 279, 53699-53706.
Deneke et al., "The protelomerase of temperate *Escherichia coli* phage N15 has cleaving-joining activity" *PNAS* (2000) vol. 97, No. 14, 7721-7726.
Dorokhov, B.D. et al., "Expression Regulation of the Protelomerase Gene of the N15 Bacteriophage" *Molekulrna Genetika Mikrobiologi I Virusplogi, Medecina*, Moscow, RU, No. 2, pp. 28-32, (2004)—XP009084719—ISSN: 0208-0613.
Gerdes et al., "Plasmid and chromosome partitioning: surprises from phylogeny" (2000) *Mol. Microbiol* 37(3):455-66.
Godiska, et al., "Linear plasmid vector for cloning of repetitive or unstable sequences in *Escherichia coli*" *Nuclein Acids Research*, 2010, vol. 38, No. 6.
Hertwig, Stefan et al., "PY54, a linear plasmid prophage of Yersinia enterocolitica with covalently closed ends" *Molecular Microbiology*, vol. 48, No. 4, pp. 989-1003, (2003)—XP002436437—ISSN: 0950-382X.
Huang et al., "Linear Chromosome-generating System of *Agrobacterium tumefaciens* C58: Protelomerase Generates and Protects Hairpin Ends" *J. Biol. Chem.*, 287:25551-25563 (2012).
Huang, W.M. et al., "Protelomerase Uses a Topoisomerase IB/Y-Recombinase Type Mechanism to Generate DNA Hairpin Ends" *Journal of Molecular Biology*, London, GB, vol. 337, No. 1, pp. 77-92, (2004),—XP004491619—ISSN: 0022-2836.
Hyun-Jin et al., "Partitioning of the Linear Chromosome during Sporulation of *Streptomyces coelicolor* A3(2) Involves an oriC-Linked parAB Locus" *Journal of Bacteriology*, Mar. 2000, p. 1313-1320.
Libante et al., "Role of the ATP-binding site of SopA protein in partition of the F plasmid" *J. Mol.Biol* Nov. 30, 2001; 314(3):387-99.
Lobocka et al., "Characterization of the primary immunity region of the *Escherichia coli* Linear Plasmid Prophage N15" *Journal of Bacteriology*, May 1996, p. 2902-2910.
Lodish et al., "Section 7.1 DNA Cloning with Plasmid Vectors" *Molecular Cell Biology*, 4th Edition, New York, W.H.
Mardonov et al., Tightly regulated, high-level expression from controlled copy number vectors based on the replicon of temperate phage N15: *Gene* 395 (2007) 15-21.
Mardanov et al., "The Antipressor Needed for Induction of Linear Plasmid-Prophage N15 Belongs to the SOS Regulon" *Journal of Bacteriology*, Sep. 2007, p. 6333-6338.
Mori et al., Purification and characterization of SopA and SopB proteins essential for F plasmid partitioning *The Journal of Biological Chemistry* vol. 264, No. 26, 1989, pp. 15535-15541.
Ravin, Nikolai V. et al., "The protelomerase of the phage-plasmid N15 is responsible for its maintenance in linear form" *Journal of Molecular Biology*, London, GB, vol. 312, No. 5, pp. 899-906, (2001)—XP004490133—ISSN: 0022-2836.

(Continued)

*Primary Examiner* — Nancy Treptow
(74) *Attorney, Agent, or Firm* — Daniel A. Blasiole; Joseph T. Leone; DeWitt Ross & Stevens S.C.

(57) ABSTRACT

Linear vectors derived from bacteriophage of *E. coli* and host cells suitable for cloning are provided. The linear vectors include a left arm comprising a left telomere and a first selectable marker, a right arm comprising a right telomere and a second selectable marker and a cloning region located between the left arm and the right arm. Optional further components of the vector include transcriptional termination sequences, multiple cloning sites and reporter stuffer regions.

32 Claims, 10 Drawing Sheets

(56) References Cited

OTHER PUBLICATIONS

Ravin, Nikolai V. et al., "Bidirectional replication from an internal ori site of the linear N15 plasmid prophage" *Nucleic Acids Research*, vol. 31, No. 22, pp. 6552-6560, (2003)—XP002436435—ISSN: 0305-1048.

Riedel et al., "The antirepressor of phage P1 Isolation and interaction with the C1 repressor of P1 and P7" *Federation of European Biochemical Societies* vol. 334, No. 2, 165-169.

Vostrov, A.A. et al., "Construction of Linear Plasmid Vectors for Cloning in *Escherichia Coli* Cells" *Genetika*, Moscow, RU, vol. 28, No. 7, pp. 186-188 (1992)—XP009084736—ISSN: 0016-6758.

NgoMIV Digest: (15 kb, 0.4 kb, 19 kb) or (19 kb, 0.4 kb, 15 kb)

SpeI Digest: (12 kb, 13 kb, 9 kb) or (12 kb, 17 kb, 5 kb)

SEQUENCE LISTING

```
<160> NUMBER OF SEQ ID NOS: 45

<210> SEQ ID NO 1
<211> LENGTH: 13165
<212> TYPE: DNA
<213> ORGANISM: Artificial Sequence
<220> FEATURE:
<223> OTHER INFORMATION: Vector pG591
<220> FEATURE:
<221> NAME/KEY: misc_feature
<222> LOCATION: (10741)..(10741)
<223> OTHER INFORMATION: n is a, c, g, or t
<220> FEATURE:
<221> NAME/KEY: misc_feature
<222> LOCATION: (10987)..(10987)
<223> OTHER INFORMATION: n is a, c, g, or t

<400> SEQUENCE: 1
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480
cctctttaca gcgaagaatt atcttcatgg ctttctatgc ctacggctaa tattcgccag     540
cacatgtcat cgttacaatc taaattgaaa gaaataatgc cgcttgccga agagttatca     600
aatgtaagaa taggctctaa aggcagtgat gcaaaaatag caagactaat aaaaaaatat     660
ccagattgga gttttgctct tagtgattta aacagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta tacttatgc     1140 gaagcaaaat tattcgttga attattaaca gaattgcgtt cttgctctgc tgcatctgat    1200
ttcgatgagg ttgttaaagg atatgaaag gatgatacaa ggtctgagaa cggcaggata    1260
aatgctattt tagcaaaagc atttaacct tgggttaaat cattttttcgg cgatgaccgt    1320
```

```
cgtgtttata aagatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcggaaactg cagctgcaac tacggacatc gccgtcccga ctgcagggac    2220
ttccccgcgt aaagcggggc ttaaattcgg gctggccaac cctattttc tgcaatcgct    2280 ggcgatgtta gtttcgtgga tagcgtttcc agcttttcaa tggccagctc aaaatgtgct    2340
ggcagcacct tctccagttc cgtatcaata tcggtgatcg gcagctctcc acaagacata    2400
ctccggcgac cgccacgaac tacatcgcgc agcagctccc gttcgtagac acgcatgttg    2460
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact tccctggcca tccgatcaag ttttttgtgcc    2880 tcggttaaac cgagggtcaa ttttttcatca tgatccagct tacgcaatgc atcagaaggg    2940
ttggctatat tcaatgcagc acagatatcc agcgccacaa accacgggtc accaccgaca    3000
agaaccaccc gtatagggtg gctttcctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat ttttttgtccg tgcggacgac    3420 agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
```

```
aggcccggct gcagattttg ctgcagcggg gtaactctac cgccaaagca gaacgcacgt    3720
caataattta ggtggatatt ttaccccgtg accagtcacg tgcacaggtg ttttttatagt    3780 ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat    4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg aagttcccg gccagtttta    4980 taatcgctat agcttgtcgc gtcgtggctg accttgacca cataagggtc gtagccctcc    5040
acgatgacaa ggcattcccg ttgttttccc attaccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgcttttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggtttttg gatcgatacc gcagtcgcgg aagtactgct    5760
gcagcgtcgc cgatttgagg gtgtagaaac cacgcatgcc tatctcaaca gcagggtcg    5820 atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttttcaggc cgccgtcgaa atagaatttt aacgccacct    6060
```

```
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900 gattttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg cgcgggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt ctgcgatac    7680 ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgcccg gtggcgaaac    8220 cctctgcagt cgcaatttt tgcgccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
```

```
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggttttttt tcgtcttttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900
catacccttt atcataaatg atctctttat agctggctat aatttttata aattataccct    9960 agctttaatt ttcacttatt gattataata atccccatga aacccgaaga acttgtgcgc    10020
catttcggcg atgtggaaaa agcagcggtt ggcgtgggcg tgacacccgg cgcagtctat    10080
caatggctgc aagctgggga gattccacct ctacgacaaa gcgatataga ggtccgtacc    10140
gcgtacaaat taagagtga tttcacctct cagcgcatgg gtaaggaagg gcataacagg    10200
ggatcctcta gagtcgacct gcaggcatgc aagcttcctg aatcgcccca tcatccagcc    10260
agaaagtgag ggagccacgg ttgatgagag ctttgttgta ggtggaccag ttggtgattt    10320
tgaacttttg ctttgccacg gaacggtctg cgttgtcggg aagatgcgtg atctgatcct    10380
tcaactcagc aaaagttcga tttattcaac aaagccgccg tccgtcaag tcagcgtaat    10440 gctctgccag tgttacaacc aattaaccaa ttctgattag aaaaactcat cgagcatcaa    10500
atgaaactgc aatttattca tatcaggatt atcaatacca tttttgaa aaagccgttt    10560 ctgtaatgaa ggagaaaact caccgaggca gttccatagg atggcaagat cctggtatcg    10620
gtctgcgatt ccgactcgtc caacatcaat acaacctatt aatttcccct cgtcaaaaat    10680
aaggttatca agtgagaaat caccatgagt gacgactgaa tccggtgaga atggcaaaag    10740
nttatgcatt tctttccaga cttgttcaac aggccagcca ttacgctcgt catcaaaatc    10800
```

```
actcgcatca accaaaccgt tattcattcg tgattgcgcc tgagcgagac gaaatacgcg    10860
atcgctgtta aaaggacaat tacaaacagg aatcgaatgc aaccggcgca ggaacactgc    10920
cagcgcatca acaatatttt cacctgaatc aggatattct tctaatacct ggaatgctgt    10980
tttcccnggg atcgcagtgg tgagtaacca tgcatcatca ggagtacgga taaaatgctt    11040
gatggtcgga agaggcataa attccgtcag ccagtttagt ctgaccatct catctgtaac    11100
atcattggca acgctacctt tgccatgttt cagaaacaac tctggcgcat cgggcttccc    11160
atacaatcga tagattgtcg cacctgattg cccgacatta tcgcgagccc atttataccc    11220
atataaatca gcatccatgt tggaatttaa tcgcggcctc gagcaagacg tttcccgttg    11280
aatatggctc ataacacccc ttgtattact gtttatgtaa gcagacagtt ttattgttca    11340
tgatgatata tttttatctt gtgcaatgta acatcagaga ttttgagaca caacgtggct    11400
ttgttgaata aatcgaactt tgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatgggcga ttcaggaagc    11580 ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggcctttt    11820
cgactttatc agcaggaatg gtttccagct taaaagtcac gttgcggccg caaaccggta    11880
gcgtaatgct attcccggac aacgaactta atttgctctg taagtcgcca accatcggcg    11940
aaaccgatgg cgcttttgc ggcgcattat ggttattgct catgaacgtt tcgatgttgg    12000
gcgcattttt taatatagag cgattcttca tagttagtcc tcccaacgag gtttgattag    12060
atctgtttca atgcggtgaa gggccaggca gctggggatt atgtcgagac ccggccagca    12120
tgttggtttt atcgcatatt cagcgttgtc gcgtttaccc aggtaaaatg gaagcagtgt    12180
atcgtctgcg tgaatgtgca aatcaggaac gtaaccgtgg tacatagatg cagtcccttg    12240
cgggtcgttc ccttcaacga gtaggacgcg gtgcccttgc aaggctaacc attgcgcctg    12300
gtgtactgca gatgaggttt tataaacccc tcccttgtgt gacataacgg aaagtacaac    12360 cgggtttta tcgtcaggtc tttggtttgg gttaccaaac acactccgca tatggctaat    12420
ttggtcaatt gtgtagccag cgcgacgttc tactcggccc ctcatctcaa aatcaggagc    12480
cggtagacga ccagcttttt ccgcgtctct gatagcctgc ggtgttacgc cgatcaggtc    12540
tgcaacttct gttataccc agcggcgagt aatacgacgc gcttccgggc tgtcatcgcc    12600
gaactgtgcg atgcaatag cgcgcgtcat ttcctgaccg cgattgatac agtctttcag    12660
caaattaatt aacgacatcc tgtttcctct caaacatgcc cttatctttg tgtttttcat    12720
catactttac gttttaaag caaagcaaca taaaaaagc aaagtgactt agaaaacgca    12780
aagttaaggt tcaaatcaat tttttgatgc gctacagaag ctatttagct tcatctaagc    12840
gcaacggtat tacttacgtt ggtatatta aaacctaact taatgatttt aaatgataat    12900
aaatcatacc aattgctatc aaaagttaag cgaacatgct gattttcacg ctgttttatac    12960 actttgaggc atctctatct cttccgtctc tatattgaaa cacaatcaaa gaacatcaat    13020
ccatgtgaca tcccccacta tctaagaaca ccataacaga acacaacata ggaatgcaac    13080
attaatgtat caataattcg gaacatatgc actatatcat atctcaatta cggaacatat    13140
```

| | |
|---|---|
| cagcacacaa ttgcccatta tacgc | 13165 |

<210> SEQ ID NO 2
<211> LENGTH: 12827
<212> TYPE: DNA
<213> ORGANISM: Artificial Sequence
<220> FEATURE:
<223> OTHER INFORMATION: Vector NZOC (NZTC3 or pJAZZ-OC)

<400> SEQUENCE: 2

| | |
|---|---|
| gcgtataatg gactattgtg tgctgataag gagaacataa gcgcagaaca atatgtatct | 60 |
| attccggtgt tgtgttcctt tgttattctg ctattatgtt ctcttatagt gtgacgaaag | 120 |
| cagcataatt aatcgtcact tgttctttga ttgtgttacg atatccagag acttagaaac | 180 |
| gggggaaccg ggatgagcaa ggtaaaaatc ggtgagttga tcaacacgct tgtgaatgag | 240 |
| gtagaggcaa ttgatgcctc agaccgccca caaggcgaca aaacgaagag aattaaagcc | 300 |
| gcagccgcac ggtataagaa cgcgttattt aatgataaaa gaaagttccg tgggaaagga | 360 |
| ttgcagaaaa gaataaccgc gaatactttt aacgcctata tgagcagggc aagaaagcgg | 420 |
| tttgatgata aattacatca tagctttgat aaaaatatta ataaattatc ggaaaagtat | 480 |
| cctctttaca gcgaagaatt atcttcatgg ctttctatgc ctacggctaa tattcgccag | 540 |
| cacatgtcat cgttacaatc taaattgaaa gaaataatgc cgcttgccga gagttatca | 600 |
| aatgtaagaa taggctctaa aggcagtgat gcaaaaatag caagactaat aaaaaatat | 660 |
| ccagattgga gttttgctct tagtgattta acagtgatg attggaagga gcgccgtgac | 720 |
| tatctttata agttattcca acaaggctct gcgttgttag aagaactaca ccagctcaag | 780 |
| gtcaaccatg aggttctgta ccatctgcag ctaagccctg cggagcgtac atctatacag | 840 |
| caacgatggg ccgatgttct gcgcgagaag aagcgtaatg ttgtggttat tgactaccca | 900 |
| acatacatgc agtctatcta tgatattttg aataatcctg cgactttatt tagtttaaac | 960 |
| actcgttctg gaatggcacc tttggccttt gctctggctg cggtatcagg gcgaagaatg | 1020 |
| attgagataa tgtttcaggg tgaatttgcc gtttcaggaa agtatacggt taatttctca | 1080 |
| gggcaagcta aaaacgctc tgaagataaa agcgtaacca gaacgattta ctttatgc | 1140 |
| gaagcaaaat tattcgttga attattaaca gaattgcgtt cttgctctgc tgcatctgat | 1200 |
| ttcgatgagg ttgttaaagg atatggaaag gatgatacaa ggtctgagaa cggcaggata | 1260 |
| aatgctattt tagcaaaagc atttaacct tggttaaat catttttcgg cgatgaccgt | 1320 |
| cgtgttata aagatagccg cgctatttac gctcgcatcg cttatgagat gttcttccgc | 1380 |
| gtcgatccac ggtggaaaaa cgtcgacgag gatgtgttct tcatggagat tctcggacac | 1440 |
| gacgatgaga acacccagct gcactataag cagttcaagc tggccaactt ctccagaacc | 1500 |
| tggcgacctg aagttgggga tgaaaacacc aggctggtgg ctctgcagaa actggacgat | 1560 |
| gaaatgccag gctttgccag aggtgacgct ggcgtccgtc tccatgaaac cgttaagcag | 1620 |
| ctggtggagc aggaccccatc agcaaaaata accaacagca ctctccgggc ctttaaattt | 1680 |
| agcccgacga tgattagccg gtacctggag tttgccgctg atgcattggg gcagttcgtt | 1740 |
| ggcgagaacg ggcagtggca gctgaagata gagacacctg caatcgtcct gcctgatgaa | 1800 |
| gaatccgttg agaccatcga cgaaccggat gatgagtccc aagacgacga gctggatgaa | 1860 |
| gatgaaattg agctcgacga gggtggcggc gatgaaccaa ccgaagagga agggccagaa | 1920 |
| gaacatcagc caactgctct aaaacccgtc ttcaagcctg caaaaaataa cggggacgga | 1980 |
| acgtacaaga tagagtttga atacgatgga aagcattatg cctggtccgg ccccgccgat | 2040 |

```
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcgggc ttaaattcgg gctggccaac cctattttc tgcaatcgct    2280 ggcgatgtta gtttcgtgga tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag ttttgtgcc    2880 tcggttaaac cgagggtcaa ttttcatca tgatccagct tacgcaatgc atcagaaggg    2940
ttggctatat tcaatgcagc acagatatcc agcgccacaa accacgggtc accaccgaca   3000
agaaccaccc gtataggggtg ctttcctga atgaaaaga cggagagagc cttcattgcg    3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa gcgcttcaac ctgcagcagg cgttcctcaa   3240
tcgtctccag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcaatggtgg aaaggcggtg gatatgggat ttttgtccg tgcggacgac    3420 agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggcccccat ctgagccacc ataattcagg tatgcgcaga   3600
tttaacacac aaaaaaacac gctggcgcgt gttgtgcgct tcttgtcatt cggggttgag   3660
aggcccggct gcagatttg ctgcagcggg gtaactctac cgccaaagca gaacgcacgt    3720
caataattta ggtggatatt ttaccccgtg accagtcacg tgcacaggtg ttttatagt    3780 ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc cagaacgtcg   3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtcctttaaa taaggctgta gaactgcaaa   4200
atcgctctcg ttcacatgct gtacgtagat gcgtagcaaa ttgccgttcc atccctgtaa   4260 tccacccttct ttggaaagat cgtccttgac ctcacgaaga accttatcca atagccctgc   4320
ggcacaagaa attgcctgct ctggatcagc aaattcatat tgattaatag gtgattgcca   4380
```

```
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc tttttctctt cggcctcaat    4740
agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attaccccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggtttttg gatcgatacc gcagtcgcgg aagtactgct    5760
gcagcgtcgc cgatttgagg gtgtagaaac cacgcatgcc tatctcaaca gcagggg tcg    5820 atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttttcaggc cgccgtcgaa atagaatttt aacgccacct    6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
```

```
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga accgcaatg actaccgcgt    8160
caaagcgttt tttcgggtcg tttctggtcg ccagccagat ggatgccccg gtggcgaaac    8220
cctctgcagt cgcaatttt tgcgcccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attcccttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catcgctttt tcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
```

-continued

```
caataaacgc actatctttc tgaaggacgt atctgcgtta tcgtggctac ttcctgaaaa    9180
aggcccgagt tgccgactc gggttttttt tcgtctttt tcggctgcta cggtctggtt     9240
caaccccgac aaagtataga tcggattaaa ccagaattat agtcagcaat aaaccctgtt   9300
attgtatcat ctaccctcaa ccatgaacga tttgatcgta ccgactactt ggtgcacaaa   9360
ttgaagatca cttttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacgt ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc   9660
ggtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900
cataccctta atcataaatg atctctttat agctggctat aattttata aattataacct  9960
agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatggctgc aagctgggga gattccacct ctacgacaaa gcgatataga ggtccgtacc  10140
gcgtacaaat taaagagtga tttcacctct cagcgcatgg gtaaggaagg gcataacagg  10200
ggatcctcta gacagtccag ttacgctgga gtcactagtg cggccgcgac aacttgtcta  10260
gggcccaatg gcccgggagg cctacttaag taagccggct tagctagcgg gacaggtttc  10320
ccgactggaa agcgggcagt gagcgcaacg caattaatgt gagttagctc actcattagg  10380
cacccccaggc tttacacttt atgcttccgg ctcgtatgtt gtgtggaatt gtgagcggac  10440
aacaatttca cacaggaaac agctatgacc atgattacgc caagctattt aggtgagact  10500
atagaatact caagcttgca tgcgatacgt atcgttaacg atggatccga cgcacgtgcg  10560
aattcgccct atagtgagtc gtattacaat tcactggccg tcgttttaca acgtcgtgac  10620
tgggaaaacc ctggcgtcac ccaacttaat cgccttgcag cacatccccc tttcgccagc  10680
tggcgtaata gcgaagaggc ccgcaccgat cgcccttccc aacagttgcg cagctgaatg  10740
gcgaatctta agtaggcctc ccgggccatt agacttgaag tcaagcggcc gctacaactg  10800
gaccttgctg gtacatagaa ctgattaact gaccatttaa atcataccaa catggtcaaa  10860
taaaacgaaa ggctcagtcg aaagactggg cctttcgttt taatctgatc ggcacgtaag  10920
aggttccaac tttcaccata atgaaataag atcactaccg ggcgtatttt ttgagttatc  10980
gagattttca ggagctaagg aagctaaaat ggagaaaaaa atcactggat ataccaccgt  11040
tgatatatcc caatggcatc gtaaagaaca ttttgaggca tttcagtcag ttgctcaatg  11100
tacctataac cagaccgttc agctggatat tacggccttt ttaaagaccg taagaaaaaa  11160
taagcacaag ttttatccgg cctttattca cattcttgcc cgcctgatga atgctcatcc  11220
ggaatttcgt atggcaatga aagacggtga gctggtgata tgggatagtg ttcacccttg  11280
ttacaccgtt ttccatgagc aaactgaaac gttttcatcg ctctggagtg aataccacga  11340
cgatttccgg cagtttctac acatatattc gcaagatgtg gcgtgttacg gtgaaaacct  11400
ggcctatttc cctaaagggt ttattgagaa tatgtttttc gtctcagcca atccctgggt  11460
gagtttcacc agttttgatt taaacgtggc caatatggac aacttcttcg ccccgttttt  11520
```

```
caccatgggc aaatattata cgcaaggcga caaggtgctg atgccgctgg cgattcaggt    11580
tcatcatgcc gtttgtgatg gcttccatgt cggcagaatg cttaatgaat tacaacagta    11640
ctgcgatgag tggcagggcg gggcgtaacc taggtgacag aagtcaaaag cctccggtcg    11700
gaggcttttg actttctgct agatctgttt caatgcggtg aagggccagg cagctgggga    11760
ttatgtcgag acccggccag catgttggtt ttatcgcata ttcagcgttg tcgcgtttac    11820
ccaggtaaaa tggaagcagt gtatcgtctg cgtgaatgtg caaatcagga acgtaaccgt    11880
ggtacataga tgcagtccct tgcgggtcgt tcccttcaac gagtaggacg cggtgccctt    11940
gcaaggctaa ccattgcgcc tggtgtactg cagatgaggt tttataaacc cctcccttgt    12000
gtgacataac ggaaagtaca accgggtttt tatcgtcagg tctttggttt gggttaccaa    12060
acacactccg catatggcta atttggtcaa ttgtgtagcc agcgcgacgt tctactcggc    12120
ccctcatctc aaaatcagga gccggtagac gaccagcttt ttccgcgtct ctgatagcct    12180
gcggtgttac gccgatcagg tctgcaactt ctgttatacc ccagcggcga gtaatacgac    12240
gcgcttccgg gctgtcatcg ccgaactgtg cgatggcaat agcgcgcgtc atttcctgac    12300
cgcgattgat acagtctttc agcaaattaa ttaacgacat cctgtttcct ctcaaacatg    12360
cccttatctt tgtgtttttc atcatacttt acgttttaa agcaaagcaa cataaaaaaa     12420
gcaaagtgac ttagaaaacg caaagttaag gttcaaatca atttttttgat gcgctacaga   12480 agctatttag cttcatctaa gcgcaacggt attacttacg ttggtatatt taaaacctaa    12540
cttaatgatt ttaaatgata ataaatcata ccaattgcta tcaaaagtta agcgaacatg    12600
ctgattttca cgctgtttat acactttgag gcatctctat ctcttccgtc tctatattga    12660
aacacaatca agaacatca atccatgtga catcccccac tatctaagaa caccataaca     12720
gaacacaaca taggaatgca acattaatgt atcaataatt cggaacatat gcactatatc    12780
atatctcaat tacggaacat atcagcacac aattgcccat tatacgc                  12827
```

<210> SEQ ID NO 3
<211> LENGTH: 14600
<212> TYPE: DNA
<213> ORGANISM: Artificial Sequence
<220> FEATURE:
<223> OTHER INFORMATION: Vector NZAN (pJAZZ-KA or pNZKA)

<400> SEQUENCE: 3

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta taaattatc ggaaaagtat      480 cctctcttaca gcgaagaatt atcttcatgg ctttctatgc ctacggctaa tattcgccag    540
cacatgtcat cgttacaatc taaattgaaa gaataatgc cgcttgccga agagttatca      600
aatgtaagaa taggctctaa aggcagtgat gcaaaaatag caagactaat aaaaaaatat     660
ccagattgga gttttgctct tagtgattta aacagtgatg attggaagga gcgccgtgac    720
```

```
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct cgcgcgagaag aagcgtaatg ttgtggttat tgactaccca   900
acatacatgc agtctatcta tgatattttg aataatcctg cgactttatt tagtttaaac   960
actcgttctg gaatggcacc tttggccttt gctctggctg cggtatcagg gcgaagaatg  1020
attgagataa tgtttcaggg tgaatttgcc gtttcaggaa agtatacggt taatttctca  1080
gggcaagcta aaaacgctc tgaagataaa agcgtaacca gaacgattta tactttatgc   1140
gaagcaaaat tattcgttga attattaaca gaattgcgtt cttgctctgc tgcatctgat  1200
ttcgatgagg ttgttaaagg atatggaaag gatgatacaa ggtctgagaa cggcaggata  1260
aatgctattt tagcaaaagc atttaaccct tgggttaaat cattttttcgg cgatgaccgt  1320
cgtgtttata aagatagccg cgctatttac gctcgcatcg cttatgagat gttcttccgc  1380
gtcgatccac ggtggaaaaa cgtcgacgag gatgtgttct tcatggagat tctcggacac  1440
gacgatgaga acacccagct gcactataag cagttcaagc tggccaactt ctccagaacc  1500
tggcgacctg aagttgggga tgaaaacacc aggctggtgg ctctgcagaa actggacgat  1560
gaaatgccag gctttgccag aggtgacgct ggcgtccgtc tccatgaaac cgttaagcag  1620
ctggtggagc aggacccatc agcaaaaata ccaacagca ctctccgggc ctttaaattt    1680
agcccgacga tgattagccg gtacctggag tttgccgctg atgcattggg gcagttcgtt  1740
ggcgagaacg ggcagtggca gctgaagata gagacacctg caatcgtcct gcctgatgaa  1800
gaatccgttg agaccatcga cgaaccggat gatgagtccc aagacgacga gctggatgaa  1860
gatgaaattg agctcgacga gggtggcggc gatgaaccaa ccgaagagga agggccagaa  1920
gaacatcagc caactgctct aaaacccgtc ttcaagcctg caaaaaataa cggggacgga  1980
acgtacaaga tagagtttga atacgatgga aagcattatg cctggtccgg ccccgccgat  2040
agccctatgg ccgcaatgcg atccgcatgg gaaacgtact acagctaaaa gaaaagccac  2100
cggtgttaat cggtggcttt tttattgagg cctgtcccta cccatcccct gcaagggacg  2160
gaaggattag gcgaaactg cagctgcaac tacggacatc gccgtcccga ctgcagggac   2220
ttccccgcgt aaagcggggc ttaaattcgg gctggccaac cctattttc tgcaatcgct   2280
ggcgatgtta gttcgtgga tagcgttcc agcttttcaa tggccagctc aaaatgtgct    2340
ggcagcacct tctccagttc cgtatcaata tcggtgatcg gcagctctcc acaagacata  2400
ctccggcgac cgccacgaac tacatcgcgc agcagctccc gttcgtagac acgcatgttg  2460
cccagagccg tttctgcagc cgttaatatc cggcgcagct cggcgatgat tgccgggaga  2520
tcatccacgg ttattgggtt cggtgatggg ttcctgcagg cgcggcggag agccatccag  2580
acgccgctaa cccatgcgtt acggtactga aaactttgtg ctatgtcgtt tatcaggccc  2640
cgaagttctt ctttctgccg ccagtccagt ggttcaccgg cgttcttagg ctcaggctcg  2700
acaaaagcat actcgccgtt tttccggata gctggcagaa cctcgttcgt cacccacttg  2760
cggaaccgcc aggctgtcgt ccctgttttc accgcgtcgc ggcagcggag gattatggtg  2820
tagagaccag attccgatac cacatttact tccctggcca tccgatcaag tttttgtgcc  2880
tcggttaaac cgagggtcaa tttttcatca tgatccagct tacgcaatgc atcagaaggg  2940
ttggctatat tcaatgcagc acagatatcc agcgccacaa accacgggtc accaccgaca  3000
agaaccaccc gtatagggtg ctttcctga aatgaaaaga cggagagagc cttcattgcg   3060
cctccccgga tttcagctgc tcagaaaggg acagggagca gccgcgagct tcctgcgtga  3120
```

```
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat ttttgtccg tgcggacgac      3420 agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020 ttttgctgc ttccgagtag caatcctctt caccacaaag aaagttactt atctgcttcc     4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttgt agatcatgcg ccactattca     4500
cccccactgg ccatcagcaa ataaagcttc tactcggac accggcaggc ggcttccacg     4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat   4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
```

```
tattcatgag gaactcgacc gagtccgggt caatggaacg catcgtgggg cgtgcatcgc   5520
cgtctctggc gcgtctggtc ttactggata gccccataga ctccaggatg cctatgcaga   5580
ggtctgcagg cgctttcttc ttgccttttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggtttttg gatcgatacc gcagtcgcgg aagtactgct   5760
gcagcgtcgc cgatttgagg gtgtagaaac cacgcatgcc tatctcaaca gcagggtcg    5820 atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360 cggcttttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780 tttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gccttttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg cacggcatt    7620 tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacaggtcg gttgcacggc   7860
```

```
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgcccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt tcaacgaagt taacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggtttttt tcgtcttttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccctta atcataaatg atctctttat agctggctat aatttttata aattataccct   9960 agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg gcataacagg   10200
```

```
ggatcctcta gagtcgacct gcaggcatgc aagcttcctg aatcgcccca tcatccagcc    10260
agaaagtgag ggagccacgg ttgatgagag ctttgttgta ggtggaccag ttggtgattt    10320
tgaacttttg ctttgccacg gaacggtctg cgttgtcggg aagatgcgtg atctgatcct    10380
tcaactcagc aaaagttcga tttattcaac aaagccgccg tcccgtcaag tcagcgtaat    10440
gctctgccag tgttacaacc aattaaccaa ttctgattag aaaaactcat cgagcatcaa    10500
atgaaactgc aatttattca tatcaggatt atcaatacca tatttttgaa aaagccgttt    10560
ctgtaatgaa ggagaaaact caccgaggca gttccatagg atggcaagat cctggtatcg    10620
gtctgcgatt ccgactcgtc caacatcaat acaacctatt aatttcccct cgtcaaaaat    10680
aaggttatca agtgagaaat caccatgagt gacgactgaa tccggtgaga atggcaaaag    10740
cttatgcatt tctttccaga cttgttcaac aggccagcca ttacgctcgt catcaaaatc    10800
actcgcatca accaaaccgt tattcattcg tgattgcgcc tgagcgagac gaaatacgcg    10860
atcgctgtta aaaggacaat tacaaacagg aatcgaatgc aaccggcgca ggaacactgc    10920
cagcgcatca acaatatttt cacctgaatc aggatattct tctaataacct ggaatgctgt    10980 tttccctggg atcgcagtgg tgagtaacca tgcatcatca ggagtacgga taaaatgctt    11040
gatggtcgga agaggcataa attccgtcag ccagtttagt ctgaccatct catctgtaac    11100
atcattggca acgctacctt tgccatgttt cagaaacaac tctggcgcat cgggcttccc    11160
atacaatcga tagattgtcg cacctgattg cccgacatta tcgcgagccc atttatccc    11220 atataaatca gcatccatgt tggaatttaa tcgcggcctc gagcaagacg tttcccgttg    11280
aatatggctc ataacacccc ttgtattact gtttatgtaa gcagacagtt ttattgttca    11340
tgatgatata ttttatctt gtgcaatgta acatcagaga ttttgagaca aacgtggct    11400 ttgttgaata aatcgaactt tgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatggggcga ttcaggaagc    11580
ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggccttt    11820 cgactttatc agcaggaatg gtttccagct aaaagtcac gttgcggcca tcaagcttga    11880
attcgtacgc agaaaggccc acccgaaggt gagccagtgt gattacattt gcggccgcat    11940
ttaaatgggc ccgggacagg tttcccgact ggaaagcggg cagtgagcgc aacgcaatta    12000
atgtgagtta gctcactcat taggcacccc aggctttaca ctttatgctt ccggctcgta    12060
tgttgtgtgg aattgtgagc ggacaacaat ttcacacagg aaacagctat gaccatgatt    12120
acgccaagct atttaggtga actatagaa tactcaagct tgcatgcgat acgtatcgtt    12180
tacgatggat ccgacgcacg tgcgaattcg ccctatagtg agtcgtatta caattcactg    12240
gccgtcgttt tacaacgtcg tgactgggaa aaccctggcg tcacccaact taatcgcctt    12300
gcagcacatc cccctttcgc cagctggcgt aatagcgaag aggcccgcac cgatcgccct    12360
tcccaacagt tgcgcagctg aatggcgaat ggcgcctgag ggcccgggat ggcgcgccat    12420
gcggccgcca tggtcaaata aaacgaaagg ctcagtcgaa agactgggcc tttcgtttta    12480
atctgatcgg cacgtaagag gttccaactt tcaccataat gaaataagat cactaccggg    12540
cgtatttttt gagttatcga gattttcagg agctaaggaa gctaaaatga gtattcaaca    12600
```

```
tttccgtgtc gcccttattc ccttttttgc ggcattttgc cttcctgttt ttgctcaccc   12660
agaaacgctg gtgaaagtaa aagatgctga agatcagttg ggtgcacgag tgggttacat   12720
cgaactggat ctcaacagcg gtaagatcct tgagagttta cgccccgaag aacgttttcc   12780
aatgatgagc acttttaaag ttctgctatg tggcgcggta ttatcccgta ttgacgccgg   12840
gcaagagcaa ctcggtcgcc gcatacacta ttctcagaat gacttggttg agtactcacc   12900
agtcacagaa aagcatctca cggatggcat gacagtaaga gaattatgca gtgctgccat   12960
aaccatgagt gataacactg cggccaactt acttctggca acgatcggag gaccgaagga   13020
gctaaccgct ttttgcaca acatggggga tcatgtaact cgccttgatc gttgggaacc   13080
ggagctgaat gaagccatac caaacgacga gcgtgacacc acgatgcctg tagcaatggc   13140
aacaacgttg cgcaaactat taactggcga actacttact ctagcttccc ggcaacaatt   13200
aatagactgg atggaggcgg ataaagttgc aggatcactt ctgcgctcgg ccctcccggc   13260
tggctggttt attgctgata atctggagc cggtgagcgt gggtctcgcg gtatcattgc   13320
agcactgggg ccagatggta agccctcccg catcgtagtt atctacacga cggggagtca   13380
ggcaactatg gatgaacgaa atagacagat cgctgagata ggtgcctcac tgattaagca   13440
ttggtaatga cagaagtcaa aagcctccgg tcggaggctt ttgactttct gctagatctg   13500
tttcaatgcg gtgaagggcc aggcagctgg ggattatgtc gagacccggc cagcatgttg   13560
gttttatcgc atattcagcg ttgtcgcgtt tacccaggta aaatggaagc agtgtatcgt   13620
ctgcgtgaat gtgcaaatca ggaacgtaac cgtggtacat agatgcagtc ccttgcgggt   13680
cgttcccttc aacgagtagg acgcggtgcc cttgcaaggc taaccattgc gcctggtgta   13740
ctgcagatga ggttttataa accctcct tgtgtgacat aacggaaagt acaaccgggt   13800
ttttatcgtc aggtctttgg tttgggttac caaacacact ccgcatatgg ctaatttggt   13860
caattgtgta gccagcgcga cgttctactc ggcccctcat ctcaaaatca ggagccggta   13920
gacgaccagc ttttccgcg tctctgatag cctgcggtgt tacgccgatc aggtctgcaa   13980
cttctgttat accccagcgg cgagtaatac gacgcgcttc cgggctgtca tcgccgaact   14040
gtgcgatggc aatagcgcgc gtcatttcct gaccgcgatt gatacagtct ttcagcaaat   14100
taattaacga catcctgttt cctctcaaac atgcccttat ctttgtgttt ttcatcatac   14160
tttacgtttt taaagcaaag caacataaaa aaagcaaagt gacttagaaa acgcaaagtt   14220
aaggttcaaa tcaatttttt gatgcgctac agaagctatt tagcttcatc taagcgcaac   14280
ggtattactt acgttggtat atttaaaacc taacttaatg attttaaatg ataataaatc   14340
ataccaattg ctatcaaaag ttaagcgaac atgctgattt tcacgctgtt tatacacttt   14400
gaggcatctc tatctcttcc gtctctatat tgaaacacaa tcaaagaaca tcaatccatg   14460
tgacatcccc cactatctaa gaacaccata acagaacaca acataggaat gcaacattaa   14520
tgtatcaata attcggaaca tatgcactat atcatatctc aattacggaa catatcagca   14580
cacaattgcc cattatacgc                                              14600
```

<210> SEQ ID NO 4
<211> LENGTH: 14673
<212> TYPE: DNA
<213> ORGANISM: Artificial Sequence
<220> FEATURE:
<223> OTHER INFORMATION: Vector NZASA
<400> SEQUENCE: 4

-continued

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480
cctctttaca gcgaagaatt atcttcatgg ctttctatgc ctacggctaa tattcgccag     540
cacatgtcat cgttacaatc taaattgaaa gaaataatgc cgcttgccga agagttatca     600
aatgtaagaa taggctctaa aggcagtgat gcaaaaatag caagactaat aaaaaaatat     660
ccagattgga gttttgctct tagtgattta acagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagtttaaac     960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaaacgctc tgaagataaa agcgtaacca gaacgattta tactttatgc    1140
gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaaccct tgggttaaat cattttttcgg cgatgaccgt    1320
cgtgtttata agatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
tggcgacctg aagttgggga tgaaaacacc aggctggtgg ctctgcagaa actggacgat    1560
gaaatgccag gctttgccag aggtgacgct ggcgtccgtc tccatgaaac cgttaagcag    1620
ctggtggagc aggacccatc agcaaaaata accaacagca ctctccgggc ctttaaattt    1680
agcccgacga tgattagccg gtacctggag tttgccgctg atgcattggg gcagttcgtt    1740
ggcgagaacg ggcagtggca gctgaagata gagacacctg caatcgtcct gcctgatgaa    1800
gaatccgttg agaccatcga cgaaccggat gatgagtccc aagacgacga gctggatgaa    1860
gatgaaattg agctcgacga gggtggcggc gatgaaccaa ccgaagagga agggccagaa    1920
gaacatcagc caactgctct aaaacccgtc ttcaagcctg caaaaaataa cggggacgga    1980
acgtacaaga tagagtttga atacgatgga aagcattatg cctggtccgg ccccgccgat    2040
agccctatgg ccgcaatgcg atccgcatgg gaaacgtact acagctaaaa gaaaagccac    2100
cggtgttaat cggtggcttt tttattgagg cctgtcccta cccatcccct gcaagggacg    2160
gaaggattag gcggaaactg cagctgcaac tacggacatc gccgtcccga ctgcagggac    2220
ttccccgcgt aaagcggggc ttaaattcgg gctggccaac cctatttttc tgcaatcgct    2280
ggcgatgtta gttcgtgga tagcgtttcc agcttttcaa tggccagctc aaaatgtgct    2340
ggcagcacct tctccagttc cgtatcaata tcggtgatcg gcagctctcc acaagacata    2400
```

```
ctccggcgac cgccacgaac tacatcgcgc agcagctccc gttcgtagac acgcatgttg      2460
cccagagccg tttctgcagc cgttaatatc cggcgcagct cggcgatgat tgccgggaga      2520
tcatccacgg ttattgggtt cggtgatggg ttcctgcagg cgcggcggag agccatccag      2580
acgccgctaa cccatgcgtt acggtactga aaactttgtg ctatgtcgtt tatcaggccc      2640
cgaagttctt ctttctgccg ccagtccagt ggttcaccgg cgttcttagg ctcaggctcg      2700
acaaaagcat actcgccgtt tttccggata gctggcagaa cctcgttcgt cacccacttg      2760
cggaaccgcc aggctgtcgt cccctgtttc accgcgtcgc ggcagcggag gattatggtg      2820
tagagaccag attccgatac cacatttact tccctggcca tccgatcaag ttttgtgcc      2880 tcggttaaac cgagggtcaa tttttcatca tgatccagct tacgcaatgc atcagaaggg      2940
ttggctatat tcaatgcagc acagatatcc agcgccacaa accacgggtc accaccgaca      3000
agaaccaccc gtataggggtg gctttcctga aatgaaaaga cggagagagc cttcattgcg      3060 cctcccccgga tttcagctgc tcagaaaggg acagggagca gccgcgagct tcctgcgtga      3120
gttcgcgcgc gacctgcaga agttccgcag cttcctgcaa atacagcgtg gcctcataac      3180
tggagatagt gcggtgagca gagcccacaa gcgcttcaac ctgcagcagg cgttcctcaa      3240
tcgtctccag caggccctgg gcgtttaact gaatctggtt catgcgatca cctcgctgac      3300
cgggatacgg gctgacagaa cgaggacaaa acggctggcg aactggcgac gagcttctcg      3360
ctcggatgat gcaatggtgg aaaggcggtg gatatgggat ttttttgtccg tgcggacgac      3420 agctgcaaat ttgaatttga acatggtatg cattcctatc ttgtataggg tgctaccacc      3480
agagttgaga atctctatag gggtggtagc ccagacaggg ttctcaacac cggtacaaga      3540
agaaaccggc ccaaccgaag ttggccccat ctgagccacc ataattcagg tatgcgcaga      3600
tttaacacac aaaaaaacac gctggcgcgt gttgtgcgct tcttgtcatt cggggttgag      3660
aggcccggct gcagattttg ctgcagcggg gtaactctac cgccaaagca gaacgcacgt      3720
caataattta ggtggatatt ttaccccgtg accagtcacg tgcacaggtg tttttatagt      3780
ttgctttact gactgatcag aacctgatca gttattggag tccggtaatc ttattgatga      3840
ccgcagccac cttagatgtt gtctcaaacc ccatacggcc acgaatgagc cactggaacg      3900
gaatagtcag caggtacagc ggaacgaacc acaaacggtt cagacgctgc cagaacgtcg      3960
catcacgacg ttccatccat tcggtattgt cgacgacctg gtaagcgtat tgtcctggcg      4020
tttttgctgc ttccgagtag caatcctctt caccacaaag aaagttactt atctgcttcc      4080
agttttcgaa cccttcttct ttgagccgct tttccagctc attcctccac aaaacaggca      4140
cccatcctct gcgataaatc atgattattt gtcctttaaa taaggctgta gaactgcaaa      4200
atcgctctcg ttcacatgct gtacgtagat gcgtagcaaa ttgccgttcc atccctgtaa      4260
tccaccttct ttggaaagat cgtccttgac ctcacgaaga accttatcca atagccctgc      4320
ggcacaagaa attgcctgct ctggatcagc aaattcatat tgattaatag gtgattgcca      4380
cacaccaaaa acaggaatca tcttttcggc taaacgcctc tcctgttctt tcttaatctc      4440
aagttgtaag cggaccagct caccatccat catttttttgt agatcatgcg ccactattca      4500
cccccactgg ccatcagcaa ataaagcttc atactcggac accggcaggc ggcttccacg      4560
gattgaaagg tcaagccaac cacgtccaga tgggtcagcc ttatccgatt cttcccaccg      4620
ttctgcagct gtagcaacca ggcattctac cgccttcatg tagtcttctg tacggaacca      4680
gccgtagtta atgccaccat cagtaactgc ccaggccatc ttttctctt cggcctcaat      4740
```

```
agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
tcactatctg agaacccgtt catccgaatg atcgtgaatg gaagttcccg gccagtttta   4980
taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct ttcagcagcc ttatttcgcg tactgatagc aggtccataa   5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtggggc gtccggaacg tgctctgttt   5340
tggatcgagg gttaccatgt atatctatat ttagatccaa atcgcgatcc acttcgatgg   5400
tggttttttc caccttacgt gcgtgaattg ataaaccggc ctcgcggcgc ttctccacga   5460
tattcatgag gaactcgacc gagtcccggt caatggaacg catcgtgggg cgtgcatcgc   5520
cgtctctggc gcgtctggtc ttactggata gccccataga ctccaggatg cctatgcaga   5580
ggtctgcagg cgctttcttc ttgccttcct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggttttg gatcgatacc gcagtcgcgg aagtactgct   5760
gcagcgtcgc cgatttgagg gtgtagaaac cacgcatgcc tatctcaaca gcaggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact ttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatgcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccca ttcagccagg tcaacaagca gatcgttggc atcggcatcc accataatgg   7080
catgctcttc agtacgcgcc agcgcgtcga taagcgtgtt gaatacgcct accgggtttt   7140
```

```
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gccttcccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacaggtcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg ccttttcctt   8040
cagctgagga tttgcggtcg ttatcgagag cgcaagtgat ttgcgcagcc gggtacatgt   8100
tcaccagctg ctcgacaacg tgaatcatgt tgttagcgga aaccgcaatg actaccgcgt   8160
caaagcgttt tttcggtcg tttctggtcg ccagccagat ggatgccccg gtggcgaaac   8220
cctctgcagt cgcaattttt tgcgcccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acgcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggcctttaa ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
caagcagtga aaacggatcg ctgccaaagc gctccgcgta gaattcttgt aaggtcattt   9060
tttagccttt ccatgcgaat tagcattttt tcgggttgaa aaaatccgca ggagcagcca   9120
caataaacgc actatctttc tgaaggacgt atctgcgtta tcgtggctac ttcctgaaaa   9180
aggcccgagt ttgccgactc gggttttttt tcgtctttt tcggctgcta cggtctggtt   9240
caaccccgac aaagtataga tcggattaaa ccagaattat agtcagcaat aaaccctgtt   9300
attgtatcat ctaccctcaa ccatgaacga tttgatcgta ccgactactt ggtgcacaaa   9360
ttgaagatca ctttatcat ggataacccg ttgagagtta gcactatcaa ggtagtaatg   9420
ctgctcgtca taacgggcta atcgttgaat tgtgatctcg ccgttattat cacaaaccag   9480
```

```
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900
catacccttta atcataaatg atctctttat agctggctat aattttttata aattataccct    9960
agctttaatt ttcacttatt gattataata atccccatga aacccgaaga acttgtgcgc   10020
catttcggcg atgtggaaaa agcagcggtt ggcgtgggcg tgacaccggg cgcagtctat   10080
caatggctgc aagctgggga gattccacct ctacgacaaa gcgatataga ggtccgtacc   10140
gcgtacaaat taagagtga tttcacctct cagcgcatgg gtaaggaagg gcataacagg    10200
ggatcctcta gagtcgacct gcaggcatgc aagcttcctg aatcgcccca tcatccagcc   10260
agaaagtgag ggagccacgg ttgatgagag cttttgttgta ggtggaccag ttggtgattt   10320
tgaactttg ctttgccacg gaacggtctg cgttgtcggg aagatgcgtg atctgatcct    10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tatcaggatt atcaatacca tattttttgaa aaagccgttt   10560
ctgtaatgaa ggagaaaact caccgaggca gttccatagg atggcaagat cctggtatcg   10620
gtctgcgatt ccgactcgtc caacatcaat acaacctatt aatttcccct cgtcaaaaat   10680
aaggttatca agtgagaaat caccatgagt gacgactgaa tccggtgaga atggcaaaag   10740
cttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat tacaaacagg aatcgaatgc aaccggcgca ggaacactgc   10920
cagcgcatca acaatatttt cacctgaatc aggatattct tctaataacct ggaatgctgt   10980
tttccctggg atcgcagtgg tgagtaacca tgcatcatca ggagtacgga taaaatgctt   11040
gatggtcgga gaggcataa attccgtcag ccagtttagt ctgaccatct catctgtaac   11100
atcattggca acgctacctt tgccatgttt cagaaacaac tctggcgcat cgggcttccc   11160
atacaatcga tagattgtcg cacctgattg cccgacatta tcgcgagccc atttataccc   11220
atataaatca gcatccatgt tggaattttaa tcgcggcctc gagcaagacg tttcccgttg   11280
aatatggctc ataacacccc ttgtattact gtttatgtaa gcagacagtt ttattgttca   11340
tgatgatata tttttatctt gtgcaatgta acatcagaga ttttgagaca caacgtggct   11400
ttgttgaata aatcgaactt tgctgagtt gaaggatcag atcacgcatc ttcccgacaa   11460
cgcagaccgt tccgtggcaa agcaaaagtt caaaatcacc aactggtcca cctacaacaa   11520
agctctcatc aaccgtggct ccctcacttt ctggctggat gatgggggcga ttcaggaagc   11580
ttgcatgcct gcaggtcgac tctagaggat ccccagaaac ccgataatcg ctaccagtga   11640
tgatggctgt tttgcggcgg cgtgagccat cggcaatttc gataatgcct gacgtccttc   11700
tggcgaacgc ggggtctgc tgtcctgaag tgaggaatga agggataagg tcggccagcg   11760
ctgattcgtt cagcaattcc tgatcacgtt cattaccgag ccaaaccatt gtggcctttt   11820
cgactttatc agcaggaatg gtttccagct taaaagtcac gttgcggcca tcaagcttga   11880
```

```
attcgtacgc agaaaggccc acccgaaggt gagccagtgt gattacattt gcggccgcat   11940
ttaaatgggc ccaatggccc gggaggccta cttaagtaag ccggcttagc tagcgggaca   12000
ggtttcccga ctggaaagcg ggcagtgagc gcaacgcaat taatgtgagt tagctcactc   12060
attaggcacc ccaggcttta cactttatgc ttccggctcg tatgttgtgt ggaattgtga   12120
gcggacaaca atttcacaca ggaaacagct atgaccatga ttacgccaag ctatttaggt   12180
gagactatag aatactcaag cttgcatgcg atacgtatcg ttaacgatgg atccgacgca   12240
cgtgcgaatt cgccctatag tgagtcgtat tacaattcac tggccgtcgt tttacaacgt   12300
cgtgactggg aaaaccctgg cgtcacccaa cttaatcgcc ttgcagcaca tccccctttc   12360
gccagctggc gtaatagcga agaggcccgc accgatcgcc cttcccaaca gttgcgcagc   12420
tgaatggcga atggcgcctg agctagcatt gccggcattc ttaagtaggc ctcccgggcc   12480
attggcgcgc catgcggccg ccatggtcaa ataaaacgaa aggctcagtc gaaagactgg   12540
gcctttcgtt ttaatctgat cggcacgtaa gaggttccaa cttTcaccat aatgaaataa   12600
gatcactacc gggcgtattt tttgagttat cgagattttc aggagctaag gaagctaaaa   12660
tgagtattca acatttccgt gtcgccctta ttccctttttt gcggcatttt gccttcctg   12720 ttTttgctca cccagaaacg ctggtgaaag taaaagatgc tgaagatcag ttgggtgcac   12780
gagtgggtta catcgaactg gatctcaaca gcggtaagat ccttgagagt ttacgccccg   12840
aagaacgttt tccaatgatg agcactttta aagttctgct atgtggcgcg gtattatccc   12900
gtattgacgc cgggcaagag caactcggtc gccgcataca ctattctcag aatgacttgg   12960
ttgagtactc accagtcaca gaaaagcatc tcacggatgg catgacagta agagaattat   13020
gcagtgctgc cataaccatg agtgataaca ctgcggccaa cttacttctg caacgatcg   13080 gaggaccgaa ggagctaacc gcttttttgc acaacatggg ggatcatgta actcgccttg   13140
atcgttggga accggagctg aatgaagcca taccaaacga cgagcgtgac accacgatgc   13200
ctgtagcaat ggcaacaacg ttgcgcaaac tattaactgg cgaactactt actctagctt   13260
cccggcaaca attaatagac tggatggagg cggataaagt tgcaggatca cttctgcgct   13320 cggcccctccc ggctggctgg tttattgctg ataaatctgg agccggtgag cgtgggtctc   13380
gcggtatcat tgcagcactg gggccagatg gtaagccctc ccgcatcgta gttatctaca   13440
cgacggggag tcaggcaact atggatgaac gaaatagaca gatcgctgag ataggtgcct   13500
cactgattaa gcattggtaa tgacagaagt caaaagcctc cggtcggagg cttttgactt   13560
tctgctagat ctgtttcaat gcggtgaagg gccaggcagc tggggattat gtcgagaccc   13620
ggccagcatg ttggtttat cgcatattca gcgttgtcgc gtttacccag gtaaaatgga   13680
agcagtgtat cgtctgcgtg aatgtgcaaa tcaggaacgt aaccgtggta catagatgca   13740
gtcccttgcg ggtcgttccc ttcaacgagt aggacgcggt gcccttgcaa ggctaaccat   13800
tgcgcctggt gtactgcaga tgaggtttta taaacccctc ccttgtgtga cataacggaa   13860
agtacaaccg ggttttatc gtcaggtctt tggtttgggt taccaaacac actccgcata   13920
tggctaattt ggtcaattgt gtagccagcg cgacgttcta ctcggcccct catctcaaaa   13980
tcaggagccg gtagacgacc agcttttttcc gcgtctctga tagcctgcgg tgttacgccg   14040
atcaggtctg caacttctgt tatacccag cggcgagtaa tacgacgcgc ttccgggctg   14100
tcatcgccga actgtgcgat ggcaatagcg cgcgtcattt cctgaccgcg attgatacag   14160
tctttcagca aattaattaa cgacatcctg tttcctctca acatgccct tatctttgtg   14220
```

```
tttttcatca tactttacgt ttttaaagca aagcaacata aaaaaagcaa agtgacttag   14280
aaaacgcaaa gttaaggttc aaatcaattt tttgatgcgc tacagaagct atttagcttc   14340
atctaagcgc aacggtatta cttacgttgg tatatttaaa acctaactta atgattttaa   14400
atgataataa atcataccaa ttgctatcaa aagttaagcg aacatgctga ttttcacgct   14460
gtttatacac tttgaggcat ctctatctct tccgtctcta tattgaaaca caatcaaaga   14520
acatcaatcc atgtgacatc ccccactatc taagaacacc ataacagaac acaacatagg   14580
aatgcaacat taatgtatca ataattcgga acatatgcac tatatcatat ctcaattacg   14640
gaacatatca gcacacaatt gcccattata cgc                                14673

<210> SEQ ID NO 5
<211> LENGTH: 14744
<212> TYPE: DNA
<213> ORGANISM: Artificial Sequence
<220> FEATURE:
<223> OTHER INFORMATION: Vector NZAhd

<400> SEQUENCE: 5
gcgtataatg gactattgtg tgctgataag gagaacataa gcgcagaaca atatgtatct     60
attccggtgt tgtgttcctt tgttattctg ctattatgtt ctcttatagt gtgacgaaag    120
cagcataatt aatcgtcact tgttctttga ttgtgttacg atatccagag acttagaaac    180
gggggaaccg ggatgagcaa ggtaaaaatc ggtgagttga tcaacacgct tgtgaatgag    240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta ataaattatc ggaaaagtat    480
cctctttaca gcgaagaatt atcttcatgg cttttctatgc ctacggctaa tattcgccag    540
cacatgtcat cgttacaatc taaattgaaa gaaataatgc cgcttgccga agagttatca    600
aatgtaagaa taggctctaa aggcagtgat gcaaaaatag caagactaat aaaaaaatat    660
ccagattgga gttttgctct tagtgattta aacagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct gcgcgagaag aagcgtaatg ttgtggttat tgactaccca    900
acatacatgc agtctatcta tgatattttg aataatcctg cgactttatt tagttttaaac   960 actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaacgctc tgaagataaa agcgtaacca gaacgattta tactttatgc   1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat catttttcgg cgatgaccgt   1320
cgtgtttata agatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaacacc aggctggtgg ctctgcagaa actggacgat   1560
gaaatgccag gctttgccag aggtgacgct ggcgtccgtc tccatgaaac cgttaagcag   1620
```

```
ctggtggagc aggacccatc agcaaaaata accaacagca ctctccgggc ctttaaattt      1680
agcccgacga tgattagccg gtacctggag tttgccgctg atgcattggg gcagttcgtt      1740
ggcgagaacg ggcagtggca gctgaagata gagacacctg caatcgtcct gcctgatgaa      1800
gaatccgttg agaccatcga cgaaccggat gatgagtccc aagacgacga gctggatgaa      1860
gatgaaattg agctcgacga gggtggcggc gatgaaccaa ccgaagagga agggccagaa      1920
gaacatcagc caactgctct aaaacccgtc ttcaagcctg caaaaaataa cggggacgga      1980
acgtacaaga tagagtttga atacgatgga aagcattatg cctggtccgg ccccgccgat      2040
agccctatgg ccgcaatgcg atccgcatgg gaaacgtact acagctaaaa gaaaagccac      2100
cggtgttaat cggtggcttt tttattgagg cctgtcccta cccatcccct gcaagggacg      2160
gaaggattag gcggaaactg cagctgcaac tacggacatc gccgtcccga ctgcagggac      2220
ttccccgcgt aaagcggggc ttaaattcgg gctggccaac cctattttc tgcaatcgct      2280 ggcgatgtta gttcgtggaa tagcgtttcc agcttttcaa tggccagctc aaaatgtgct      2340
ggcagcacct tctccagttc cgtatcaata tcggtgatcg gcagctctcc acaagacata      2400
ctccggcgac cgccacgaac tacatcgcgc agcagctccc gttcgtagac acgcatgttg      2460
cccagagccg tttctgcagc cgttaatatc cggcgcagct cggcgatgat tgccgggaga      2520
tcatccacgg ttattgggtt cggtgatggg ttcctgcagg gcggcggag agccatccag       2580 acgccgctaa cccatgcgtt acggtactga aaactttgtg ctatgtcgtt tatcaggccc      2640
cgaagttctt cttctgccg ccagtccagt ggttcaccgg cgttcttagg ctcaggctcg        2700
acaaaagcat actcgccgtt tttccggata gctggcagaa cctcgttcgt cacccacttg      2760
cggaaccgcc aggctgtcgt ccctgtttc accgcgtcgc ggcagcggag gattatggtg       2820
tagagaccag attccgatac cacatttact tccctggcca tccgatcaag ttttgtgcc       2880 tcggttaaac cgagggtcaa ttttcatca tgatccagct tacgcaatgc atcagaaggg      2940
ttggctatat tcaatgcagc acagatatcc agcgccacaa accacgggtc accaccgaca      3000
agaaccaccc gtataggtg gctttcctga aatgaaaaga cggagagagc cttcattgcg       3060
cctccccgga tttcagctgc tcagaaaggg acagggagca gccgcgagct tcctgcgtga      3120
gttcgcgcgc gacctgcaga agttccgcag cttcctgcaa atacagcgtg gcctcataac      3180
tggagatagt gcggtgagca gagcccacaa gcgcttcaac ctgcagcagg cgttcctcaa      3240
tcgtctccag caggccctgg gcgtttaact gaatctggtt catgcgatca cctcgctgac      3300
cgggatacgg gctgacagaa cgaggacaaa acggctggcg aactggcgac gagcttctcg      3360
ctcggatgat gcaatggtgg aaaggcggtg gatatgggat tttttgtccg tgcggacgac      3420
agctgcaaat ttgaatttga acatggtatg cattcctatc ttgtataggg tgctaccacc      3480
agagttgaga atctctatag gggtggtagc ccagacaggg ttctcaacac cggtacaaga      3540
agaaaccggc ccaaccgaag ttggccccat ctgagccacc ataattcagg tatgcgcaga      3600
tttaacacac aaaaaaacac gctggcgcgt gttgtgcgct tcttgtcatt cggggttgag      3660
aggcccggct gcagattttg ctgcagcggg gtaactctac cgccaaagca gaacgcacgt      3720
caataattta ggtggatatt ttaccccgtg accagtcacg tgcacaggtg tttttatagt      3780
ttgctttact gactgatcag aacctgatca gttattggag tccggtaatc ttattgatga      3840
ccgcagccac cttagatgtt gtctcaaacc ccatacggcc acgaatgagc cactggaacg      3900
gaatagtcag caggtacagc ggaacgaacc acaaacggtt cagacgctgc cagaacgtcg      3960
```

```
catcacgacg ttccatccat tcggtattgt cgacgacctg gtaagcgtat tgtcctggcg    4020 ttttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat    4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcagggtcg    5820 atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact tttttcaggc cgccgtcgaa atagaatttt aacgccacct    6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggcctatagg cgcgacctga tagccatcat    6300
catgcatgat gcaaatcatg ttgctggcat aatcatttct ggccgatgcc tcgagcgcgg    6360
```

```
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatgcg tcgctgggga    6600 ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900 gattttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agccttttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg cgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgcccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt tttaaatca ttaacgcgtt gttgttcagc tcggaggcgg cgtgcttcag    8640
cctggcgctc catgcgtgca cgttcttctt ccggctgagc gaccacggtc gcaccattcc    8700
```

```
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggttttttt tcgtcttttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca ctttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccttta atcataaatg atctctttat agctggctat aattttata aattataccct   9960 agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg gcataacagg   10200
ggatcctcta gagtcgacct gcaggcatgc aagcttcctg aatcgcccca tcatccagcc   10260
agaaagtgag ggagccacgg ttgatgagag ctttgttgta ggtggaccag ttggtgattt   10320
tgaacttttg ctttgccacg gaacggtctg cgttgtcggg aagatgcgtg atctgatcct   10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tatcaggatt atcaatacca tatttttgaa aaagccgttt   10560
ctgtaatgaa ggagaaaact caccgaggca gttccatagg atggcaagat cctggtatcg   10620
gtctgcgatt ccgactcgtc caacatcaat acaacctatt aatttcccct cgtcaaaaat   10680
aaggttatca agtgagaaat caccatgagt gacgactgaa tccggtgaga atggcaaaag   10740
cttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat tacaaacagg aatcgaatgc aaccggcgca ggaacactgc   10920
cagcgcatca acaatatttt cacctgaatc aggatattct tctaatacct ggaatgctgt   10980
tttccctggg atcgcagtgg tgagtaacca tgcatcatca ggagtacgga taaaatgctt   11040
gatggtcgga agaggcataa attccgtcag ccagtttagt ctgaccatct catctgtaac   11100
```

```
atcattggca acgctacctt tgccatgttt cagaaacaac tctggcgcat cgggcttccc   11160
atacaatcga tagattgtcg cacctgattg cccgacatta tcgcgagccc atttataccc   11220
atataaatca gcatccatgt tggaatttaa tcgcggcctc gagcaagacg tttcccgttg   11280
aatatggctc ataacacccc ttgtattact gtttatgtaa gcagacagtt ttattgttca   11340
tgatgatata tttttatctt gtgcaatgta acatcagaga ttttgagaca caacgtggct   11400
ttgttgaata aatcgaactt ttgctgagtt gaaggatcag atcacgcatc ttcccgacaa   11460
cgcagaccgt tccgtggcaa agcaaaagtt caaaatcacc aactggtcca cctacaacaa   11520
agctctcatc aaccgtggct ccctcacttt ctggctggat gatggggcga ttcaggaagc   11580
ttgcatgcct gcaggtcgac tctagaggat ccccgagaac ccgataatcg ctaccagtga   11640
tgatggctgt tttgcggcgg cgtgagccat cggcaatttc gataatgcct gacgtccttc   11700
tggcgaacgc ggggttctgc tgtcctgaag tgaggaatga agggataagg tcggccagcg   11760
ctgattcgtt cagcaattcc tgatcacgtt cattaccgag ccaaaccatt gtggcctttt   11820
cgactttatc agcaggaatg gtttccagct taaaagtcac gttgcggcca tcaagcttga   11880
attcgtacgc agaaaggccc acccgaaggt gagccagtgt gattacattt gcggccagtc   11940
cagttacgct ggagtcacta gtgcggccgc gacaacttgt ctagggccca atggcccggg   12000
aggcctactt aagtaagccg gcttagctag cgggacaggt ttcccgactg gaaagcgggc   12060
agtgagcgca acgcaattaa tgtgagttag ctcactcatt aggcacccca ggctttacac   12120
tttatgcttc cggctcgtat gttgtgtgga attgtgagcg acaacaatt tcacacagga   12180 aacagctatg accatgatta cgccaagcta tttaggtgag actatagaat actcaagctt   12240
gcatgcgata cgtatcgtta acgatggatc cgacgcacgt gcgaattcgc cctatagtga   12300
gtcgtattac aattcactgg ccgtcgtttt acaacgtcgt gactgggaaa accctggcgt   12360
cacccaactt aatcgccttg cagcacatcc ccctttcgcc agctggcgta atagcgaaga   12420
ggcccgcacc gatcgccctt cccaacagtt gcgcagctga atggcgaatg gcgcctgagc   12480
tagcattgcc ggcattctta agtaggcctc ccgggccatt ggcgcgccat gacttgaagt   12540
cgcggccgca ctgaccattt aaatcatacc aacatggtca aataaaacga aggctcagt    12600 cgaaagactg ggcctttcgt tttaatctga tcggcacgta agaggttcca actttcacca   12660
taatgaaata agatcactac cgggcgtatt ttttgagtta tcgagatttt caggagctaa   12720
ggaagctaaa atgagtattc aacatttccg tgtcgccctt attccctttt ttgcggcatt   12780
ttgccttcct gtttttgctc acccagaaac gctggtgaaa gtaaaagatg ctgaagatca   12840
gttgggtgca cgagtgggtt acatcgaact ggatctcaac agcggtaaga tccttgagag   12900
tttacgcccc gaagaacgtt ttccaatgat gagcactttt aaagttctgc tatgtggcgc   12960
ggtattatcc cgtattgacg ccgggcaaga gcaactcggt cgccgcatac actattctca   13020
gaatgacttg gttgagtact caccagtcac agaaaagcat ctcacggatg catgacagt    13080 aagagaatta tgcagtgctg ccataaccat gagtgataac actgcggcca acttacttct   13140
ggcaacgatc ggaggaccga aggagctaac cgcttttttg cacaacatgg ggatcatgt    13200 aactcgcctt gatcgttggg aaccggagct gaatgaagcc ataccaaacg acgagcgtga   13260
caccacgatg cctgtagcaa tggcaacaac gttgcgcaaa ctattaactg gcgaactact   13320
tactctagct tcccggcaac aattaataga ctggatggag gcggataaag ttgcaggatc   13380
acttctgcgc tcggcccctcc cggctggctg gtttattgct gataaatctg gagccggtga   13440
```

```
gcgtgggtct cgcggtatca ttgcagcact ggggccagat ggtaagccct cccgcatcgt    13500
agttatctac acgacgggga gtcaggcaac tatggatgaa cgaaatagac agatcgctga    13560
gataggtgcc tcactgatta agcattggta atgacagaag tcaaaagcct ccggtcggag    13620
gcttttgact ttctgctaga tctgtttcaa tgccgtgaag gccaggcag ctggggatta     13680 tgtcgagacc cggccagcat gttggtttta tcgcatattc agcgttgtcg cgtttaccca    13740
ggtaaaatgg aagcagtgta tcgtctgcgt gaatgtgcaa atcaggaacg taaccgtggt    13800
acatagatgc agtcccttgc gggtcgttcc cttcaacgag taggacgcgg tgcccttgca    13860
aggctaacca ttgcgcctgg tgtactgcag atgaggtttt ataaaccct cccttgtgtg     13920 acataacgga aagtacaacc gggttttat cgtcaggtct ttggtttggg ttaccaaaca     13980
cactccgcat atggctaatt tggtcaattg tgtagccagc gcgacgttct actcggcccc    14040
tcatctcaaa atcaggagcc ggtagacgac cagcttttc cgcgtctctg atagcctgcg     14100
gtgttacgcc gatcaggtct gcaacttctg ttataccca gcggcgagta atacgacgcg     14160
cttccgggct gtcatcgccg aactgtgcga tgcaatagc gcgcgtcatt tcctgaccgc     14220
gattgataca gtctttcagc aaattaatta acgacatcct gtttcctctc aaacatgccc    14280
ttatctttgt gttttcatc atactttacg tttttaaagc aaagcaacat aaaaaaagca     14340
aagtgactta gaaaacgcaa agttaaggtt caaatcaatt ttttgatgcg ctacagaagc    14400
tatttagctt catctaagcg caacggtatt acttacgttg gtatatttaa aacctaactt    14460
aatgatttta aatgataata aatcatacca attgctatca aaagttaagc gaacatgctg    14520
attttcacgc tgtttataca ctttgaggca tctctatctc ttccgtctct atattgaaac    14580
acaatcaaag aacatcaatc catgtgacat ccccactat ctaagaacac cataacagaa      14640
cacaacatag gaatgcaaca ttaatgtatc aataattcgg aacatatgca ctatatcata    14700
tctcaattac ggaacatatc agcacacaat tgcccattat acgc                     14744

<210> SEQ ID NO 6
<211> LENGTH: 14549
<212> TYPE: DNA
<213> ORGANISM: Artificial Sequence
<220> FEATURE:
<223> OTHER INFORMATION: Vector NZCK3

<400> SEQUENCE: 6
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaagga     360
ttgcagaaaa gaataaccgc gaatacttttt aacgcctata tgagcagggc aagaaagcgg    420
tttgatgata aattacatca tagctttgat aaaaatatta ataaattatc ggaaaagtat     480
cctctttaca gcgaagaatt atcttcatgg ctttctatgc ctacggctaa tattcgccag    540
cacatgtcat cgttacaatc taaattgaaa gaaataatgc cgcttgccga agagttatca     600
aatgtaagaa taggctctaa aggcagtgat gcaaaaatag caagactaat aaaaaaatat    660
ccagattgga gttttgctct tagtgattta aacagtgatg attggaagga gcgccgtgac    720
tatctttata agttattcca acaaggctct gcgttgttag aagaactaca ccagctcaag    780
```

```
gtcaaccatg aggttctgta ccatctgcag ctaagccctg cggagcgtac atctatacag    840
caacgatggg ccgatgttct gcgcgagaag aagcgtaatt ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaacgctc tgaagataaa agcgtaacca gaacgattta tactttatgc    1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat cattttttcgg cgatgaccgt   1320 cgtgtttata aagatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcggggc ttaaattcgg gctggccaac cctattttc tgcaatcgct   2280 ggcgatgtta gtttcgtgga tagcgttttc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt ccctgtttc accgcgtcgc ggcagcggag gattatggtg   2820
tagagaccag attccgatac cacatttact tccctggcca tccgatcaag ttttttgtgcc   2880 tcggttaaac cgagggtcaa ttttttcatca tgatccagct tacgcaatgc atcagaaggg   2940
ttggctatat tcaatgcagc acagatatcc agcgccacaa accacgggtc accaccgaca   3000
agaaccaccc gtatagggtg cctttcctga aatgaaaaga cggagagagc cttcattgcg   3060
cctccccgga tttcagctgc tcagaaaggg acagggagca gccgcgagct tcctgcgtga   3120
```

```
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
ttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttgt agatcatgcg ccactattca    4500
ccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat    4740
agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt    5340
tggatcgagg gttaccatgt atatctatat ttagatccaa atcgcgatcc acttcgatgg    5400
tggttttttc cacccttacgt gcgtgaattg ataaaccggc ctcgcggcgc ttctccacga    5460
tattcatgag gaactcgacc gagtccgggt caatggaacg catcgtgggg cgtgcatcgc    5520
```

```
cgtctctggc gcgtctggtc ttactggata gccccataga ctccaggatg cctatgcaga   5580
ggtctgcagg cgctttcttc ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcaggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggctttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatgcg tcgctgggga    6600 ccacttcgcc gcagaacatg ccgaaatggc ggtggaagtg tttctcctca atcgatacac   6660
ctgaagatat cgacgggctg tagatgaggc cgtcatattt tttccaccatc actttaggct  6720 ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gccagctcc tcgcgtcgct    7020 tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gcctttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccgcgcgta atgtgatctt taacggtacc gttataaatt tctgcgatac    7680
ccatatcccg cagcgtgctg cttaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacagatcg gttgcacggc   7860
```

```
tcagatgatt tctcgttaat ctggcgagcg acttccttca gccctctcag gctgtgcagg    7920
tcgttaaaat cgctgcattc cagctcaggg tcatcctcaa aagttgggta aacacattgg    7980
acgccggaaa acttctccat gatgtcgaat ccggtgcgga ggcctgtgtt gccttttcct    8040
tcagctgagg atttgcggtc gttatcgaga gcgcaagtga tttgcgcagc cgggtacatg    8100
ttcaccagct gctcgacaac gtgaatcatg ttgttagcgg aaaccgcaat gactaccgcg    8160
tcaaagcgtt ttttcgggtc gtttctggtc gccagccaga tggatgcccc ggtggcgaaa    8220
ccctctgcag tcgcaatttt ttgcgccccc tgcaggtcgc caataacaaa gcatgcaccg    8280
acgaaatcac cgttagtgat ggcgctggtc tggaacttgc caccattcag atcgatacgt    8340
tgccagccaa caatccgccc gtcttttctt ccgtccaggt gggacagagg tatcgccatg    8400
taagttgttg gtccacggct ccatttcgca ctgtcgtgac tggtcacgcg acgtatatca    8460
caagcgccaa atacgtcacg aattcccttt tttaccgcat aaggccagga gccatcttca    8520
gctggcgaat gttcccaggc gcgatggaaa gccaaccatc caagcaggcg ttcctgctcc    8580
atctgattgt ttttaaatc attaacgcgt tgttgttcag ctcggaggcg gcgtgcttca    8640
gcctggcgct ccatgcgtgc acgttcttct ccggctgag cgaccacggt cgcaccattc    8700
cgttgctgtt cacggcgata ctccgaaaac aggaatgaaa agccactcca ggagccagcg    8760
tcatgcgctt tttcaacgaa gttaacgaaa ggataactga tgccatcctt gctctgctca    8820
aggcgtgaat agatttccac acggccttta aggctcttct gcagagcttc cggggaggaa    8880
ttattgtagg tggtatagcg ctctacacca ccgcgcggat tgagctgaat cttatcagca    8940
cacgcaggcc agttgatacc ggccatcttc gccagctcag tcagctcatc acgtgccgcg    9000
tcaagcagtg aaaacggatc gctgccaaag cgctccgcgt agaattcttg taaggtcatt    9060
ttttagcctt tccatgcgaa ttagcatttt ttcgggttga aaaaatccgc aggagcagcc    9120
acaataaacg cactatcttt ctgaaggacg tatctgcgtt atcgtggcta cttcctgaaa    9180
aaggcccgag tttgccgact cgggtttttt ttcgtctttt ttcggctgct acggtctggt    9240
tcaaccccga caaagtatag atcggattaa accagaatta tagtcagcaa taaaccctgt    9300
tattgtatca tctaccctca accatgaacg atttgatcgt accgactact tggtgcacaa    9360
attgaagatc acttttatca tggataaccc gttgagagtt agcactatca aggtagtaat    9420
gctgctcgtc ataacgggct aatcgttgaa ttgtgatctc gccgttatta tcacaaacca    9480
gtacatcctc acccggtaca agcgtaagtg aagaatcgac caggataacg tctcccggct    9540
ggtagtttcg ctgaatctgg ttcccgaccg tcagtgcgta acggtgttc cgttgactca    9600
cgaacggcag gaatcgctct gtgttggcag gttctccagg ctgccagtct ctatccggtc    9660
cggtctctgt cgtaccaata acaggaacgc ggtctggatc agattcagtg ccatacagta    9720
tccattgcac gggcttacgc aggcattttg ccagcgatag cccgatctcc agcgacggca    9780
tcacgtcgcc acgttctaag ttttggacgc ccggaagaga gattcctaca gcttctgcca    9840
cttgcttcag cgtcagtttc agctctaaac ggcgtgcttt cagtcgttcg cctcgtgttt    9900
tcatacccctt aatcataaat gatctcttta gctggcta taatttttat aaattatacc    9960
tagctttaat tttcacttat tgattataat aatcccatg aaacccgaag aacttgtgcg   10020
ccatttcggc gatgtggaaa aagcagcggt tggcgtgggc gtgacacccg cgcagtcta    10080
tcaatggctg caagctgggg agattccacc tctacgacaa agcgatatag aggtccgtac    10140
cgcgtacaaa ttaagagtg atttcacctc tcagcgcatg gtaaggaag gcataacag     10200
gggatcctct agagtcgacc tgcaggcatg caagcttcct gaatcgcccc atcatccagc   10260
```

```
cagaaagtga gggagccacg gttgatgaga gctttgttgt aggtggacca gttggtgatt   10320
ttgaactttt gctttgccac ggaacggtct gcgttgtcgg gaagatgcgt gatctgatcc   10380
ttcaactcag caaaagttcg atttattcaa caaagccgcc gtcccgtcaa gtcagcgtaa   10440
tgctctgcca gtgttacaac caattaacca attctgatta gaaaaactca tcgagcatca   10500
aatgaaactg caatttattc atatcaggat tatcaatacc atattttga aaaagccgtt    10560 tctgtaatga aggagaaaac tcaccgaggc agttccatag gatggcaaga tcctggtatc   10620
ggtctgcgat tccgactcgt ccaacatcaa tacaacctat taatttcccc tcgtcaaaaa   10680
taaggttatc aagtgagaaa tcaccatgag tgacgactga atccggtgag aatggcaaaa   10740
gcttatgcat ttctttccag acttgttcaa caggccagcc attacgctcg tcatcaaaat   10800
cactcgcatc aaccaaaccg ttattcattc gtgattgcgc ctgagcgaga cgaaatacgc   10860
gatcgctgtt aaaaggacaa ttacaaacag gaatcgaatg caaccggcgc aggaacactg   10920
ccagcgcatc aacaatattt tcacctgaat caggatattc ttctaatacc tggaatgctg   10980
ttttccctgg gatcgcagtg gtgagtaacc atgcatcatc aggagtacgg ataaaatgct   11040
tgatggtcgg aagaggcata aattccgtca gccagtttag tctgaccatc tcatctgtaa   11100
catcattggc aacgctacct ttgccatgtt tcagaaacaa ctctggcgca tcgggcttcc   11160
catacaatcg atagattgtc gcacctgatt gcccgacatt atcgcgagcc catttatacc   11220
catataaatc agcatccatg ttggaattta atcgcggcct cgagcaagac gtttcccgtt   11280
gaatatggct cataacaccc cttgtattac tgtttatgta agcagacagt tttattgttc   11340
atgatgatat atttttatct tgtgcaatgt aacatcagag attttgagac acaacgtggc   11400
tttgttgaat aaatcgaact tttgctgagt tgaaggatca gatcacgcat cttcccgaca   11460
acgcagaccg ttccgtggca aagcaaaagt tcaaaatcac caactggtcc acctacaaca   11520
aagctctcat caaccgtggc tccctcactt tctggctgga tgatgggcg attcaggaag    11580 cttgcatgcc tgcaggtcga ctctagagga tccccgagaa cccgataatc gctaccagtg   11640
atgatggctg ttttgcggcg gcgtgagcca tcggcaattt cgataatgcc tgacgtcctt   11700
ctggcgaacg cggggttctg ctgtcctgaa gtgaggaatg aagggataag gtcggccagc   11760
gctgattcgt tcagcaattc ctgatcacgt tcattaccga gccaaaccat tgtggccttt   11820
tcgactttat cagcaggaat ggtttccagc ttaaaagtca cgttgcggcc atcaagcttg   11880
aattcgtacg cagaaaggcc cacccgaagg tgagccagtg tgattacatt tgcggccagt   11940
ccagttacgc tggagtcact agtgcggccg cgacaacttg tctagggccc aatgcccgg    12000 gaggcctact taagtaagcc ggcttagcta gcgggacagg tttcccgact ggaaagcggg   12060
cagtgagcgc aacgcaatta atgtgagtta gctcactcat taggcacccc aggctttaca   12120
ctttatgctt ccggctcgta tgttgtgtgg aattgtgagc ggacaacaat ttcacacagg   12180
aaacagctat gaccatgatt acgccaagct atttaggtga gactatagaa tactcaagct   12240
tgcatgcgat acgtatcgtt aacgatggat ccgacgcacg tgcgaattcg ccctatagtg   12300
agtcgtatta caattcactg gccgtcgttt tacaacgtcg tgactgggaa accctggcg    12360 tcacccaact taatcgcctt gcagcacatc ccccttcgc cagctggcgt aatagcgaag    12420
aggcccgcac cgatcgccct tcccaacagt tgcgcagctg aatggcgaat ggcgcctgag   12480
ctagcattgc cggcattctt aagtaggcct cccgggccat tggcgcgcca gacttgaagt   12540
cgcggccgca ctgaccattt aaatcatacc aacatggtca aataaaacga aaggctcagt   12600
```

```
cgaaagactg ggcctttcgt tttaatctga tcggcacgta agaggttcca actttcacca    12660
taatgaaata agatcactac cgggcgtatt ttttgagtta tcgagatttt caggagctaa    12720
ggaagctaaa atggagaaaa aaatcactgg atataccacc gttgatatat cccaatggca    12780
tcgtaaagaa cattttgagg catttcagtc agttgctcaa tgtacctata accagaccgt    12840
tcagctggat attacggcct ttttaaagac cgtaaagaaa aataagcaca gtttttatcc    12900
ggcctttatt cacattcttg cccgcctgat gaatgctcat ccggaatttc gtatggcaat    12960
gaaagacggt gagctggtga tatgggatag tgttcaccct tgttacaccg ttttccatga    13020
gcaaactgaa acgttttcat cgctctggag tgaataccac gacgatttcc ggcagtttct    13080
acacatatat tcgcaagatg tggcgtgtta cggtgaaaac ctggcctatt tccctaaagg    13140
gtttattgag aatatgtttt tcgtctcagc caatccctgg gtgagtttca ccagttttga    13200
tttaaacgtg gccaatatgg acaacttctt cgccccegtt ttcaccatgg gcaaatatta    13260
tacgcaaggc gacaaggtgc tgatgccgct ggcgattcag gttcatcatg ccgtttgtga    13320
tggcttccat gtcggcagaa tgcttaatga attacaacag tactgcgatg agtggcaggg    13380
cggggcgtaa cctaggtgac agaagtcaaa agcctccggt cggaggcttt tgactttctg    13440
ctagatctgt ttcaatgcgg tgaagggcca ggcagctggg gattatgtcg agacccggcc    13500
agcatgttgg ttttatcgca tattcagcgt tgtcgcgttt acccaggtaa aatggaagca    13560
gtgtatcgtc tgcgtgaatg tgcaaatcag gaacgtaacc gtggtacata gatgcagtcc    13620
cttgcgggtc gttcccttca acgagtagga cgcggtgccc ttgcaaggct aaccattgcg    13680
cctggtgtac tgcagatgag gttttataaa cccctccctt gtgtgacata acggaaagta    13740
caaccgggtt tttatcgtca ggtctttggt ttgggttacc aaacacactc cgcatatggc    13800
taatttggtc aattgtgtag ccagcgcgac gttctactcg gccectcatc tcaaaatcag    13860
gagccggtag acgaccagct ttttccgcgt ctctgatagc ctgcggtgtt acgccgatca    13920
ggtctgcaac ttctgttata ccccagcggc gagtaatacg acgcgcttcc gggctgtcat    13980
cgccgaactg tgcgatggca atagcgcgcg tcatttcctg accgcgattg atacagtctt    14040
tcagcaaatt aattaacgac atcctgtttc ctctcaaaca tgcccttatc tttgtgtttt    14100
tcatcatact ttacgttttt aaagcaaagc aacataaaaa aagcaaagtg acttagaaaa    14160
cgcaaagtta aggttcaaat caatttttttg atgcgctaca gaagctattt agcttcatct    14220
aagcgcaacg gtattactta cgttggtata tttaaaacct aacttaatga ttttaaatga    14280
taataaatca taccaattgc tatcaaaagt taagcgaaca tgctgatttt cacgctgttt    14340
atacactttg aggcatctct atctcttccg tctctatatt gaaacacaat caaagaacat    14400
caatccatgt gacatccccc actatctaag aacaccataa cagaacacaa cataggaatg    14460
caacattaat gtatcaataa ttcggaacat atgcactata tcatatctca attacggaac    14520
atatcagcac acaattgccc attatacgc                                      14549
```

<210> SEQ ID NO 7
<211> LENGTH: 12873
<212> TYPE: DNA
<213> ORGANISM: Artificial Sequence
<220> FEATURE:
<223> OTHER INFORMATION: Vector NZTC2

<400> SEQUENCE: 7

```
gcgtataatg gactattgtg tgctgataag gagaacataa gcgcagaaca atatgtatct     60
attccggtgt tgtgttcctt tgttattctg ctattatgtt ctcttatagt gtgacgaaag    120
```

```
cagcataatt aatcgtcact tgttctttga ttgtgttacg atatccagag acttagaaac    180
gggggaaccg ggatgagcaa ggtaaaaatc ggtgagttga tcaacacgct tgtgaatgag    240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta taaattatc ggaaaagtat    480 cctctttaca gcgaagaatt atcttcatgg ctttctatgc ctacggctaa tattcgccag    540
cacatgtcat cgttacaatc taaattgaaa gaataatgc cgcttgccga agagttatca    600
aatgtaagaa taggctctaa aggcagtgat gcaaaaatag caagactaat aaaaaaatat    660
ccagattgga gttttgctct tagtgattta acagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct gcgcgagaag aagcgtaatg ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaacgctc tgaagataaa agcgtaacca gaacgattta tactttatgc   1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat catttttcgg cgatgaccgt   1320 cgtgttata aagatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcggggc ttaaattcgg gctggccaac cctattttc tgcaatcgct   2280 ggcgatgtta gtttcgtgga tagcgttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
```

```
cccagagccg tttctgcagc cgttaatatc cggcgcagct cggcgatgat tgccgggaga    2520
tcatccacgg ttattgggtt cggtgatggg ttcctgcagg cgcggcggag agccatccag    2580
acgccgctaa cccatgcgtt acggtactga aactttgtg ctatgtcgtt tatcaggccc     2640
cgaagttctt cttctgccg ccagtccagt ggttcaccgg cgttcttagg ctcaggctcg     2700
acaaaagcat actcgccgtt tttccggata gctggcagaa cctcgttcgt cacccacttg    2760
cggaaccgcc aggctgtcgt cccctgtttc accgcgtcgc ggcagcggag gattatggtg    2820
tagagaccag attccgatac cacatttact tccctggcca tccgatcaag tttttgtgcc    2880
tcggttaaac cgagggtcaa ttttttcatca tgatccagct tacgcaatgc atcagaaggg   2940
ttggctatat tcaatgcagc acagatatcc agcgccacaa accacgggtc accaccgaca    3000
agaaccaccc gtatagggtg gcttccctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat ttttgtccg tgcggacgac     3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaccggc ccaaccgaag ttggccccat ctgagccacc ataattcagg tatgcgcaga     3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc agaacgtcg     3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtccttttaaa taaggctgta gaactgcaaa   4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat   4740
agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
```

```
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attaccctc cggttatatc gccacggctt     5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtgggc gtccggaacg tgctctgttt     5340
tggatcgagg gttaccatgt atatctatat ttagatccaa atcgcgatcc acttcgatgg    5400 tggtttttc caccttacgt gcgtgaattg ataaaccggc ctcgcggcgc ttctccacga     5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgcttctc ttgcctttct ctgtgttgaa gccgccgatg cgtaaaacgt      5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcaggggtcg    5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact tttttcaggc cgccgtcgaa atagaatttt aacgccacct    6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgatttt tccggatcgg tttcacgttt accgcgaagc ttgtcgaaac     6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900 gattttctc ggtataaaat acgcggatag gcttgttggt ttcgcggttg cgaacgtcga     6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
```

```
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttcccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg ctkaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacaggtcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat tgcgcagcc gggtacatgt     8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaatttt tgcgcccct gcaggtcgcc aataacaaag catgcaccga     8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attcctttt ttaccgcata aggccaggag ccatcttcag     8520
ctggcgaatg ttcccaggcg cgatggaaag ccaaccatcc aagcaggcgt tcctgctcca    8580
tctgattgtt tttaaatca ttaacgcgtt gttgttcagc tcggaggcgg cgtgcttcag     8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt tcaacgaag ttaacgaaag gataactgat gccatccttg ctctgctcaa     8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcatt     9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggttttttt tcgtctttt tcggctgcta cggtctggtt     9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
```

```
gaacggcagg aatcgctctg tgttggcagg ttctccaggc tgccagtctc tatccggtcc   9660
ggtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttgacgcc cggaagagag attcctacag cttctgccac    9840
ttgcttcagc gtcagtttca gctctaaacg gcgtgctttc agtcgttcgc ctcgtgtttt   9900 catacccta atcataaatg atctctttat agctggctat aatttttata aattataccct   9960 agctttaatt ttcacttatt gattataata atccccatga aacccgaaga acttgtgcgc  10020
catttcggcg atgtggaaaa agcagcggtt ggcgtgggcg tgacacccgg cgcagtctat  10080
caatggctgc aagctgggga gattccacct ctacgacaaa gcgatataga ggtccgtacc  10140
gcgtacaaat taaagagtga tttcacctct cagcgcatgg gtaaggaagg cataacagg   10200 ggatcctcta gacgcagaaa ggcccacccg aaggtgagcc agtgtgatta catttgcggc  10260
cagtccagtt acgctggagt cactagtgcg gccgcgacaa cttgtctagg gcccaatggc  10320
ccgggaggcc tacttaagta agccggctta gctagcggga caggtttccc gactggaaag  10380
cgggcagtga gcgcaacgca attaatgtga gttagctcac tcattaggca ccccaggctt  10440
tacactttat gcttccggct cgtatgttgt gtggaattgt gagcggacaa caatttcaca  10500
caggaaacag ctatgaccat gattacgcca agctatttag gtgagactat agaatactca  10560
agcttgcatg cgatacgtat cgttaacgat ggatccgacg cacgtgcgaa ttcgccctat  10620
agtgagtcgt attacaattc actggccgtc gttttacaac gtcgtgactg ggaaaaccct  10680
ggcgtcaccc aacttaatcg ccttgcagca catcccccct tcgccagctg gcgtaatagc  10740
gaagaggccc gcaccgatcg cccttcccaa cagttgcgca gctgaatggc gaatggcgcc  10800
tgagctagca ttgccggcat tcttaagtag gcctcccggg ccattggcgc gccagacttg  10860
aagtcgcggc cgcactgacc atttaaatca taccaacatg gtcaaataaa acgaaaggct  10920
cagtcgaaag actgggcctt tcgttttaat ctgatcggca cgtaagaggt tccaactttc  10980
accataatga aataagatca ctaccgggcg tattttttga gttatcgaga ttttcaggag  11040
ctaaggaagc taaaatggag aaaaaaatca ctggatatac caccgttgat atatcccaat  11100
ggcatcgtaa agaacatttt gaggcatttc agtcagttgc tcaatgtacc tataaccaga  11160
ccgttcagct ggatattacg gcctttttaa agaccgtaaa gaaaaataag cacaagtttt  11220
atccggcctt tattcacatt cttgcccgcc tgatgaatgc tcatccggaa tttcgtatgg  11280
caatgaaaga cggtgagctg gtgatatggg atagtgttca cccttgttac accgttttcc  11340
atgagcaaac tgaaacgttt tcatcgctct ggagtgaata ccacgacgat ttccggcagt  11400
ttctacacat atattcgcaa gatgtggcgt gttacggtga aaacctggcc tatttcccta  11460
aagggtttat tgagaatatg ttttcgtct cagccaatcc ctgggtgagt ttcaccagtt   11520
ttgatttaaa cgtggccaat atggacaact tcttcgcccc cgttttcacc atgggcaaat  11580
attatacgca aggcgacaag gtgctgatgc cgctggcgat tcaggttcat catgccgttt  11640
gtgatggctt ccatgtcggc agaatgctta atgaattaca acagtactgc gatgagtggc  11700
agggcggggc gtaacctagg tgacagaagt caaaagcctc cggtcggagg cttttgactt  11760
tctgctagat ctgtttcaat gcggtgaagg gccaggcagc tggggattat gtcgagaccc  11820
ggccagcatg ttggttttat cgcatattca gcgttgtcgc gtttacccag gtaaaatgga  11880
agcagtgtat cgtctgcgtg aatgtgcaaa tcaggaacgt aaccgtggta catagatgca  11940
```

-continued

```
gtcccttgcg ggtcgttccc ttcaacgagt aggacgcggt gcccttgcaa ggctaaccat    12000
tgcgcctggt gtactgcaga tgaggtttta taaaccccc ccttgtgtga cataacggaa    12060
agtacaaccg ggttttatc gtcaggtctt tggtttgggt taccaaacac actccgcata    12120
tggctaattt ggtcaattgt gtagccagcg cgacgttcta ctcggcccct catctcaaaa    12180
tcaggagccg gtagacgacc agcttttcc gcgtctctga tagcctgcgg tgttacgccg    12240
atcaggtctg caacttctgt tatacccccag cggcgagtaa tacgacgcgc ttccgggctg    12300
tcatcgccga actgtgcgat ggcaatagcg cgcgtcattt cctgaccgcg attgatacag    12360
tctttcagca aattaattaa cgacatcctg tttcctctca aacatgccct tatctttgtg    12420
tttttcatca tactttacgt ttttaaagca aagcaacata aaaaaagcaa agtgacttag    12480
aaaacgcaaa gttaaggttc aaatcaattt tttgatgcgc tacagaagct atttagcttc    12540
atctaagcgc aacggtatta cttacgttgg tatatttaaa acctaactta atgattttaa    12600
atgataataa atcataccaa ttgctatcaa aagttaagcg aacatgctga ttttcacgct    12660
gtttatacac tttgaggcat ctctatctct tccgtctcta tattgaaaca caatcaaaga    12720
acatcaatcc atgtgacatc ccccactatc taagaacacc ataacagaac acaacatagg    12780
aatgcaacat taatgtatca ataattcgga acatatgcac tatatcatat ctcaattacg    12840
gaacatatca gcacacaatt gcccattata cgc                                12873
```

```
<210> SEQ ID NO 8
<211> LENGTH: 22
<212> TYPE: DNA
<213> ORGANISM: Artificial Sequence
<220> FEATURE:
<223> OTHER INFORMATION: Primer T7-RC-Del

<400> SEQUENCE: 8
acgcagaaag gcccacccga ag                                             22

<210> SEQ ID NO 9
<211> LENGTH: 18
<212> TYPE: DNA
<213> ORGANISM: Artificial Sequence
<220> FEATURE:
<223> OTHER INFORMATION: Primer pCmOR

<400> SEQUENCE: 9
tttagcttcc ttagctcc                                                  18

<210> SEQ ID NO 10
<211> LENGTH: 23
<212> TYPE: DNA
<213> ORGANISM: Artificial Sequence
<220> FEATURE:
<223> OTHER INFORMATION: Primer NZg7847a-F2

<400> SEQUENCE: 10
agatcggttg cacggctcag atg                                            23

<210> SEQ ID NO 11
<211> LENGTH: 49
<212> TYPE: DNA
<213> ORGANISM: Artificial Sequence
<220> FEATURE:
<223> OTHER INFORMATION: Primer NZg7847a-F3

<400> SEQUENCE: 11
agatcggttg cacggctcag atgatttctc gttaactggc gagcgactt                49
```

-continued

<210> SEQ ID NO 12
<211> LENGTH: 74
<212> TYPE: DNA
<213> ORGANISM: Artificial Sequence
<220> FEATURE:
<223> OTHER INFORMATION: Primer NZ-RevB

<400> SEQUENCE: 12
gccgcttgac ttcaagtcta atggcccggg aggcctactt aagattcgcc attcagctgc    60
gcaactgttg ggaa                                                      74

<210> SEQ ID NO 13
<211> LENGTH: 74
<212> TYPE: DNA
<213> ORGANISM: Artificial Sequence
<220> FEATURE:
<223> OTHER INFORMATION: Primer NZ-RevA

<400> SEQUENCE: 13
aaatggtcag ttaatcagtt ctatgtacca gcaaggtcca gttgtaagcg gccgcttgac    60
ttcaagtcta atgg                                                      74

<210> SEQ ID NO 14
<211> LENGTH: 22
<212> TYPE: DNA
<213> ORGANISM: Artificial Sequence
<220> FEATURE:
<223> OTHER INFORMATION: Primer NZ-RevC

<400> SEQUENCE: 14
aaatggtcag ttaatcagtt ct                                             22

<210> SEQ ID NO 15
<211> LENGTH: 7260
<212> TYPE: DNA
<213> ORGANISM: Artificial Sequence
<220> FEATURE:
<223> OTHER INFORMATION: Vector pEZ BAC

<400> SEQUENCE: 15
aaggaatatt cagcaatttg cccgtgccga agaaaggccc accgtgaag gtgagccagt    60 gagttgattg ctacgtaaat aacttcgtat agcatacatt atacgaagtt atggactagg   120
cgcgccagaa gagagaaaga aggaaagcgg ccgcacaggt tcccgactg gaaagcgggc   180 agtgagcgca acgcaattaa tgtgagttag ctcactcatt aggcacccca ggctttacac   240
tttatgcttc cggctcgtat gttgtgtgga attgtgagcg ataacaatt tcacacagga   300 aacagctatg accatgatta cgccaagcta tttaggtgag actatagaat actcaagctt   360
gcatgcgata cgtatcgtta acgatggatc cgacgcacgt gcgaattcgc cctatagtga   420
gtcgtattac aattcactgg ccgtcgtttt acaacgtcgt gactgggaaa accctggcgt   480
cacccaactt aatcgccttg cagcacatcc cctttcgcc agctggcgta atagcgaaga   540
ggcccgcacc gatcgccctt ccaacagtt gcgcagctga atggcgaatg gcgcctgatg   600
cggtattttc tccttacggc ggccgcttga cataacttcg tatagcatac attatacgaa   660
gttatgttta acattagca gaaagtcaaa ggcctccggt cggaggcttt tgactaaaac   720
ttcccttggg gttatcattg gccgagacc gcctgaagag gacttccatt gttcattcca   780
cggacaaaaa cagagaaagg aaacgacaga ggccaaaaag ctcgctttca gcacctgtcg   840

```
tttcctttct tttcagaggg tattttaaat aaaaacatta agttatgacg aagaagaacg    900
gaaacgcctt aaaccggaaa attttcataa atagcgaaaa cccgcgaggt cgccgccccg    960
taacctgtcg gatcaccgga aaggacccgt aaagtgataa tgattatcat ctacatatca   1020
caacgtgcgt ggaggccatc aaaccacgtc aaataatcaa ttatgacgca ggtatcgtat   1080
taattgatct gcatcaactt aacgtaaaag caacttcaga caatacaaat cagcgacact   1140
gaatacgggg caacctcatg tcgcctgaag agtgagaccg gccctgatcg gcacgtaaga   1200
ggctccaact ttcaccataa tgaaataaga tcactaccgg gcgtattttt tgagttatcg   1260
agattttcag gagctaagga agctaaaatg gagaaaaaaa tcactggata taccaccgtt   1320
gatatatccc aatggcatcg taaagaacat tttgaggcat ttcagtcagt tgctcaatgt   1380
acctataacc agaccgttca gctggatatt acggcctttt taaagaccgt aaagaaaaat   1440
aagcacaagt tttatccggc ctttattcac attcttgccc gcctgatgaa tgctcatccg   1500
gaatttcgta tggcaatgaa agacggtgag ctggtgatat gggatagtgt tcacccttgt   1560
tacaccgttt tccatgagca aactgaaacg ttttcatcgc tctggagtga ataccacgac   1620
gatttccggc agtttctaca catatattcg caagatgtgg cgtgttacgg tgaaaacctg   1680
gcctatttcc ctaaagggtt tattgagaat atgtttttcg tctcagccaa tccctgggtg   1740
agtttcacca gttttgattt aaacgtggcc aatatggaca acttcttcgc ccccgttttc   1800
accatgggca aatattatac gcaaggcgac aaggtgctga tgccgctggc gattcaggtt   1860
catcatgccg tttgtgatgg cttccatgtc ggcagaatgc ttaatgaatt acaacagtac   1920
tgcgatgagt ggcagggcgg ggcgtaaaaa tgtaatcacc tggctcacct tcgggtgggc   1980
ctttcacact tgcatcggat gcagcccggt gaacgtgccg gcacggcctg ggtaaccagg   2040
tattttgtcc acataaccgt gcgcaaaatg ttgtggataa gcaggacaca gcagcaatcc   2100
acagcaggca tacaaccgca caccgaggtt actccgttct acaggttacg acgacatgtc   2160
aatacttgcc cttgacaggc attgatggaa tcgtagtctc acgctgatag tctgatcgac   2220
aatacaagtg ggaccgtggt cccagaccga taatcagacc gacaacacga gtgggatcgt   2280
ggtcccagac taataatcag accgacgata cgagtgggac cgtggtccca gactaataat   2340
cagaccgacg atacgagtgg gaccgtggtt ccagactaat aatcagaccg acgatacgag   2400
tgggaccgtg gtcccagact aataatcaga ccgacgatac gagtgggacc atggtcccag   2460
actaataatc agaccgacga tacgagtggg accgtggtcc cagtctgatt atcagaccga   2520
cgatacgagt gggaccgtgg tcccagacta ataatcagac cgacgatacg agtgggaccg   2580
tggtcccaga ctaataatca gaccgacgat acgagtggga ccgtggtccc agtctgatta   2640
tcagaccgac gatacaagtg gaacagtggg cccagagaga atattcaggc cagttatgct   2700
ttctggcctg taacaaagga cattaagtaa agacagataa acgtagacta aaacgtggtc   2760
gcatcagggt gctggctttt caagttcctt aagaatggcc tcaatttttct ctatacactc   2820
agttggaaca cgagacctgt ccaggttaag caccatttta tcgcccttat acaatactgt   2880
cgctccagga gcaaactgat gtcgtgagct taaactagtt cttgatgcag atgacgtttt   2940
aagcacagaa gttaaaagag tgataacttc ttcagcttca aatatcaccc cagcttttt    3000
ctgctcatga aggttagatg cctgctgctt aagtaattcc tctttatctg taaaggcttt   3060
ttgaagtgca tcacctgacc gggcagatag ttcaccgggg tgagaaaaaa gagcaacaac   3120
tgatttaggc aatttggcgg tgttgataca gcgggtaata atcttacgtg aaatatttc    3180
cgcatcagcc agcgcagaaa tatttccagc aaattcattc tgcaatcggc ttgcataacg   3240
```

```
ctgaccacgt tcataagcac ttgttgggcg ataatcgtta cccaatctgg ataatgcagc    3300
catctgctca tcatccagct cgccaaccag aacacgataa tcactttcgg taagtgcagc    3360
agctttacga cggcgactcc catcggcaat ttctatgaca ccagatactc ttcgaccgaa    3420
cgccggtgtc tgttgaccag tcagtagaaa agaaggatg agatcatcca gtgcgtcctc     3480
agtaagcagc tcctggtcac gttcattacc tgaccatacc cgagaggtct tctcaacact    3540
atcaccccgg agcacttcaa gagtaaactt cacatcccga ccacatacag gcaaagtaat    3600
ggcattaccg cgagccatta ctcctacgcg cgcaattaac gaatccacca tcggggcagc    3660
tggtgtcgat aacgaagtat cttcaaccgg ttgagtattg agcgtatgtt ttggaataac    3720
aggcgcacgc ttcattatct aatctcccag cgtggtttaa tcagacgatc gaaaatttca    3780
ttgcagacag gttcccaaat agaaagagca tttctccagg caccagttga agagcgttga    3840
tcaatggcct gttcaaaaac agttctcatc cggatctgac ctttaccaac ttcatccgtt    3900
tcacgtacaa catttttag aaccatgctt cccaggcat cccgaatttg ctcctccatc      3960
cacggggact gagagccatt actattgctg tatttggtaa gcaaaatacg tacatcaggc    4020
tcgaaccctt taagatcaac gttcttgagc agatacgaa gcatatcgaa aaactgcagt     4080
gcggaggtgt agtcaaacaa ctcagcaggc gtgggaacaa tcagcacatc agcagcacat    4140
acgacattaa tcgtgccgat acccaggtta ggcgcgctgt caataactat gacatcatag    4200
tcatgagcaa cagtttcaat ggccagtcgg agcatcaggt gtggatcggt gggcagttta    4260
ccttcatcaa atttgcccat taactcagtt tcaatacggt gcagagccag acaggaagga    4320
ataatgtcaa gccccggcca gcaagtgggc tttattgcat aagtgacatc gtccttttcc    4380
ccaagataga aaggcaggag agtgtcttct gcatgaatat gaagatctgg tacccatccg    4440
tgatacattg aggctgttcc ctgggggtcg ttaccttcca cgagcaaaac acgtagcccc    4500
ttcagagcca gatcctgagc aagatgaaca gaaactgagg ttttgtaaac gccaccttta    4560
tgggcagcaa ccccgatcac cggtggaaat acgtcttcag cacgtcgcaa tcgcgtacca    4620
aacacatcac gcatatgatt aatttgttca attgtataac caacacgttg ctcaacccgt    4680
cctcgaattt ccatatccgg gtgcggtagt cgccctgctt tctcggcatc tctgatagcc    4740
tgagaagaaa ccccaactaa atccgctgct tcacctattc tccagcgccg ggttattttc    4800
ctcgcttccg ggctgtcatc attaaactgt gcaatggcga tagccttcgt catttcatga    4860
ccagcgttta tgcactggtt aagtgttttcc atgagtttca ttctgaacat cctttaatca   4920
ttgctttgcg ttttttttatt aaatcttgca atttactgca aagcaacaac aaaatcgcaa   4980
agtcatcaaa aaccgcaaa gttgtttaaa ataagagcaa cactacaaaa ggagataaga    5040
agagcacata cctcagtcac ttattatcac tagcgctcgc cgcagccgtg taaccgagca    5100
tagcgagcga actggcgagg aagcaaagaa gaactgttct gtcagatagc tcttacgctc    5160
agcgcaagaa gaaatatcca ccgtgggaaa aactccaggt agaggtacac acgcggatag    5220
ccaattcaga gtaataaact gtgataatca accctcatca atgatgacga actaaccccc    5280
gatatcaagt cacatgacga agggaaagag aaggaaatca actgtgacaa actgccctca    5340
aatttggctt ccttaaaaat tacagttcaa aaagtatgag aaaatccatg caggctgaag    5400
gaaacagcaa aactgtgaca aattaccctc agtaggtcag aacaaatgtg acgaaccacc    5460
ctcaaatctg tgacagataa ccctcagact atcctgtcgt catggaagtg atatcgcgga    5520
aggaaaatac gatatgagtc gtctggcggc ctttctttt ctcaatgtat gagaggcgca    5580
```

```
ttggagttct gctgttgatc tcattaacac agacctgcag gaagcggcgg cggaagtcag      5640
gcatacgctg gtaactttga ggcagctggt aacgctctat gatccagtcg attttcagag      5700
agacgatgcc tgagccatcc ggcttacgat actgacacag ggattcgtat aaacgcatgg      5760
catacggatt ggtgatttct tttgtttcac taagccgaaa ctgcgtaaac cggttctgta      5820
acccgataaa gaagggaatg agatatgggt tgatatgtac actgtaaagc cctctggatg      5880
gactgtgcgc acgtttgata aaccaaggaa aagattcata gccttttca tcgccggcat       5940 cctcttcagg gcgataaaaa accacttcct tccccgcgaa actcttcaat gcctgccgta      6000
tatccttact ggcttccgca gaggtcaatc cgaatatttc agcatattta gcaacatgga      6060
tctcgcagat accgtcatgt tcctgtaggg tgccatcaga ttttctgatc tggtcaacga      6120
acagatacag catacgtttt tgatcccggg agagactata tgccgcctca gtgaggtcgt      6180
ttgactggac gattcgcggg ctattttac gtttcttgtg attgataacc gctgtttccg       6240
ccatgacaga tccatgtgaa gtgtgacaag ttttagatt gtcacactaa ataaaaaga       6300 gtcaataagc agggataact ttgtgaaaaa acagcttctt ctgagggcaa tttgtcacag      6360
ggttaagggc aatttgtcac agacaggact gtcatttgag ggtgatttgt cacactgaaa      6420
gggcaatttg tcaacacacc ttctctagaa ccagcatgga taaaggccta caaggcgctc      6480 taaaaagaa gatctaaaaa ctataaaaaa aataattata aaaatatccc cgtggataag       6540
tggataaccc caagggaagt ttttcaggc atcgtgtgta agcagaatat ataagtgctg       6600
ttccctggtg cttcctcgct cactcgaccg ggagggttcg agaaggggg gcaccccct        6660 tcggcgtgcg cggtcacgcg cacagggcgc agccctggtt aaaaacaagg tttataaata      6720
ttggtttaaa agcaggttaa aagacaggtt agcggtggcc gaaaaacggg cggaaaccct     6780
tgcaaatgct ggattttctg cctgtggaca gcccctcaaa tgtcaatagg tgcgcccctc      6840
atctgtcagc actctgcccc tcaagtgtca aggatcgcgc ccctcatctg tcagtagtcg      6900 cgccctcaa gtgtcaatac cgcagggcac ttatccccag gcttgtccac atcatctgtg       6960
ggaaactcgc gtaaaatcag gcgttttcgc cgatttgcga ggctggccag ctccacgtcg      7020
ccggccgaaa tcgagcctgc ccctcatctg tcaacgccgc gccgggtgag tcggcccctc      7080
aagtgtcaac gtccgcccct catctgtcag tgagggccaa gttttccgcg aggtatccac      7140
aacgccggcg gccggccgcg gtgtctcgca cacggcttcg acggcgtttc tggcgcgttt      7200
gcagggccat agacggccgc cagcccagcg gcgagggcaa ccagcccggt gagcgtcgga      7260

<210> SEQ ID NO 16
<211> LENGTH: 55
<212> TYPE: DNA
<213> ORGANISM: Artificial Sequence
<220> FEATURE:
<223> OTHER INFORMATION: Primer T7RC NotF

<400> SEQUENCE: 16
acgcagaaag gcccacccga aggtgagcca gtgtgattac atttgcggcc gcatt          55

<210> SEQ ID NO 17
<211> LENGTH: 69
<212> TYPE: DNA
<213> ORGANISM: Artificial Sequence
<220> FEATURE:
<223> OTHER INFORMATION: Primer NSAS-LacZ-F

<400> SEQUENCE: 17
gtgtgattac atttgcggcc gcatttaaat gggcccggga caggtttccc gactggaaag     60
```

```
cgggcagtg                                                                   69

<210> SEQ ID NO 18
<211> LENGTH: 70
<212> TYPE: DNA
<213> ORGANISM: Artificial Sequence
<220> FEATURE:
<223> OTHER INFORMATION: Primer NNASA-LacZ-R

<400> SEQUENCE: 18
cttgttttat ttgaccatgg cggccgcatg gcgcgccatc ccgggccctc aggcgccatt        60
cgccattcag                                                                  70

<210> SEQ ID NO 19
<211> LENGTH: 21
<212> TYPE: DNA
<213> ORGANISM: Artificial Sequence
<220> FEATURE:
<223> OTHER INFORMATION: Primer rrn-Fd

<400> SEQUENCE: 19
tgcggccgcc atggtcaaat a                                                     21

<210> SEQ ID NO 20
<211> LENGTH: 93
<212> TYPE: DNA
<213> ORGANISM: Artificial Sequence
<220> FEATURE:
<223> OTHER INFORMATION: Primer rrn-pCmF2

<400> SEQUENCE: 20
tgcggccgcc atggtcaaat aaaacgaaag gctcagtcga agactgggc ctttcgtttt         60 aatctgatcg gcacgtaaga ggttccaact ttc                                        93

<210> SEQ ID NO 21
<211> LENGTH: 55
<212> TYPE: DNA
<213> ORGANISM: Artificial Sequence
<220> FEATURE:
<223> OTHER INFORMATION: Primer TonAmpR

<400> SEQUENCE: 21
tccgaccgga ggcttttgac ttctgtcatt accaatgctt aatcagtgag gcacc              55

<210> SEQ ID NO 22
<211> LENGTH: 58
<212> TYPE: DNA
<213> ORGANISM: Artificial Sequence
<220> FEATURE:
<223> OTHER INFORMATION: Primer TonB-R

<400> SEQUENCE: 22
ttgaaacaga tctagcagaa agtcaaaagc ctccgaccgg aggcttttga cttctgtc           58

<210> SEQ ID NO 23
<211> LENGTH: 22
<212> TYPE: DNA
<213> ORGANISM: Artificial Sequence
<220> FEATURE:
<223> OTHER INFORMATION: Primer T7del

<400> SEQUENCE: 23
acgcagaaag gcccacccga ag                                                    22
```

<210> SEQ ID NO 24
<211> LENGTH: 87
<212> TYPE: DNA
<213> ORGANISM: Artificial Sequence
<220> FEATURE:
<223> OTHER INFORMATION: Primer TonBR2

<400> SEQUENCE: 24
attgaaacag atctagcaga aagtcaaaag cctccgaccg gaggcttttg acttctgtca     60
ttaccaatgc ttaatcagtg aggcacc                                         87

<210> SEQ ID NO 25
<211> LENGTH: 48
<212> TYPE: DNA
<213> ORGANISM: Artificial Sequence
<220> FEATURE:
<223> OTHER INFORMATION: Primer LacANN-For

<400> SEQUENCE: 25
tacttaagta agccggctta gctagcggga caggtttccc gactggaa                  48

<210> SEQ ID NO 26
<211> LENGTH: 49
<212> TYPE: DNA
<213> ORGANISM: Artificial Sequence
<220> FEATURE:
<223> OTHER INFORMATION: Primer LacANN-Rev

<400> SEQUENCE: 26
acttaagaat gccggcaatg ctagctcagg cgccattcgc cattcagct                 49

<210> SEQ ID NO 27
<211> LENGTH: 47
<212> TYPE: DNA
<213> ORGANISM: Artificial Sequence
<220> FEATURE:
<223> OTHER INFORMATION: Primer LacApSA-For

<400> SEQUENCE: 27
ttatatgggc ccaatggccc gggaggccta cttaagtaag ccggctt                   47

<210> SEQ ID NO 28
<211> LENGTH: 50
<212> TYPE: DNA
<213> ORGANISM: Artificial Sequence
<220> FEATURE:
<223> OTHER INFORMATION: Primer LacAsSA-Rev

<400> SEQUENCE: 28
aatagttggc gcgccaatgg cccgggaggc ctacttaaga atgccggcaa                50

<210> SEQ ID NO 29
<211> LENGTH: 78
<212> TYPE: DNA
<213> ORGANISM: Artificial Sequence
<220> FEATURE:
<223> OTHER INFORMATION: Primer LacE-SL1-F

<400> SEQUENCE: 29
taactgtggc cagtccagtt acgctggagt cactagtgcg gccgcgacaa cttgtctagg     60
gcccaatggc ccgggagg                                                   78

<210> SEQ ID NO 30
<211> LENGTH: 70

```
<212> TYPE: DNA
<213> ORGANISM: Artificial Sequence
<220> FEATURE:
<223> OTHER INFORMATION: Primer LacA SR2-Rev

<400> SEQUENCE: 30
ctaggaacat gttggtatga tttaaatggt cagtgcggcc gcgacttcaa gtctggcgcg    60
ccaatggccc                                                           70

<210> SEQ ID NO 31
<211> LENGTH: 39
<212> TYPE: DNA
<213> ORGANISM: Artificial Sequence
<220> FEATURE:
<223> OTHER INFORMATION: Primer 7847-F2

<400> SEQUENCE: 31
agatcggttg cacggctcag atgatttctc gttaactgg                           39

<210> SEQ ID NO 32
<211> LENGTH: 81
<212> TYPE: DNA
<213> ORGANISM: Artificial Sequence
<220> FEATURE:
<223> OTHER INFORMATION: Primer CamTonB-Rev

<400> SEQUENCE: 32
gaaacagatc tgatctagca gaaagtcaaa agcctccgac cggaggcttt tgacttctgt    60
cacctaggtt acgccccgcc c                                              81

<210> SEQ ID NO 33
<211> LENGTH: 41
<212> TYPE: DNA
<213> ORGANISM: Artificial Sequence
<220> FEATURE:
<223> OTHER INFORMATION: Primer 1

<400> SEQUENCE: 33
ttcttatggc cagggaggcc gctctgggta taagcgtaag g                        41

<210> SEQ ID NO 34
<211> LENGTH: 41
<212> TYPE: DNA
<213> ORGANISM: Artificial Sequence
<220> FEATURE:
<223> OTHER INFORMATION: Primer 2

<400> SEQUENCE: 34
aactagtggc cagggaggcc atcagccagg cgacgaatca g                        41

<210> SEQ ID NO 35
<211> LENGTH: 41
<212> TYPE: DNA
<213> ORGANISM: Artificial Sequence
<220> FEATURE:
<223> OTHER INFORMATION: Primer 3

<400> SEQUENCE: 35
ggacttgggc cacccaggcc ttgtaaatgc agtatggatt g                        41

<210> SEQ ID NO 36
<211> LENGTH: 42
<212> TYPE: DNA
<213> ORGANISM: Artificial Sequence
<220> FEATURE:
```

<223> OTHER INFORMATION: Primer 4

<400> SEQUENCE: 36

| atcctagggc cacccaggcc agatattgga gagttgcacc ag | 42 |

<210> SEQ ID NO 37
<211> LENGTH: 14737
<212> TYPE: DNA
<213> ORGANISM: Artificial Sequence
<220> FEATURE:
<223> OTHER INFORMATION: Vector pNZ-Sfi

<400> SEQUENCE: 37

| gcgtataatg gactattgtg tgctgataag gagaacataa gcgcagaaca atatgtatct | 60 |
| attccggtgt tgtgttcctt tgttattctg ctattatgtt ctcttatagt gtgacgaaag | 120 |
| cagcataatt aatcgtcact tgttctttga ttgtgttacg atatccagag acttagaaac | 180 |
| gggggaaccg ggatgagcaa ggtaaaaatc ggtgagttga tcaacacgct tgtgaatgag | 240 |
| gtagaggcaa ttgatgcctc agaccgccca caaggcgaca aaacgaagag aattaaagcc | 300 |
| gcagccgcac ggtataagaa cgcgttattt aatgataaaa gaaagttccg tgggaaagga | 360 |
| ttgcagaaaa gaataaccgc gaatactttt aacgcctata tgagcagggc aagaaagcgg | 420 |
| tttgatgata aattacatca tagctttgat aaaaatatta ataaattatc ggaaaagtat | 480 |
| cctctttaca gcgaagaatt atcttcatgg ctttctatgc ctacggctaa tattcgccag | 540 |
| cacatgtcat cgttacaatc taaattgaaa gaataatgc cgcttgccga gagttatca | 600 |
| aatgtaagaa taggctctaa aggcagtgat gcaaaaatag caagactaat aaaaaaatat | 660 |
| ccagattgga gttttgctct tagtgattta acagtgatg attggaagga gcgccgtgac | 720 |
| tatctttata agttattcca acaaggctct gcgttgttag aagaactaca ccagctcaag | 780 |
| gtcaaccatg aggttctgta ccatctgcag ctaagccctg cggagcgtac atctatacag | 840 |
| caacgatggg ccgatgttct gcgcgagaag aagcgtaatg ttgtggttat tgactaccca | 900 |
| acatacatgc agtctatcta tgatattttg aataatcctg cgactttatt tagtttaaac | 960 |
| actcgttctg gaatggcacc tttggccttt gctctggctg cggtatcagg gcgaagaatg | 1020 |
| attgagataa tgtttcaggg tgaatttgcc gtttcaggaa agtatacggt taatttctca | 1080 |
| gggcaagcta aaaacgctc tgaagataaa gcgtaacca gaacgattta ctttatgc | 1140 |
| gaagcaaaat tattcgttga attattaaca gaattgcgtt cttgctctgc tgcatctgat | 1200 |
| ttcgatgagg ttgttaaagg atatggaaag gatgatacaa ggtctgagaa cggcaggata | 1260 |
| aatgctattt tagcaaaagc atttaaccct tgggttaaat catttttcgg cgatgaccgt | 1320 |
| cgtgttata agatagccg cgctatttac gctcgcatcg cttatgagat gttcttccgc | 1380 |
| gtcgatccac ggtggaaaaa cgtcgacgag gatgtgttct tcatggagat tctcggacac | 1440 |
| gacgatgaga acacccagct gcactataag cagttcaagc tggccaactt ctccagaacc | 1500 |
| tggcgacctg aagttgggga tgaaacacc aggctggtgg ctctgcagaa actggacgat | 1560 |
| gaaatgccag gctttgccag aggtgacgct ggcgtccgtc tccatgaaac cgttaagcag | 1620 |
| ctggtggagc aggacccatc agcaaaaata accaacagca ctctccgggc ctttaaattt | 1680 |
| agcccgacga tgattagccg gtacctggag tttgccgctg atgcattggg gcagttcgtt | 1740 |
| ggcgagaacg ggcagtggca gctgaagata gagacacctg caatcgtcct gcctgatgaa | 1800 |
| gaatccgttg agaccatcga cgaaccggat gatgagtccc aagacgacga gctggatgaa | 1860 |
| gatgaaattg agctcgacga gggtggcggc gatgaaccaa ccgaagagga agggccagaa | 1920 |

```
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcgggc ttaaattcgg gctggccaac cctattttc tgcaatcgct    2280
ggcgatgtta gtttcgtgga tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt ctttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag ttttgtgcc    2880
tcggttaaac cgagggtcaa ttttcatca tgatccagct tacgcaatgc atcagaaggg    2940
ttggctatat tcaatgcagc acagatatcc agcgccacaa accacgggtc accaccgaca   3000
agaaccaccc gtataggggtg ctttcctga aatgaaaaga cggagagagc cttcattgcg    3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa gcgcttcaac ctgcagcagg cgttcctcaa   3240
tcgtctccag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcaatggtgg aaaggcggtg gatatgggat tttttgtccg tgcggacgac   3420
agctgcaaat ttgaatttga acatggtatg cattcctatc ttgtataggg tgctaccacc   3480
agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc cagaacgtcg   3960
catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtccttaaaa taaggctgta gaactgcaaa   4200
atcgctctcg ttcacatgct gtacgtagat gcgtagcaaa ttgccgttcc atccctgtaa   4260
```

```
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc atactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttctctt cggcctcaat     4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400 tggtttttc caccttacgt gcgtgaattg ataaaccggc ctcgcggcgc ttctccacga     5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgctttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc aggttttttg gatcgatacc gcagtcgcgg aagtactgct    5760
gcagcgtcgc cgatttgagg gtgtagaaac cacgcatgcc tatctcaaca gcagggggtcg   5820 atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttcaggc cgccgtcgaa atagaatttt aacgccacct     6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
```

```
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900 gattttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gccttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
ccatatcccg cagcgtgctg ctgaaaaggc gcataagttc tttcgggctg tttggtaccg   7740
ggcatgtcag catgccaata tcaacggcgc gaagcagttc tttggcaaaa gtgcgtctgt   7800
tcagacgcgg gagagtacgc agcttattca gcgtgatcga caacaggtcg gttgcacggc   7860
tcagatgatt tctcgttaac tggcgagcga cttccttcag ccctctcagg ctgtgcaggt   7920
cgttaaaatc gctgcattcc agctcagggt catcctcaaa agttgggtaa acacatttga   7980
cgccggaaaa cttctccatg atgtcgaatc cggtgcggag gcctgtgttg ccttttcctt   8040
cagctgagga tttgcggtcg ttatcgagag cgcaagtgat ttgcgcagcc gggtacatgt   8100
tcaccagctg ctcgacaacg tgaatcatgt tgttagcgga aaccgcaatg actaccgcgt   8160
caaagcgttt tttcgggtcg tttctggtcg ccagccagat ggatgccccg gtggcgaaac   8220
cctctgcagt cgcaattttt tgcgcccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcgaggcgg cgtgcttcag   8640 cctggcgctc catgcgtgca cgttcttctt ccggctgagc gaccacggtc gcaccattcc   8700
gttgctgttc acggcgatac tccgaaaaca ggaatgaaaa gccactccag gagccagcgt   8760
catgcgcttt ttcaacgaag ttaacgaaag gataactgat gccatccttg ctctgctcaa   8820
ggcgtgaata gatttccaca cggccttaa ggctcttctg cagagcttcc ggggaggaat   8880
tattgtaggt ggtatagcgc tctacaccac cgcgcggatt gagctgaatc ttatcagcac   8940
acgcaggcca gttgataccg gccatcttcg ccagctcagt cagctcatca cgtgccgcgt   9000
```

```
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggtttttt tcgtcttttt tcggctgcta cggtctggtt     9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900 catacccta atcataaatg atctctttat agctggctat aatttttata aattatacct     9960
agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taagagtga tttcacctct cagcgcatgg gtaaggaagg gcataacagg    10200
ggatcctcta gagtcgacct gcaggcatgc aagcttcctg aatcgcccca tcatccagcc   10260
agaaagtgag ggagccacgg ttgatgagag ctttgttgta ggtggaccag ttggtgattt   10320 tgaactttg ctttgccacg gaacggtctg cgttgtcggg aagatgcgtg atctgatcct    10380
tcaactcagc aaaagttcga tttattcaac aaagccgccg tcccgtcaag tcagcgtaat   10440
gctctgccag tgttacaacc aattaaccaa ttctgattag aaaaactcat cgagcatcaa   10500
atgaaactgc aatttattca tatcaggatt atcaatacca tatttttgaa aaagccgttt   10560
ctgtaatgaa ggagaaaact caccgaggca gttccatagg atggcaagat cctggtatcg   10620
gtctgcgatt ccgactcgtc aacatcaat acaacctatt aatttcccct cgtcaaaaat    10680
aaggttatca agtgagaaat caccatgagt gacgactgaa tccggtgaga atggcaaaag   10740
cttatgcatt tctttccaga cttgttcaac aggccagcca ttacgctcgt catcaaaatc   10800
actcgcatca accaaaccgt tattcattcg tgattgcgcc tgagcgagac gaaatacgcg   10860
atcgctgtta aaaggacaat tacaaacagg aatcgaatgc aaccggcgca ggaacactgc   10920
cagcgcatca acaatatttt cacctgaatc aggatattct tctaatacct ggaatgctgt   10980
tttccctggg atcgcagtgg tgagtaacca tgcatcatca ggagtacgga taaaatgctt   11040
gatggtcgga agaggcataa attccgtcag ccagtttagt ctgaccatct catctgtaac   11100
atcattggca acgctacctt tgccatgttt cagaaacaac tctggcgcat cgggcttccc   11160
atacaatcga tagattgtcg cacctgattg cccgacatta tcgcgagccc atttatacccc  11220 atataaatca gcatccatgt tggaatttaa tcgcggcctc gagcaagacg tttcccgttg   11280
aatatggctc ataacacccc ttgtattact gtttatgtaa gcagacagtt ttattgttca   11340
tgatgatata tttttatctt gtgcaatgta acatcagaga ttttgagaca caacgtggct   11400
```

```
ttgttgaata aatcgaactt ttgctgagtt gaaggatcag atcacgcatc ttcccgacaa    11460
cgcagaccgt tccgtggcaa agcaaaagtt caaaatcacc aactggtcca cctacaacaa    11520
agctctcatc aaccgtggct ccctcacttt ctggctggat gatggggcga ttcaggaagc    11580
ttgcatgcct gcaggtcgac tctagaggat ccccgagaac ccgataatcg ctaccagtga    11640
tgatggctgt tttgcggcgg cgtgagccat cggcaatttc gataatgcct gacgtccttc    11700
tggcgaacgc ggggttctgc tgtcctgaag tgaggaatga agggataagg tcggccagcg    11760
ctgattcgtt cagcaattcc tgatcacgtt cattaccgag ccaaaccatt gtggcctttt    11820
cgactttatc agcaggaatg gtttccagct taaaagtcac gttgcggcca tcaagcttga    11880
attcgtacgc agaaaggccc acccgaaggt gagccagtgt gattacattt gcggccagtc    11940
cagttacgct ggagtcacta gtgcggccgc gacaacttgt ctagggccca atggcccggg    12000
aggcctactt aagtaagccg gcttagctag cgggacaggt ttcccgactg gaaagcgggc    12060
agtgagcgca acgcaattaa tgtgagttag ctcactcatt aggcacccca ggctttacac    12120
tttatgcttc cggctcgtat gttgtgtgga attgtgagcg gataacaatt tcacacagga    12180
aacagctatg accatgatta cgccaagcta tttaggtgag actatagaat actcaagctt    12240
gcatgcgata cgtatcgtta acgatggatc cgacgcacgt gcgaattcgc cctatagtga    12300
gtcgtattac aattcactgg ccgtcgtttt acaacgtcgt gactgggaaa accctggcgt    12360
cacccaactt aatcgccttg cagcacatcc ccctttcgcc agctggcgta atagcgaaga    12420
ggcccgcacc gatcgccctt cccaacagtt gcgcagctga atggcgaatg gcgcctgagc    12480
tagctggccc gggtggccca tgccagggcc attggcgcgc catgacttga agtcgcggcc    12540
gcactgacca tttaaatcat accaacatgg tcaaataaaa cgaaaggctc agtcgaaaga    12600
ctgggccttt cgttttaatc tgatcggcac gtaagaggtt ccaactttca ccataatgaa    12660
ataagatcac taccgggcgt attttttgag ttatcgagat tttcaggagc taaggaagct    12720
aaaatgagta ttcaacattt ccgtgtcgcc cttattccct tttttgcggc attttgcctt    12780
cctgtttttg ctcacccaga aacgctggtg aaagtaaaag atgctgaaga tcagttgggt    12840
gcacgagtgg gttacatcga actggatctc aacagcggta agatccttga gagtttacgc    12900
cccgaagaac gttttccaat gatgagcact tttaaagttc tgctatgtgg cgcggtatta    12960
tcccgtattg acgccgggca agagcaactc ggtcgccgca tacactattc tcagaatgac    13020
ttggttgagt actcaccagt cacagaaaag catctcacgg atggcatgac agtaagagaa    13080
ttatgcagtg ctgccataac catgagtgat aacactgcgg ccaacttact tctggcaacg    13140
atcggaggac cgaaggagct aaccgctttt ttgcacaaca tgggggatca tgtaactcgc    13200
cttgatcgtt gggaaccgga gctgaatgaa gccataccaa acgacgagcg tgacaccacg    13260
atgcctgtag caatggcaac aacgttgcgc aaactattaa ctggcgaact acttactcta    13320
gcttcccgga acaattaat agactggatg gaggcggata agttgcagg atcacttctg     13380 cgctcggccc tcccggctgg ctggtttatt gctgataaat ctggagccgg tgagcgtggg    13440
tctcgcggta tcattgcagc actggggcca gatggtaagc cctcccgcat cgtagttatc    13500
tacacgacgg ggagtcaggc aactatggat gaacgaaata gacagatcgc tgagataggt    13560
gcctcactga ttaagcattg gtaatgacag aagtcaaaag cctccggtcg gaggcttttg    13620
actttctgct agatctgttt caatgcggtg aagggcagg cagctgggga ttatgtcgag    13680
acccggccag catgttggtt ttatcgcata ttcagcgttg tcgcgtttac ccaggtaaaa    13740
```

-continued

```
tggaagcagt gtatcgtctg cgtgaatgtg caaatcagga acgtaaccgt ggtacataga    13800
tgcagtccct tgcgggtcgt tcccttcaac gagtaggacg cggtgccctt gcaaggctaa    13860
ccattgcgcc tggtgtactg cagatgaggt tttataaacc cctcccttgt gtgacataac    13920
ggaaagtaca accgggtttt tatcgtcagg tctttggttt gggttaccaa acacactccg    13980
catatggcta atttggtcaa ttgtgtagcc agcgcgacgt tctactcggc ccctcatctc    14040
aaaatcagga gccggtagac gaccagcttt ttccgcgtct ctgatagcct gcggtgttac    14100
gccgatcagg tctgcaactt ctgttatacc ccagcggcga gtaatacgac gcgcttccgg    14160
gctgtcatcg ccgaactgtg cgatggcaat agcgcgcgtc atttcctgac cgcgattgat    14220
acagtctttc agcaaattaa ttaacgacat cctgtttcct ctcaaacatg cccttatctt    14280 tgtgttttc atcatacttt acgtttttaa agcaaagcaa cataaaaaaa gcaaagtgac     14340
ttagaaaacg caaagttaag gttcaaatca atttttttgat gcgctacaga agctatttag   14400
cttcatctaa gcgcaacggt attacttacg ttggtatatt taaaacctaa cttaatgatt    14460
ttaaatgata ataaatcata ccaattgcta tcaaaagtta agcgaacatg ctgattttca    14520
cgctgtttat acactttgag gcatctctat ctcttccgtc tctatattga aacacaatca    14580
aagaacatca atccatgtga catccccac tatctaagaa caccataaca gaacacaaca     14640
taggaatgca acattaatgt atcaataatt cggaacatat gcactatatc atatctcaat    14700 tacgaacat atcagcacac aattgcccat tatacgc                              14737
```

<210> SEQ ID NO 38
<211> LENGTH: 33
<212> TYPE: DNA
<213> ORGANISM: Artificial Sequence
<220> FEATURE:
<223> OTHER INFORMATION: Primer lacFSfi

<400> SEQUENCE: 38

```
cccaatggcc cgggaggcct acttaagtaa gcc                                 33
```

<210> SEQ ID NO 39
<211> LENGTH: 46
<212> TYPE: DNA
<213> ORGANISM: Artificial Sequence
<220> FEATURE:
<223> OTHER INFORMATION: Primer lacRSfi

<400> SEQUENCE: 39

```
tggcatgggc cacccgggcc agctagctca ggcgccattc gccatt                   46
```

<210> SEQ ID NO 40
<211> LENGTH: 47
<212> TYPE: DNA
<213> ORGANISM: Artificial Sequence
<220> FEATURE:
<223> OTHER INFORMATION: Primer PRD1 POL- F

<400> SEQUENCE: 40

```
aacagacagc agcatgccgc gccgttcccg taaaaggtg gaatata                   47
```

<210> SEQ ID NO 41
<211> LENGTH: 48
<212> TYPE: DNA
<213> ORGANISM: Artificial Sequence
<220> FEATURE:
<223> OTHER INFORMATION: Primer PRD POL R

<400> SEQUENCE: 41
ctgactctgg atatcttatt atgttccttt gattgtgcgc ttgataaa    48

<210> SEQ ID NO 42
<211> LENGTH: 28
<212> TYPE: DNA
<213> ORGANISM: Artificial Sequence
<220> FEATURE:
<223> OTHER INFORMATION: Primer telN-F

<400> SEQUENCE: 42
gcggatcccg atatccagag acttagaa    28

<210> SEQ ID NO 43
<211> LENGTH: 29
<212> TYPE: DNA
<213> ORGANISM: Artificial Sequence
<220> FEATURE:
<223> OTHER INFORMATION: Primer telN-R

<400> SEQUENCE: 43
cgaagcttct tttagctgta gtacgtttc    29

<210> SEQ ID NO 44
<211> LENGTH: 1833
<212> TYPE: DNA
<213> ORGANISM: Artificial Sequence
<220> FEATURE:
<223> OTHER INFORMATION: Vector pSMART HCAmp

<400> SEQUENCE: 44
gacgaattct ctagatatcg ctcaatactg accatttaaa tcatacctga cctccatagc    60
agaaagtcaa aagcctccga ccggaggctt ttgacttgat cggcacgtaa gaggttccaa    120
ctttcaccat aatgaaataa gatcactacc gggcgtattt tttgagttat cgagattttc    180
aggagctaag gaagctaaaa tgagtattca acatttccgt gtcgccctta ttcccttttt    240
tgcggcattt tgccttcctg tttttgctca cccagaaacg ctggtgaaag taaaagatgc    300
tgaagatcag ttgggtgcac gagtgggtta catcgaactg gatctcaaca gcggtaagat    360
ccttgagagt ttacgccccg aagaacgttt tccaatgatg agcacttttta aagttctgct    420
atgtggcgcg gtattatccc gtattgacgc cgggcaagag caactcggtc gccgcataca    480
ctattctcag aatgacttgg ttgagtactc accagtcaca gaaaagcatc tcacggatgg    540
catgacagta agagaattat gcagtgctgc cataaccatg agtgataaca ctgcggccaa    600
cttacttctg gcaacgatcg gaggaccgaa ggagctaacc gctttttgc acaacatggg    660
ggatcatgta actcgccttg atcgttggga accggagctg aatgaagcca taccaaacga    720
cgagcgtgac accacgatgc ctgtagcaat ggcaacaacg ttgcgcaaac tattaactgg    780
cgaactactt actctagctt cccggcaaca attaatagac tggatggagg cggataaagt    840
tgcaggatca cttctgcgct cggcccctccc ggctggctgg tttattgctg ataaatctgg    900
agccggtgag cgtgggtctc gcggtatcat tgcagcactg gggccagatg gtaagccctc    960
ccgcatcgta gttatctaca cgacggggag tcaggcaact atggatgaac gaaatagaca    1020
gatcgctgag ataggtgcct cactgattaa gcattggtaa tgagggccca aatgtaatca    1080
cctggctcac cttcgggtgg gcctttctgc gttgctggcg ttttttccata ggctccgccc    1140
ccctgacgag catcacaaaa atcgatgctc aagtcagagg tggcgaaacc cgacaggact    1200
ataaagatac caggcgtttc ccctggaagc tccctcgtg cgctctcctg ttccgaccct    1260

```
gccgcttacc ggatacctgt ccgcctttct cccttcggga agcgtggcgc tttctcatag    1320
ctcacgctgt aggtatctca gttcggtgta ggtcgttcgc tccaagctgg gctgtgtgca    1380
cgaacccccc gttcagcccg accgctgcgc cttatccggt aactatcgtc ttgagtccaa    1440
cccggtaaga cacgacttat cgccactggc agcagccact ggtaacagga ttagcagagc    1500
gaggtatgta ggcggtgcta cagagttctt gaagtggtgg cctaactacg gctacactag    1560
aagaacagta tttggtatct gcgctctgct gaagccagtt acctcggaaa aagagttggt    1620
agctcttgat ccggcaaaca accaccgct ggtagcggtg ttttttttgt ttgcaagcag    1680
cagattacgc gcagaaaaaa aggatctcaa gaagatcctt tgattttcta ccgaagaaag    1740
gcccacccgt gaaggtgagc cagtgagttg attgcagtcc agttacgctg gagtctgagg    1800
ctcgtcctga atgatatcaa gcttgaattc gtt                                 1833

<210> SEQ ID NO 45
<211> LENGTH: 14549
<212> TYPE: DNA
<213> ORGANISM: Artificial Sequence
<220> FEATURE:
<223> OTHER INFORMATION: Vector pNZKC

<400> SEQUENCE: 45
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaaagttccg tgggaaggga     360
ttgcagaaaa gaataaccgc gaatactttt aacgcctata tgagcagggc aagaaagcgg     420
tttgatgata aattacatca tagctttgat aaaaatatta ataaattatc ggaaaagtat     480
cctctttaca gcgaagaatt atcttcatgg ctttctatgc ctacggctaa tattcgccag     540
cacatgtcat cgttacaatc taaattgaaa gaaataatgc cgcttgccga agagttatca     600
aatgtaagaa taggctctaa aggcagtgat gcaaaaatag caagactaat aaaaaaatat     660
ccagattgga gttttgctct tagtgattta acagtgatg attggaagga gcgccgtgac     720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca     900
acatacatgc agtctatcta tgatattttg aataatcctg cgactttatt tagttttaaac    960 actcgttctg gaatggcacc tttggccttt gctctggctg cggtatcagg gcgaagaatg    1020
attgagataa tgtttcaggg tgaatttgcc gtttcaggaa agtatacggt taatttctca    1080
gggcaagcta aaaacgctc tgaagataaa agcgtaacca gaacgattta actttatgc    1140 gaagcaaaat tattcgttga attattaaca gaattgcgtt cttgctctgc tgcatctgat    1200
ttcgatgagg ttgttaaagg atatggaaag gatgatacaa ggtctgagaa cggcaggata    1260
aatgctattt tagcaaaagc atttaacc ct tgggttaaat cattttcgg cgatgaccgt    1320 cgtgttttata agatagccg cgctatttac gctcgcatcg cttatgagat gttcttccgc    1380
gtcgatccac ggtggaaaaa cgtcgacgag gatgtgttct tcatggagat tctcggacac    1440
gacgatgaga acacccagct gcactataag cagttcaagc tggccaactt ctccagaacc    1500
```

```
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcgaaactg cagctgcaac tacggacatc gccgtcccga ctgcagggac   2220
ttccccgcgt aaagcggggc ttaaattcgg gctggccaac cctattttc tgcaatcgct   2280 ggcgatgtta gttcgtgga tagcgttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt cttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag ttttttgtgcc   2880 tcggttaaac cgagggtcaa ttttttcatca tgatccagct tacgcaatgc atcagaaggg   2940
ttggctatat tcaatgcagc acagatatcc agcgccacaa accacgggtc accaccgaca   3000
agaaccaccc gtatagggtg gcttttcctga aatgaaaaga cggagagagc cttcattgcg   3060
cctccccgga tttcagctgc tcagaaaggg acagggagca gccgcgagct tcctgcgtga   3120
gttcgcgcgc gacctgcaga agttccgcag cttcctgcaa atacagcgtg gcctcataac   3180
tggagatagt gcggtgagca gagcccacaa gcgcttcaac ctgcagcagg cgttcctcaa   3240
tcgtctccag caggccctgg gcgtttaact gaatctggtt catgcgatca cctcgctgac   3300
cgggatacgg gctgacagaa cgaggacaaa acggctggcg aactggcgac gagcttctcg   3360
ctcggatgat gcaatggtgg aaaggcggtg gatatgggat ttttttgtccg tgcggacgac   3420 agctgcaaat ttgaatttga acatggtatg cattcctatc ttgtatagg tgctaccacc   3480 agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
```

-continued

```
ccgcagccac cttagatgtt gtctcaaacc ccatacggcc acgaatgagc cactggaacg      3900
gaatagtcag caggtacagc ggaacgaacc acaaacggtt cagacgctgc cagaacgtcg      3960
catcacgacg ttccatccat tcggtattgt cgacgacctg gtaagcgtat tgtcctggcg      4020
tttttgctgc ttccgagtag caatcctctt caccacaaag aaagttactt atctgcttcc      4080
agttttcgaa cccttcttct ttgagccgct tttccagctc attcctccac aaaacaggca      4140
cccatcctct gcgataaatc atgattattt gtccttaaa taaggctgta gaactgcaaa      4200
atcgctctcg ttcacatgct gtacgtagat gcgtagcaaa ttgccgttcc atccctgtaa      4260
tccaccttct ttggaaagat cgtccttgac ctcacgaaga accttatcca atagccctgc      4320
ggcacaagaa attgcctgct ctggatcagc aaattcatat tgattaatag gtgattgcca      4380
cacaccaaaa acaggaatca tcttttcggc taaacgcctc tcctgttctt tcttaatctc      4440
aagttgtaag cggaccagct caccatccat cattttttgt agatcatgcg ccactattca      4500
cccccactgg ccatcagcaa ataaagcttc atactcggac accggcaggc ggcttccacg      4560
gattgaaagg tcaagccaac cacgtccaga tgggtcagcc ttatccgatt cttcccaccg      4620
ttctgcagct gtagcaacca ggcattctac cgccttcatg tagtcttctg tacgaaacca      4680
gccgtagtta atgccaccat cagtaactgc ccaggccatc ttttctctt cggcctcaat      4740 agcccggatg cggttatcgc acagctcgcg acagtacttc agctgttcgt aatccagttg      4800
cttcaggaac tctggtgtcg acgtcatagt ggcttcacct ataggctttt tagaagcgcc      4860
ctggcttcgt ctgtgtggtc ttccatgctc ttatcgctgg caatgcagca ataaactccc      4920
tcactatctg agaacccgtt catccgaatg atcgtgaatg gaagttcccg gccagtttta      4980
taatcgctat agcttgtcgc gtcgtggctg accttgacca cataagggtc gtagccctcc      5040
acgatgacaa ggcattcccg ttgttttccc attacccctc cggttatatc gccacggctt      5100
gccgctggct tagaaacgct ttcagcagcc ttatttcgcg tactgatagc aggtccataa      5160
attcggtcat gtacagcgag gcgaacgttc tcgcgatgct ggccactggc cacaggcgta      5220
ccgcctccat ttcggttgct ggcaacgcgt tctccgccca cgcctccggt accgccaccg      5280
ggatagcctc cagtgcctgg ataattactg attgtgggc gtccggaacg tgctctgttt      5340
tggatcgagg gttaccatgt atatctatat ttagatccaa atcgcgatcc acttcgatgg      5400
tggttttttc caccttacgt gcgtgaattg ataaaccggc ctcgcggcgc ttctccacga      5460
tattcatgag gaactcgacc gagtccgggt caatggaacg catcgtgggg cgtgcatcgc      5520
cgtctctggc gcgtctggtc ttactggata gccccataga ctccaggatg cctatgcaga      5580
ggtctgcagg cgctttcttc ttgcctttct ctgtgttgaa gccgccgatg cgtaaaacgt      5640
tgtttagcag atcgcgccgt tccggcgtga gcaggttatc tctggcgcgt ttgagggcgt      5700
ccatgtctgc ttcaccttcc agggttttg gatcgatacc gcagtcgcgg aagtactgct      5760
gcagcgtcgc cgatttgagg gtgtagaaac cacgcatgcc tatctcaaca gcagggggtcg      5820 atttcactcg gtaatcggtt atggccggga atttagcctg gaactctgcg tcggcctgtt      5880
cccgcgtcat ggccgtagtg acgaactgct gccatcttcc ggcaacgcga taagcgtagg      5940
taaagtgaat caacgcttct tcacggtcaa ggcgacgggc ggttatctca tccagctgca      6000
tggtttcaaa caggcgcact ttttcaggc cgccgtcgaa atagaatttt aacgccacct      6060
cgtcgacatc cagctgcagc tccttttcga tgtcccagcg gaccagctgg gcctgctcat      6120
ccagggacag ggtgcgtttt tttatcaact catcgtgttc ggcctggtca ggagtatcga      6180
cactcaggtg gcgctccata agctgctcaa agaccagttc acgggcttct ttacgtaaat      6240
```

```
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagccgg agtggccagc cgtttcgagc aaggcctgcg     6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga     6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg cttaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacagatcg gttgcacggc    7860
tcagatgatt tctcgttaat ctggcgagcg acttccttca gccctctcag gctgtgcagg    7920
tcgttaaaat cgctgcattc cagctcaggg tcatcctcaa aagttgggta acacatttg     7980
acgccggaaa acttctccat gatgtcgaat ccggtgcgga ggcctgtgtt gccttttcct    8040
tcagctgagg atttgcggtc gttatcgaga gcgcaagtga tttgcgcagc cgggtacatg    8100
ttcaccagct gctcgacaac gtgaatcatg ttgttagcgg aaaccgcaat gactaccgcg    8160
tcaaagcgtt ttttcgggtc gtttctggtc gccagccaga tggatgcccc ggtggcgaaa    8220
ccctctgcag tcgcaatttt ttgcgccccc tgcaggtcgc caataacaaa gcatgcaccg    8280
acgaaatcac cgttagtgat ggcgctggtc tggaacttgc caccattcag atcgatacgt    8340
tgccagccaa caatccgccc gtcttttctt ccgtccaggt gggacagagg tatcgccatg    8400
taagttgttg gtccacggct ccatttcgca ctgtcgtgac tggtcacgcg acgtatatca    8460
caagcgccaa atacgtcacg aattcccttt tttaccgcat aaggccagga gccatcttca    8520
gctggcgaat gttcccaggc gcgatggaaa gccaaccatc caagcaggcg ttcctgctcc    8580
```

```
atctgattgt tttttaaatc attaacgcgt tgttgttcag ctcggaggcg gcgtgcttca    8640
gcctggcgct ccatgcgtgc acgttcttct tccggctgag cgaccacggt cgcaccattc    8700
cgttgctgtt cacggcgata ctccgaaaac aggaatgaaa agccactcca ggagccagcg    8760
tcatgcgctt tttcaacgaa gttaacgaaa ggataactga tgccatcctt gctctgctca    8820
aggcgtgaat agatttccac acggccttta aggctcttct gcagagcttc cggggaggaa    8880
ttattgtagg tggtatagcg ctctacacca ccgcgcggat tgagctgaat cttatcagca    8940
cacgcaggcc agttgatacc ggccatcttc gccagctcag tcagctcatc acgtgccgcg    9000
tcaagcagtg aaaacggatc gctgccaaag cgctccgcgt agaattcttg taaggtcatt    9060
ttttagcctt tccatgcgaa ttagcatttt ttcgggttga aaaaatccgc aggagcagcc    9120
acaataaacg cactatcttt ctgaaggacg tatctgcgtt atcgtggcta cttcctgaaa    9180
aaggcccgag tttgccgact cgggttttt ttcgtctttt ttcggctgct acggtctggt    9240
tcaaccccga caaagtatag atcggattaa accagaatta tagtcagcaa taaaccctgt    9300
tattgtatca tctaccctca accatgaacg atttgatcgt accgactact tggtgcacaa    9360
attgaagatc acttttatca tggataaccc gttgagagtt agcactatca aggtagtaat    9420
gctgctcgtc ataacgggct aatcgttgaa ttgtgatctc gccgttatta tcacaaacca    9480
gtacatcctc acccggtaca agcgtaagtg aagaatcgac caggataacg tctcccggct    9540
ggtagtttcg ctgaatctgg ttcccgaccg tcagtgcgta acggtgttc cgttgactca    9600
cgaacggcag gaatcgctct gtgttggcag gttctccagg ctgccagtct ctatccggtc    9660
cggtctctgt cgtaccaata acaggaacgc ggtctggatc agattcagtg ccatacagta    9720
tccattgcac gggcttacgc aggcattttg ccagcgatag cccgatctcc agcgacggca    9780
tcacgtcgcc acgttctaag ttttggacgc ccggaagaga gattcctaca gcttctgcca    9840
cttgcttcag cgtcagtttc agctctaaac ggcgtgcttt cagtcgttcg cctcgtgttt    9900
tcatacccctt aatcataaat gatctcttta tagctggcta taattttat aaattatacc    9960
tagctttaat tttcacttat tgattataat aatccccatg aaacccgaag aacttgtgcg   10020
ccatttcggc gatgtggaaa aagcagcggt tggcgtgggc gtgacacccg gcgcagtcta   10080
tcaatggctg caagctgggg agattccacc tctacgacaa agcgatatag aggtccgtac   10140
cgcgtacaaa ttaaagagtg atttcacctc tcagcgcatg ggtaaggaag gcataacag    10200
gggatcctct agagtcgacc tgcaggcatg caagcttcct gaatcgcccc atcatccagc   10260
cagaaagtga gggagccacg gttgatgaga gctttgttgt aggtggacca gttggtgatt   10320
ttgaactttt gctttgccac ggaacggtct gcgttgtcgg gaagatgcgt gatctgatcc   10380
ttcaactcag caaagttcg atttattcaa caaagccgcc gtcccgtcaa gtcagcgtaa   10440
tgctctgcca gtgttacaac caattaacca attctgatta gaaaaactca tcgagcatca   10500
aatgaaactg caatttattc atatcaggat tatcaatacc atatttttga aaaagccgtt   10560
tctgtaatga aggagaaaac tcaccgaggc agttccatag gatggcaaga tcctggtatc   10620
ggtctgcgat tccgactcgt ccaacatcaa tacaacctat aatttcccc tcgtcaaaaa   10680
taaggttatc aagtgagaaa tcaccatgag tgacgactga atccggtgag aatggcaaaa   10740
gcttatgcat ttctttccag acttgttcaa caggccagcc attacgctcg tcatcaaaat   10800
cactcgcatc aaccaaaccg ttattcattc gtgattgcgc ctgagcgaga cgaaatacgc   10860
gatcgctgtt aaaaggacaa ttacaaacag gaatcgaatg caaccggcgc aggaacactg   10920
ccagcgcatc aacaatattt tcacctgaat caggatattc ttctaatacc tggaatgctg   10980
```

```
ttttccctgg gatcgcagtg gtgagtaacc atgcatcatc aggagtacgg ataaaatgct   11040
tgatggtcgg aagaggcata aattccgtca gccagtttag tctgaccatc tcatctgtaa   11100
catcattggc aacgctacct ttgccatgtt tcagaaacaa ctctggcgca tcgggcttcc   11160
catacaatcg atagattgtc gcacctgatt gcccgacatt atcgcgagcc catttatacc   11220
catataaatc agcatccatg ttggaattta atcgcggcct cgagcaagac gtttcccgtt   11280
gaatatggct cataacaccc cttgtattac tgtttatgta agcagacagt tttattgttc   11340
atgatgatat attttatct tgtgcaatgt aacatcagag attttgagac acaacgtggc   11400
tttgttgaat aaatcgaact tttgctgagt tgaaggatca gatcacgcat cttcccgaca   11460
acgcagaccg ttccgtggca aagcaaaagt tcaaaatcac caactggtcc acctacaaca   11520
aagctctcat caaccgtggc tccctcactt tctggctgga tgatggggcg attcaggaag   11580
cttgcatgcc tgcaggtcga ctctagagga tccccgagaa cccgataatc gctaccagtg   11640
atgatggctg ttttgcggcg gcgtgagcca tcggcaattt cgataatgcc tgacgtcctt   11700
ctggcgaacg cggggttctg ctgtcctgaa gtgaggaatg aagggataag gtcggccagc   11760
gctgattcgt tcagcaattc ctgatcacgt tcattaccga gccaaaccat tgtggccttt   11820
tcgactttat cagcaggaat ggtttccagc ttaaaagtca cgttgcggcc atcaagcttg   11880
aattcgtacg cagaaaggcc cacccgaagg tgagccagtg tgattacatt tgcggccagt   11940
ccagttacgc tggagtcact agtgcggccg cgacaacttg tctagggccc aatggcccgg   12000
gaggcctact taagtaagcc ggcttagcta gcgggacagg tttcccgact ggaaagcggg   12060
cagtgagcgc aacgcaatta atgtgagtta gctcactcat taggcacccc aggctttaca   12120
ctttatgctt ccggctcgta tgttgtgtgg aattgtgagc ggacaacaat ttcacacagg   12180
aaacagctat gaccatgatt acgccaagct atttaggtga gactatagaa tactcaagct   12240
tgcatgcgat acgtatcgtt aacgatggat ccgacgcacg tgcgaattcg ccctatagtg   12300
agtcgtatta caattcactg gccgtcgttt tacaacgtcg tgactgggaa aaccctggcg   12360
tcacccaact taatcgcctt gcagcacatc cccctttcgc cagctggcgt aatagcgaag   12420
aggcccgcac cgatcgccct tcccaacagt tgcgcagctg aatggcgaat ggcgcctgag   12480
ctagcattgc cggcattctt aagtaggcct cccgggccat tggcgcgcca gacttgaagt   12540
cgcggccgca ctgaccattt aaatcatacc aacatggtca aataaaacga aaggctcagt   12600
cgaaagactg ggcctttcgt tttaatctga tcggcacgta agaggttcca actttcacca   12660
taatgaaata agatcactac cgggcgtatt ttttgagtta tcgagatttt caggagctaa   12720
ggaagctaaa atggagaaaa aaatcactgg ataccaccg ttgatatat cccaatggca   12780
tcgtaaagaa cattttgagg catttcagtc agttgctcaa tgtacctata accagaccgt   12840
tcagctggat attacggcct ttttaaagac cgtaaagaaa aataagcaca gtttatcc    12900
ggcctttatt cacattcttg cccgcctgat gaatgctcat ccggaatttc gtatggcaat   12960
gaaagacggt gagctggtga tatgggatag tgttcaccct tgttacaccg ttttccatga   13020
gcaaactgaa acgttttcat cgctctggag tgaataccac gacgatttcc ggcagtttct   13080
acacatatat tcgcaagatg tggcgtgtta cggtgaaaac ctggcctatt tccctaaagg   13140
gtttattgag aatatgtttt tcgtctcagc caatccctgg gtgagtttca ccagttttga   13200
tttaaacgtg gccaatatgg acaacttctt cgccccgtt ttcaccatgg gcaaatatta   13260
tacgcaaggc gacaaggtgc tgatgccgct ggcgattcag gttcatcatg ccgtttgtga   13320
```

-continued

```
tggcttccat gtcggcagaa tgcttaatga attacaacag tactgcgatg agtggcaggg    13380
cggggcgtaa cctaggtgac agaagtcaaa agcctccggt cggaggcttt tgactttctg    13440
ctagatctgt ttcaatgcgg tgaagggcca ggcagctggg gattatgtcg agacccggcc    13500
agcatgttgg ttttatcgca tattcagcgt tgtcgcgttt acccaggtaa aatggaagca    13560
gtgtatcgtc tgcgtgaatg tgcaaatcag gaacgtaacc gtggtacata gatgcagtcc    13620
cttgcgggtc gttcccttca acgagtagga cgcggtgccc ttgcaaggct aaccattgcg    13680
cctggtgtac tgcagatgag gttttataaa cccctccctt gtgtgacata acggaaagta    13740
caaccgggtt tttatcgtca ggtctttggt ttgggttacc aaacacactc cgcatatggc    13800
taatttggtc aattgtgtag ccagcgcgac gttctactcg gcccctcatc tcaaaatcag    13860
gagccggtag acgaccagct ttttccgcgt ctctgatagc ctgcggtgtt acgccgatca    13920
ggtctgcaac ttctgttata ccccagcggc gagtaatacg acgcgcttcc gggctgtcat    13980
cgccgaactg tgcgatggca atagcgcgcg tcatttcctg accgcgattg atacagtctt    14040
tcagcaaatt aattaacgac atcctgtttc ctctcaaaca tgcccttatc tttgtgtttt    14100
tcatcatact ttacgttttt aaagcaaagc aacataaaaa aagcaaagtg acttagaaaa    14160
cgcaaagtta aggttcaaat caatttttg atgcgctaca gaagctattt agcttcatct    14220
aagcgcaacg gtattactta cgttggtata tttaaaacct aacttaatga ttttaaatga    14280
taataaatca taccaattgc tatcaaaagt taagcgaaca tgctgatttt cacgctgttt    14340
atacactttg aggcatctct atctcttccg tctctatatt gaaacacaat caaagaacat    14400
caatccatgt gacatccccc actatctaag aacaccataa cagaacacaa cataggaatg    14460
caacattaat gtatcaataa ttcggaacat atgcactata tcatatctca attacggaac    14520
atatcagcac acaattgccc attatacgc                                      14549
```

LINEAR VECTORS, HOST CELLS AND CLONING METHODS

CROSS-REFERENCE TO RELATED APPLICATIONS

This application is a continuation of U.S. patent application Ser. No. 12/159,956, filed on May 15, 2009, which is a national stage filing under 35 U.S.C. 371 of International Application No. PCT/US2007/060500, filed on Jan. 12, 2007, which claims the benefit of U.S. Provisional Patent Application Ser. Nos. 60/758,479, filed Jan. 12, 2006 and 60/747,733, filed May 19, 2006, which are incorporated by reference herein.

STATEMENT REGARDING FEDERALLY SPONSORED RESEARCH

The invention was made with United States government support awarded by the National Institutes of Health (Grant No. 1R43HG002627-01). The United States has certain rights in the invention.

INTRODUCTION

Dramatic advances in high-throughput sequencing technology have resulted in the nearly complete deciphering of the human genome and genomes of several other species. In stark contrast to these technical achievements, there has been little improvement in the vectors or host cells used to generate the recombinant clone libraries necessary for genomic sequence analysis. Numerous genetic elements are unstable or unclonable in currently available vector/host systems due to toxicity, secondary structure, replication errors, and other poorly understood characteristics. Conventional vectors replicate to high copy number, actively induce transcription and translation of inserted fragments, and allow cloned promoters to interfere with plasmid maintenance. Moreover, conventional methods of cloning have primarily utilized supercoiled plasmid DNA, which causes instability due to torsional stress and enzymatic processing of secondary structures. Instability caused by these factors leads to sequence stacking, clone gaps, sequence gaps, and other difficulties.

The standard vectors for construction of libraries, pUC18 and its derivatives, contain many features useful for general cloning, including blue/white screening capability, large multiple cloning sites, and high copy number, as well as the ability to generate RNA transcripts from bacteriophage promoters and single-stranded DNA from the M13 origin of replication. However, many of these attributes are incompatible with stable maintenance of certain inserts, leading to clone gaps and seemingly "unclonable" DNA fragments. Such problematic sequences are typically characterized by high AT-content, strong secondary structure, deleterious open reading frames, or cis-acting functions (e.g., transcriptional promoters or replication origins).

Linear vectors provide an alternative to the use of circular supercoiled plasmids for cloning. Linear vectors are not subject to the supercoiling found in circular plasmids and therefore may stably maintain inserts that have primary or secondary structures that are unstable when supercoiled. This additional stability may result in improved sequencing data and reductions in the number of sequence gaps and cloning gaps in genomic assemblies. Linear vectors also exhibit the ability to clone larger inserts using standard methods. Linear vector cloning systems may stably clone DNA in the mid-size range (10-50 kb), without the use of packaging systems required with cosmid or fosmid cloning. Linear vector cloning systems may also be used to clone fragments in the large size range (>100 kb), without the extensive vector purification needed for BAC cloning.

One linear cloning vector that has been investigated is derived from the *E. coli* double-stranded DNA ("dsDNA") phage N15. In contrast to typical temperate bacteriophages that physically integrate their prophage DNA into the host's chromosome during the establishment of lysogeny, N15 replicates in the lysogen as a low-copy-number, extrachromosomal linear plasmid that has covalently closed hairpin loop telomeres. Nearly half the genome of N15, including the head and tail genes, has extensive homology with that of bacteriophage lambda ($\lambda$). The elements that control transcription and determine prophage immunity have homologues in the repressor, operator, and anti-terminator of $\lambda$ and P22. The lytic development of N15 resembles that of $\lambda$, resulting in virions with $\lambda$-like morphology; and it lysogenizes at similar frequencies. The portions of phage N15 required for replication and maintenance of the linear prophage have no known equivalents in phage lambda. Conversely, the head and tail genes of phage KO2 of *Klebsiella oxytoca* are completely distinct from those of N15, but the genes for replication and maintenance of the linear prophages of N15 and KO2 are highly homologous. (Sherwood R C et al., J. Bacteriol., 186(6): 1818-32 (March 2004), the disclosure of which is incorporated herein by reference).

The replication of linear N15 vectors requires three components: an origin of replication (Ori), the replication initiation protein RepA, and the protelomerase TelN for resolution of the replicated telomeres. To form the prophage, the cohesive ends of the injected linear DNA are joined to create a circular intermediate. The protelomerase recognizes a unique palindromic site (tel RL), located near the center of the previously linear molecule. It processes the linear or circularized DNA to produce a linear molecule with closed ends telL and telR, both in vitro and in vivo. The only N15 gene required for replication of the circular form of the plasmid is repA, which contains helicase, primase, and origin binding activities.

The origin itself is within the repA gene, and replication proceeds bidirectionally using the host *E. coli* DNA polymerase. N15 replication is independent of the host genes polA, dnaA, dnaJ, dnaK, grpE, and recA. The N15 genome also contains a partition system (sopBA), having homology to F' plasmid genes, but with a dispersed set of centromere sites.

The N15 virus has previously been modified into a 13.8 kb cloning vector, pG591 (SEQ ID NO:1). The pG591 vector, which is schematically shown in FIG. 1, retains the genes essential for replication and copy number regulation, including telN (protelomerase), repA (replicase or replication factor), and cB (prophage repressor or copy number regulator), but the phage structural genes have been removed. It also lacks the partition genes sopBA necessary for stable maintenance of the vector. Instead, the sop functions may be supplied in trans using *E. coli* strain DH10B31sop, which has a chromosomally integrated N15 sop operon and anti-repressor gene, the latter under control of an arabinose-inducible promoter.

BRIEF SUMMARY OF THE INVENTION

Although it is functional as a vector, molecular cloning results using pG591 have revealed several major drawbacks. First, the left arm containing the 12 kb NotI vector fragment (telN-repA-cB-KanR) is capable of transforming cells without the addition of an insert or the right telomere fragment, which lacks a selectable marker. Even if self-ligation of the vector is prevented via dephosphorylation, many aberrant clones and some non-recombinant clones are generated. Aberrant recombinant clones include dimers of the 12 kb fragment or circular permutations of the vector with or without various deletions between telN and repA. Thus, because pG591 generates a high frequency of empty vector background and alternate structures, it is not acceptable for molecular cloning purposes. In addition, pG591 has only a single restriction site (NotI) available for cloning, so it is not convenient for library construction or restriction analysis of clones. Moreover, a strong promoter is directed from the right telomeric region toward the NotI site, which is likely to reduce the stability of cloned inserts by transcribing them.

The present invention relates to improved linear cloning vectors and host cells suitable for propagating the improved linear cloning vectors, kits that include both the linear cloning vectors and a strain of host cells, and methods of cloning polynucleotide sequences using the linear cloning vectors. The invention permits cloning of large or "difficult" polynucleotide sequences which may otherwise not be cloned using conventional circular plasmid vectors. For example, the linear vector of the invention can maintain fragments that are unstable in the supercoiled plasmid form. The linear mode of replication imparts high fidelity replication of repeats, large palindromes, and AT-rich DNA. In addition, the invention allows for simplified molecular analysis of cloned sequences.

In one aspect, the invention provides a linear cloning vector derived from a bacteriophage capable of being maintained *E. coli*. The linear cloning vector of the invention includes a left arm comprising a left telomere and a first selectable marker; a right arm comprising a right telomere and a second selectable marker; and a cloning region located between the left arm and the right arm.

The invention also provides host cells suitable for use with the linear vector. In some embodiments, the invention provides a recombinant host cell having a polynucleotide sequence encoding a protelomerase integrated into the host cell genome.

In a further aspect, the invention provides a kit comprising a linear cloning vector of the invention and a suitable host cell.

In yet another aspect, the invention provides a method of cloning a polynucleotide sequence. The method includes steps of processing a linear cloning vector of the invention to separate the right arm from the left arm; ligating the first end of the polynucleotide sequence to the right arm and the second end of the polynucleotide sequence to the left arm to provide a ligation product; transforming a host cell with the ligation product; and growing the transformed host cell on medium, such that selection is provided for the first and second selectable markers of the linear cloning vector.

In an additional aspect, the invention provides a method of cloning at least two distinct polynucleotides. The method includes steps of processing each of the polynucleotides to provide a linking sequence on both termini of the polynucleotides; processing a linear cloning vector of the invention to separate the right arm from the left arm and to provide a linking sequence on the terminus opposite the telomere of each arm; forming a ligation product comprising the polynucleotides and the right and left arms, wherein the arms are noncontiguous with each other and are separated by both of the polynucleotides to be cloned; transforming a host cell with the ligation product; and growing the transformed host cell on medium, such that selection is provided for the first and second selectable markers of the linear cloning vector, wherein multiplication of the host cell results in cloning of the polynucleotides.

The objects and advantages of the invention will appear more fully from the following detailed description of the preferred embodiment of the invention made in conjunction with the accompanying drawings.

BRIEF DESCRIPTION OF THE DRAWINGS

FIG. 4A shows the results of selection on kanamycin plus ampicillin and FIG. 4B shows the results of selection on ampicillin only.

DETAILED DESCRIPTION OF SEVERAL EMBODIMENTS

Figure 1:
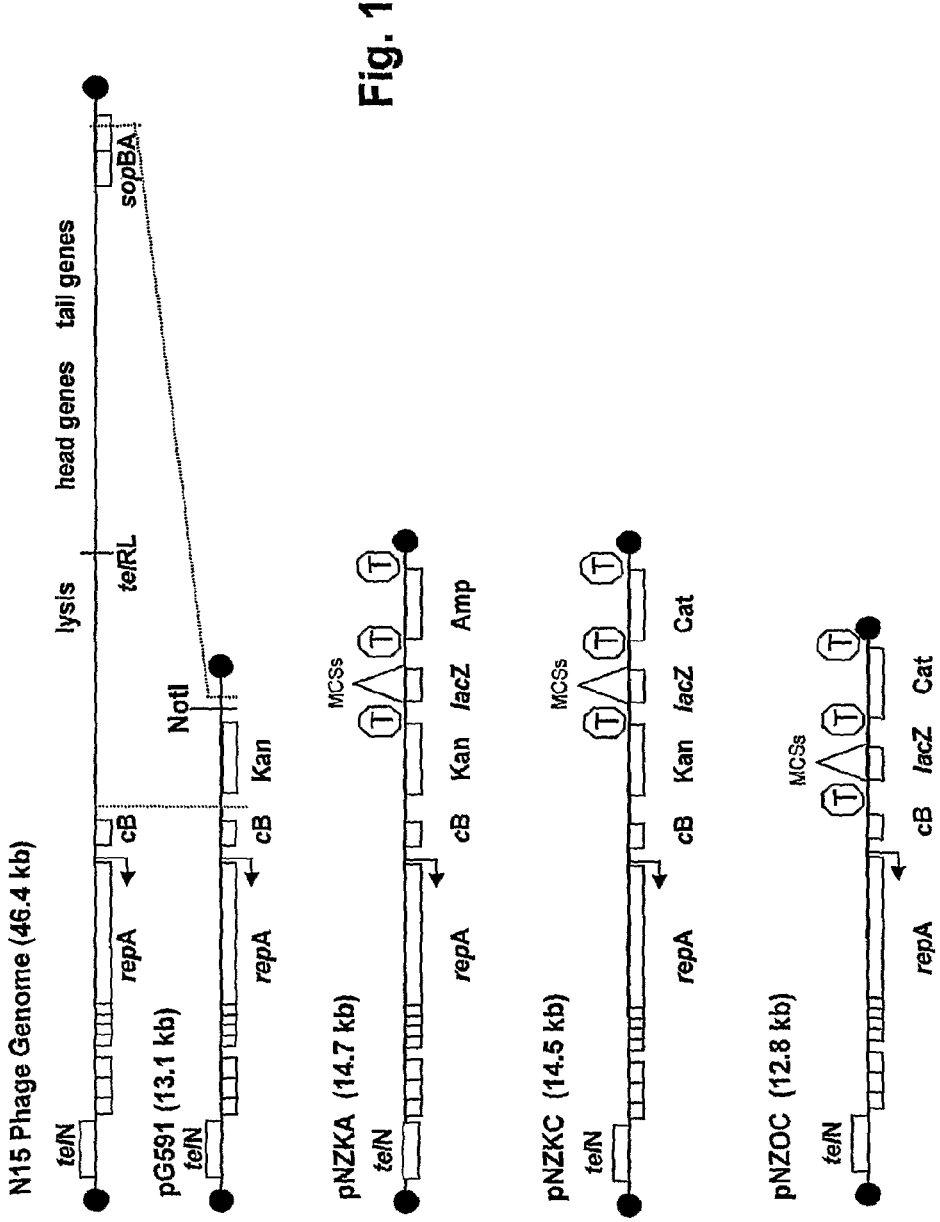
FIG. 1 is a schematic diagram of N15 phage, plasmid pG591, and three linear cloning vectors of the invention: pNZKA, pNZKC, and pNZOC. As shown, pNZKA, pNZKC, and pNZOC carry the genes telN, repA, and cB, which are essential for replication and regulation of copy number. Promoters are indicated by arrows and transcriptional terminators by "T". Dark circles represent the telomeres. The lacZ "stuffer" fragment, situated between a pair of multiple cloning sites (MCSs), is removed before ligation to inserts.

Before any embodiments of the invention are explained in detail, it is to be understood that the invention is not limited in its application to the details of construction and the arrangement of components set forth in the following description or illustrated in the following figures and examples. The invention is capable of other embodiments and of being practiced or of being carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

As used in this specification and the appended claims, the singular forms "a," "an," and "the" include plural referents unless the content clearly dictates otherwise. Thus, for example, reference to a composition containing "a vector" includes a mixture of two or more vectors. It should also be noted that the term "or" is generally employed in its sense including "and/or" unless the content clearly dictates otherwise.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. The values listed above are only examples of what is specifically intended.

Linear Vectors

In one embodiment, the invention provides a linear cloning vector derived from a bacteriophage (also referred to herein as "phage") that is capable of replicating in *E. coli* as an extrachromosomal linear plasmid. Suitably, the bacteriophage used to derive the cloning vector is a temperate phage, i.e., it has a characteristic lysogenic life cycle. As used herein, a cloning vector is said to be "derived from" a bacteriophage when a genomic structure is isolated from the bacteriophage (or its host cell) and subjected to further molecular manipulation to produce a linear cloning vector. Such molecular manipulation may include deletion of structural genes or regulatory sequences, and/or introduction of one or more sequences such as promoter, operator or enhancer sequences, restriction sites, telomeres, sequences encoding selectable markers and/or transcriptional terminator sequences. As will be appreciated, a cloning vector will be considered to be "derived from" a bacteriophage whether it is directly produced (e.g., purified from a colony) or indirectly produced (e.g., through multiple rounds of cloning and subcloning, PCR amplification or synthetic methods). Most suitably, the phage from which the linear vector is derived is suitably selected from lambda, N15, KO2, PRD1 or PY54.

The linear plasmid pKO2 present in *K. oxytoca* CCUC 15788 is a prophage that is related to *E. coli* phage N15 and *Yersinia* phage PY54 and that apparently has a lifestyle that is very similar to theirs. The N15, PY54, and $\phi$KO2 genomes are mosaically related. Some regions are sufficiently similar that the N15 and $\phi$KO2 plasmid partitioning proteins, replicase, protelomerases (hairpin end generation), and prophage repressors are thought to have the same or extremely similar target site specificities in both phages (Sherwood R. Casjens et al. (2004) *J. Bacteriol.* 186(6):1818-32).

The $\phi$KO2 early region, which is similar to but mosaically related to those of phages N15 and PY54, consists of 43 predicted genes in two large divergent operons and several smaller transcription units. As in other lambdoid phages, the putative $\phi$KO2 prophage repressor gene (gene 36 in Sherwood R. Casjens et al. (2004) *J. Bacteriol.* 186(6):1818-32) lies between the divergent early left and early right operons. It and the putative Cro repressor (encoded by gene 37 as shown in Sherwood R. Casjens et al. (2004) *J. Bacteriol.*, 186(6):1818-32) are 88 and 87% identical to the N15 cB repressor and Cro, respectively. This high level of similarity and the fact that their putative three OR and two OL operator binding sites all match the N15 5'-TTATAN$_6$TATAA early operator consensus (Ravin, V., N. Ravin, S. Casjens, M. E. Ford, G. F. Hatfull, and R. W. Hendrix. (2000) *J. Mol. Biol.* 299:53-73) suggest that N15 and $\phi$KO2 have the same repressor target specificity.

The linear cloning vectors of the invention include a left arm having a left telomere and a first selectable marker, a right arm having a right telomere and second selectable marker, and a cloning region located between the left arm and the right arm. As used herein, a "telomere" refers to a polynucleotide or polypeptide structure on the end (or ends) of a linear DNA molecule that protects the termini of the DNA from recombination and/or exonucleolytic degradation. Suitable telomeres include covalently closed ends, sequences capable of binding terminal proteins (e.g., as in PRD1), and tracts of polynucleotide repeats (e.g., poly A, C, G, T or U tracts). Examples of telomeres useful in constructing the linear vectors of the present invention include those derived from bacteriophages lambda, N15, KO2, PRD1 and PY54, as well as from some linear chromosomes, e.g., those from *Borrelia* spp. and *Agrobacterium tumefaciens*.

As used herein, a "selectable marker" refers to a phenotypic trait conferred on transformed cells that protects them from a selective agent in their environment, i.e., the growth media. Examples of selectable markers include, but are not limited to, antibiotic resistance markers (e.g., genes encoding resistance to kanamycin, ampicillin, chloramphenicol, gentamycin, or trimethoprim) and metabolic markers (e.g., amino acid synthesis genes or transfer RNA genes). As is appreciated in the art, the origin of replication can also be used as a selectable marker. In some cases, the first and second selectable markers will be antibiotic resistance markers, and will be different from each other. In other cases, the first or second selectable marker may be an origin of replication (Ori). Incorporating different selectable markers on each arm of the linear vector allows for simultaneous selection of both arms among recombinant clones. Selection for both arms ensures that the structure of the recombinants is correct, having exactly one left arm and one right arm.

The cloning region of the linear vector may include a restriction site, or may be a multiple cloning site (MCS) including more than one restriction site. One or more of the restriction sites are suitably unique restriction sites, i.e., they do not occur in the vector arms. Suitably, the cloning region may include a reporter stuffer region, e.g., the lacZ$\alpha$ gene or a lethal gene. The reporter stuffer region may be flanked by restriction sites, or more suitably, MCSs, so that the entire reporter stuffer region may be replaced by one or more polynucleotides to be cloned. This configuration advantageously permits cloning of coding sequences which may be toxic to the cells, because strong promoters in or adjacent to the reporter region are eliminated, thus preventing transcription (and subsequent translation) of the toxic insert. In some embodiments, the total cloning capacity of the vector is approximately 50 kb.

Optionally, the linear cloning vector includes two or more transcriptional terminator regions. As used herein and in the art, a "transcriptional terminator region," is a regulatory sequence which induces dissociation of a transcription complex in prokaryotic cells. In some embodiments, the linear cloning vector includes a pair of transcriptional terminator regions flanking the cloning region. The use of transcriptional terminator regions in this configuration reduces or eliminates transcription from the cloning region into the vector, thereby preventing interference with the function of the selectable markers, such as an antibiotic resistance coding sequence or origin of replication. Optionally, the linear cloning vector includes a third transcriptional terminator region after the selectable marker of the right arm to prevent transcription into the telomere region. Suitable transcriptional terminators are palindromic sequences which can form hairpin loop structures. The transcriptional terminator regions may be the same or different, but use of different transcriptional terminator regions may result in a more stable vector construct due to a reduced likelihood of deletions caused by recombination between identical terminator sequences. Transcriptional terminators may be unidirectional or bidirectional. Bidirectional terminators advantageously block transcription into the insert from vector promoters and into the vector from promoters within the insert. Suitably, the transcriptional terminator following the selectable marker on the right arm is a bidirectional transcriptional terminator. Most suitably, the transcriptional terminators are functional in the absence of host factors (i.e., are rho independent). Suitable transcriptional terminator sequences include the trpA terminator, T3 terminator, T7 terminator, rrnB T1 terminator, and others as described by Reynolds, et. al, J. Mol. Biol. (1992) 224:31-51, the disclosure of which is incorporated herein by reference in its entirety.

Exemplary suitable configurations for linear cloning vectors in accordance with the present invention are designated "pNZKA," (or "pJAZZ-KA," or "NZAN," SEQ ID NO:3) "pNZKC" (SEQ ID NO:45), and "pNZOC" (or "NZTC3," or "pJAZZ-OC," SEQ ID NO: 2). These linear vector constructs are shown schematically in FIG. 1. The vectors may be provided in undigested form, or may be provided as pre-digested and dephosphorylated linear vector arms.

The linear cloning vectors described herein have at least four advantages over lambda and circular plasmid vectors. First, efficient ligation of insert to vector can be driven to completion by a molar excess of vector arms. In contrast, plasmid vectors may require numerous titrations to optimize the vector:insert ratio, as excess vector will result in independent vector molecules ligating to each end of the insert, creating a non-viable recombinant molecule. Second, in vitro lambda DNA packaging extracts limit the insert sizes to a narrow size range of approximately 35-45 kilobases (kb), whereas linear vector insertions have no minimum size, and the maximum size may be about 30-50 kb. Third, the linear vector maintains inserts as large as those of the bacteriophage lambda vector while simplifying use and production of vectors and recombinants. Fourth, the linear vector system can be used with a simple, conventional protocol for ligation, transformation and DNA isolation, and additional components are not required (e.g., lambda packaging extracts that are required for cosmid/fosmid cloning).

Conditions for high efficiency ligation favor the linear vector over circular plasmids. Formation of a circular recombinant plasmid occurs in a two step reaction: an intermolecular reaction between the plasmid and insert, followed by an intramolecular reaction between the ends of the hybrid molecule to form a circle. Ligation of circular plasmid vector and large insert DNAs are typically performed in dilute reactions of about 100-150 microliters to facilitate intermolecular joining of one insert molecule to one much smaller vector molecule. The requirement for subsequent recircularization favors smaller inserts over larger ones, requiring stringent size selection and vector dephosphorylation to achieve acceptable results. In contrast, ligation reactions occur most efficiently at high DNA concentrations or under macromolecular crowding conditions. Unfortunately, these conditions favor intermolecular joining, which is optimal for forming concatamers, but not useful for creating circular plasmids. A linear vector preparation contains a left and right vector arm, each with only one end capable of ligation, so high vector-to-insert ratios can be used to drive the joining reaction. Thus, linear vectors provide an improved method for generating large insert libraries by lowering the bias against large inserts.

Host Cells

In further embodiments, the invention provides host cells suitable for propagating the linear cloning vectors. A "host cell" is any cell that may be transformed with heterologous DNA, i.e., any cell that is a competent cell. Suitably, the host cell is an *E. coli* cell. Suitable strains of *E. coli* are known, e.g., DH10B cells or E. CLONI 10G cells (Lucigen, Middleton, Wis.). In some embodiments, host cells may be engineered to enhance transformation efficiency and/or maintenance of the linear vector.

Host cells may contain a coding sequence for a prokaryotic telomerase, which is referred to herein and in the art as "protelomerase" (or, alternatively, "telomere resolvase"), either on a conventional plasmid, or stably integrated into the host cell genome. A suitable protelomerase is the N15 protelomerase, referred to herein and in the art as "TelN." Optionally, host cells may express protelomerase prior to transformation with the linear cloning vector. Suitably, the transformation efficiency of linear vectors in host cells expressing a protelomerase such as TelN is 10-100 fold higher than in host cells not containing a protelomerase coding sequence.

In addition to a coding sequence for a protelomerase, host cells may further contain a coding sequence for partitioning proteins. The partitioning proteins suitably provide segregation stability to ensure accurate, non-random distribution of replicated linear plasmid molecules between the daughter cells, such that each daughter cell will receive the linear plasmid. The coding sequence for the partitioning proteins may be maintained in the host cells on a conventional plasmid, or stably integrated into the host cell genome. Suitably, the partitioning proteins are the sopA and sopB genes encoded by the sopBA region of the N15 genome.

In addition to a protelomerase coding sequence and/or a coding sequence for partitioning proteins, host cells may further contain a coding sequence for an antirepressor. One suitable antirepressor coding sequence is the N15 antirepressor gene (antA), which is known to counteract cB repression that, in turn, is believed to control the expression of RepA protein. Thus, induction of antA leads to higher expression of RepA, thereby stimulating N15 replication and increasing prophage copy number. The N15 antA gene is suitably placed under the control of an inducible promoter and may be contained on a plasmid or stably integrated into the genome of the host cell.

In some embodiments, the host cell contains a coding sequence for a suitable polymerase for replication of the linear vector, either contained on a plasmid or stably integrated into the genome of the host cell. As an example, the coding sequence for the PRD1 polymerase (Bamford et al., Virology 183(2):658-676 (1991), the disclosure of which is incorporated herein by reference) may suitably be introduced into host cells designed to replicate linear vectors derived from PRD1.

Kits

In further embodiments, the invention provides kits containing a linear cloning vector of the invention and host cells, as described herein. Suitably, the host cells are electrocompetent or chemically competent cells modified to enhance transformation efficiency or maintenance of the linear cloning vector included in the kit. Linear cloning vectors provided in kits may be optionally pre-digested and dephosphorylated. Other optional components of the kits may include ligation buffer, ligase, control insert DNA for ligation, sequencing primers, restriction endonucleases, a phosphatase, a polymerase and/or a kinase. The kit may also suitably provide instructions for using the kit in accordance with the methods described herein.

Cloning Methods

In some embodiments, the invention provides methods of cloning a polynucleotide sequence. The polynucleotide sequence to be cloned is suitably linear, i.e., having a first end and a second end. The steps of the method include at least processing the linear cloning vector to separate the right arm from the left arm, ligating the first end of the polynucleotide sequence to the right arm and the second end of the polynucleotide sequence to the left arm to provide a ligation product, transforming a suitable host cell with the ligation product, and growing the transformed host cell on medium that selects for the first and second selectable markers of the linear cloning vector.

In some embodiments, linear cloning vectors of the invention are suitably used to clone at least two distinct polynucleotides, or insert sequences. These embodiments may be suitably employed, for example, in the cloning and expression of multi-subunit polypeptides, (e.g., the heavy and light chains of an antibody). Such vectors are also suitably used to analyze an interaction between two or more known polypeptides (e.g., a receptor and its ligand(s)), an interaction between a known polypeptide and unknown polypeptides produced from, e.g., a library; or an interaction between two or more unknown polypeptides produced from, e.g., one or more libraries. As will be appreciated by those of skill in the art, simultaneously cloning two or more inserts also provides a means of sequencing multiple sequences via one sequencing reaction, i.e., "multiplex sequencing."

The linear cloning vectors of the invention suitably provide capacity for simultaneously cloning at least two insert sequences. In some embodiments, three inserts may be cloned. In some embodiments, four inserts may be cloned. In some embodiments, five inserts may be cloned. In some embodiments six inserts may be cloned. In some embodiments, seven inserts may be cloned. In some embodiments, eight inserts may be cloned. In some embodiments, nine inserts may be cloned. In some embodiments, ten or more inserts may be cloned. It will be appreciated that the upper limit of the number of inserts that may be cloned using the linear cloning vectors of the invention depends on their collective size. In other words, the upper limit depends on the total capacity of the vector, e.g., 50 kb in some embodiments.

In some embodiments, at least one of the polynucleotides to be cloned is of unknown sequence. In particular embodiments, each of the polynucleotides is of unknown sequence.

In some embodiments, the sequence of at least one polynucleotide is known. In other embodiments, at least a portion of one of the sequence of at least one of the polynucleotides is known (e.g., 5, 10, 15, 20, 25 bases are known). In some embodiments, the polynucleotides to be cloned are derived from a "library," which herein refers to a collection of insert sequences derived from a source of DNA such as, e.g., an environmental source or a genome, or cDNA derived from a particular tissue or organism.

Methods of cloning at least two distinct polynucleotides, or insert sequences, include a step of processing each of the insert sequences to provide a linker sequence on both termini. A "linker sequence," as used herein, is a sequence of nucleotides that is compatible with another linker sequence in a ligation reaction. Each of the polynucleotides to be cloned are suitably processed to provide either: a) a linker sequence on one terminus that is compatible with a linker sequence on one of the vector arms and a terminus of one other insert sequence, or b) a linker sequence on each terminus that is compatible with a linker sequence on a terminus of two other insert sequences, or c) a linker sequence on each terminus that is compatible with a linker sequence on a terminus of one other insert sequence and one vector arm. A linker sequence may be provided, e.g., by restriction, PCR amplification and/or ligation of an oligonucleotide to the termini of the insert. The linker sequence is suitably less than 12 nucleotides in length. In some embodiments, the linker sequence is homopolymeric. Non-limiting examples of suitable linker sequences include AAA, TTT, CCC and GGG. Other examples include GTG, CAC, GTGT, and CACA. In some embodiments, one linker sequence is a blunt end. In some embodiments, the termini of each insert sequence are not compatible with each other, i.e., the insert sequences cannot self-ligate. Self-ligation may suitably be prevented by providing incompatible linker sequences on the termini or removing free 5' phosphate groups.

In a further step, the linear cloning vector of the invention is processed to separate the right and left arms. In an optional further step, the right arms may be purified away from the left arms. In a further step, the arms are treated to provide a linker sequence on the terminus opposite the telomere on each arm. Optionally, separated vector arms may be processed to prevent re-ligation, e.g., by treating the 5' ends with a phosphatase. In some embodiments, the vector arms are processed to provide "fixed orientation" multiple insert cloning, wherein the insert sequences can assemble only in a fixed orientation relative to each other and to the vector arms upon ligation.

In a further step, a ligation product is formed. The ligation product includes the insert sequences and the right and left vector arms, wherein the arms are noncontiguous with each other and are separated by the insert sequences. Most suitably, each of the insert sequences is present and present only once in the ligation product. In some embodiments, one ligation reaction provides a mixture of the desired ligation product (containing each insert and a right and left vector arm), as well as undesired ligation products lacking one or more of the inserts. However, one of skill in the art may readily determine which ligation product in the mixture is the desired product using standard techniques, for example, sequencing or restriction analysis. The single-ligation embodiment of the invention is suitable for cloning fewer polynucleotides, e.g., two or three inserts; it is also suitable for cloning a larger number of inserts, e.g., concatamers of insert sequences.

Alternatively, the ligation product may be the ultimate product of multiple ligation reactions which may be employed in a suitable scheme based on the number of insert sequences. One suitable scheme for cloning two inserts is demonstrated in Example 12. Suitable schemes for cloning three or more inserts are also envisioned. Some schemes may employ linkers designed such that a specific end of each insert can be ligated only to a specific end of another insert. The resulting recombinants suitably have all inserts in a fixed orientation relative, to each other and to the vector. Ligation of a vector arm to an insert sequence suitably results in a ligation product that has only one end available for further ligation, the other end being the "inert" telomere. Thus, in some embodiments, iterative ligations are performed, wherein an additional insert sequence is iteratively added to the product of the previous ligation. A viable recombinant clone is produced only upon addition of a fragment containing the opposing vector arm. Suitable schemes for cloning additional inserts may be determined by those of ordinary skill in view of the present disclosure.

Further steps in the method of cloning at least two polynucleotides include transforming a host cell with the ligation product and growing the transformed host cell on medium, such that selection is provided for the first and second selectable markers of the linear cloning vector. It is appreciated that multiplication of the host cell results in cloning of each of the polynucleotides. Verification of the identity and orientation of the cloned polynucleotides may be accomplished by standard methods, such as, e.g., restriction analysis or sequencing.

The following examples are provided to assist in a further understanding of the invention. The particular materials and conditions employed are intended to be further illustrative of the invention and are not limiting upon the reasonable scope of the appended claims.

EXAMPLES

Example 1

Construction of Host Strains for Linear Vectors

A standard, commercially available strain of competent *E. coli* (E. CLONI 10G, Lucigen, Middleton, Wis.) was used to prepare host cells for efficient transformation with linear vectors of the invention. To create one host strain (referred to herein as E. CLONI® 10G-iTel), the telN gene was PCR-amplified from phage N15 DNA (Ravin et al., J. Mol. Biol. 299(1):53-73 (May 2000), the disclosure of which is incorporated herein by reference) using the following primers:

```
telN-F:
                                   (SEQ ID NO: 42)
GCGGATCCCGATATCCAGAGACTTAGAA
(BamHI site underlined)

telN-R:
                                   (SEQ ID NO: 43)
CGAAGCTTCTTTTAGCTGTAGTACGTTTC
(HindIII site underlined)
```

The resulting PCR product was cloned into the BamHI/HindIII sites of pGZ119EH, which allows cloning of the target gene under control of IPTG-inducible Ptac promoter (Lessl et al., 1992, J. Bacteriol., 174: 2493-2500, incorporated herein by reference). The recombinant vector, designated pGZ-telN, expresses telN protein and encodes resistance to chloramphenicol. pGZ-telN DNA was transformed into E. CLONI 10G cells by electroporation to create the chloramphenicol resistant strain E. CLONI 10G-ptel.

To integrate the telN gene into the attB site in the chromosome of 10G cells, the fragment containing Ptac-telN was excised from pGZ-telN and cloned into the chromosome-integration vector pJW22 (Wild J, Hradecna Z, and Szybalski W (2002), Genome 12:1434-44, incorporated herein by reference), which encodes resistance to ampicillin. The resulting integration vector, pJW-telN, was digested with NotI to excise the fragment containing Ptac-telN, which was purified by gel-electrophoresis and circularized by self-ligation. The circularized fragment was transformed into E. CLONI 10G cells (Lucigen, Middleton, Wis.) carrying the integrase-producing plasmid pJW289t. Colonies that contained an integrated telN gene and which had lost the pJW289t plasmid were selected as described by Wild J, Hradecna Z, and Szybalski W (2002), Genome 12:1434-44, incorporated herein by reference. The resulting ampicillin resistant strain was designated E. CLONI 10G-iTel.

The influence of telN expression was tested by comparing the efficiency of transformation of E. CLONI 10G-iTel and parental E. CLONI 10G with linear pG591 DNA. The efficiency of transformation was 10- to 100-fold higher in E. CLONI 10G-iTel than in E. CLONI 10G. (Data not shown).

Next, the sopBA region of N15 along with a chloramphenicol resistance marker was integrated into the chromosome of E. CLONI 10G cells to create chloramphenicol resistant strain DH10B31sop. This strain also contains the anti-repressor AntA under control of the araBAD promoter. To add the telomerase gene to this strain, the ampicillin resistance gene of the plasmid pGZ-TelN was replaced with a gene encoding gentamycin resistance. This plasmid was transformed into DH10Bsop31 to generate strain GTS-8 (chloramphenicol and gentamycin resistant). GTS-8 allows highly efficient transformation with pNZKA, and copy number can be induced by addition of arabinose.

A cassette containing the telN gene, the sopBA operon, and the antA gene was integrated onto the chromosome of E. CLONI 10G cells as follows: a DNA fragment comprising phage N15 sopBA operon (under control of its own promoter) and the antA antirepressor gene (under control of arabinose-inducible araP$_{BAD}$ promoter) was excised from plasmid pCD31sop (Mardanov A. V., and Ravin N. V., Abstracts of the conference "Lomonosov-2004", v. 1, p. 21, Moscow, Russia (2004), the disclosure of which is incorporated herein by reference) as an XhoI-MroNI fragment and cloned into the HindIII site of plasmid pJWtelN, described above, which contains the telN gene inserted into the vector pJW22. The resulting vector, pJW-telN31sop, was partially digested with NotI to excise the fragment containing telN-sopBA-antA, which was purified by gel-electrophoresis and circularized by self-ligation. The circularized fragment was transformed into E. CLONI 10G cells carrying the lambda integrase-producing plasmid pJW289t. Colonies that contained an integrated fragment comprising telN gene, sopBA operon and antA antirepressor, and which had lost the pJW289t plasmid were selected as described by Wild J, Hradecna Z, and Szybalski W, Genome 12:1434-44 (2002), the disclosure of which is incorporated herein by reference. The resulting ampicillin resistant strain, designated E.

CLONI 10G-telN31S (or, alternatively, BIGEASY TSA Cells), allow efficient transformation with the linear vector and permit induction of copy number.

Example 2

Construction of Linear Vectors a) Construction of NZCK3

A linear vector suitable for general cloning was derived from pG591 (SEQ ID NO:1). (Ravin et al., Nucleic Acids Res. 31(22):6552-60 (2003), the disclosure of which is incorporated herein by reference) pG591 was digested with NotI and treated with a mixture of DNA repair enzymes that generates blunt, phosphorylated ends (DNATERMINTOR® Kit, Lucigen, Middleton, Wis.). The 12 kb fragment containing the left telomere, telN, repA, and kanamycin resistance was gel isolated. pG591 was also digested with BglII, and the 1.3 kb fragment containing the right telomere was gel isolated.

A fragment containing the lacZalpha and ampicillin genes was constructed as follows: The lacZalpha gene of the vector pEZ BAC (SEQ ID NO: 15, nucleotides 155-598) was PCR amplified using the two overlapping forward primers T7RC-NotF (SEQ ID NO:16) and NSAS-LacZ-F (SEQ ID NO:17) plus the reverse primer NNASA-LacZ-R (SEQ ID NO:18) to create a fragment called TerZ. The ampicillin resistance gene was amplified from pSMART-HCAmp (SEQ ID NO:44, nucleotides 97-1063) by PCR with the two overlapping forward primers rrn-Fd (SEQ ID NO:19) and rrn-pCmF2 (SEQ ID NO:20) plus the reverse primer TonAmpR (SEQ ID NO:21). The resulting fragment was re-amplified with rrn-Fd and TonB-R (SEQ ID NO:22) to generate the fragment TAmpT. The TerZ and TAmpT fragments were each digested with NcoI and ligated. A band corresponding to the size of the ligation product of TerZ plus TAmpT was gel isolated and re-amplified with the primers T7del (SEQ ID NO:23) and TonBR2 (SEQ ID NO:24). This PCR product was ligated into the HincII site of pSMART HCKan, and excised from the vector by digestion with EcoRV and BglII. The EcoRV-BglII fragment was ligated to the blunt 11 kb fragment and the BglII fragment of pG591, generating the linear vector NZAN (SEQ ID NO:3, also referred to herein as "pJAZZ™.-KA").

The lacZ fragment of the vector NZAN was amplified by PCR with the primers LacANN-For (SEQ ID NO:25) and LacANN-Rev (SEQ ID NO:26). The resulting PCR product was re-amplified with the primers LacApSA-For (SEQ ID NO:27) and LacAsSA-Rev (SEQ ID NO:28). The product was digested with ApaI and AscI, ligated to the 12 kb ApaI fragment and the 2 kb AscI fragment of the vector NZAN, transformed into E. CLONI 10G-pTel cells, and selected on plates containing ampicillin plus kanamycin. The resulting linear vector was designated NZASA (SEQ ID NO:4).

To add additional cloning sites and binding sites for sequencing primers, the lacZ fragment was amplified from NZASA using primers LacE-SL1-F (SEQ ID NO:29) and LacA SR2-Rev (SEQ ID NO:30). The resulting PCR product was digested with AflIII, ligated to the end-repaired 10-kb NotI fragment and the 3-kb NcoI fragment of the vector NZASA, transformed into E. CLONI 10G-pTel cells, and selected on plates containing ampicillin plus kanamycin. The resulting linear vector was designated NZAhd (SEQ ID NO:5).

To create a version of the linear vector for use with BIGEASY TSA cells, the ampicillin resistance gene of NZAhd was replaced with a chloramphenicol resistance gene. The AhdI restriction site in the vector backbone was also destroyed to allow cloning into AhdI sites in the multiple cloning site. The resulting vector, designated NZCK3 (SEQ ID NO:6), was created by ligation of four fragments. The first (left-most) fragment was the 7.8 kb AhdI fragment of NZAhd encompassing the left telomere, telN gene, and part of the repA gene. The second fragment was a region of approximately 4.5 kb amplified from NZAhd by PCR with the primers 7847-F2 (SEQ ID NO:31), which introduces a mutation that destroys the AhdI site, and LacA-SR2-Rev (SEQ ID NO:30). This fragment was treated with Tfl DNA polymerase in the presence of dGTP to add a single G tail to the 3' termini. It was further digested with SpeI to remove the lacZ region from the right side of the fragment. The third fragment was a region of ~1.3 kb containing the lacZ region flanked by multicloning sites (MCSs), followed by the chloramphenicol resistance gene. This fragment was amplified from NZAhd by PCR with the primers LacE-SL1-F (SEQ ID NO:29) and CamTonB-Rev (SEQ ID NO:32); it was subsequently digested with SpeI and BglII. The fourth fragment was the 1.3 kb BglII fragment of NZAN that contains the right telomere. A ligation reaction containing these four fragments was transformed into E. CLONI 10G-pTel cells, and recombinants containing NZCK3 were selected on plates containing chloramphenicol plus kanamycin.

b) Construction of NZOC

A linear vector employing the origin of replication as selectable marker on the left arm and the chloramphenicol resistance gene as a selectable marker on the right arm was constructed. This vector, designated NZTC2 (SEQ ID NO:7), was created by ligation of three fragments. The first (left-most fragment) was a 10 kb XbaI fragment from NZASA (SEQ ID NO:4), containing the left telomere, telN gene, and repA gene. The XbaI restriction site was made blunt by treatment with T4 DNA polymerase in the presence of dNTPs. The second fragment, containing the lacZ gene and flanking DNA, was amplified from NZCK3 by PCR with the primers T7-RC-Del (SEQ ID NO:8) and pCmOR (SEQ ID NO:9) and digested with AscII. The third fragment was a ~2.2 kb AscI fragment from NZCK3 containing the chloramphenicol resistance gene and the right telomere. The ligation reaction of these fragments was transformed into E. CLONI 10G iTel cells (as prepared in Example 1) and plated on agarose containing chloramphenicol. The correct NZTC2 clone was confirmed by sequencing.

NZTC2 contained an AhdI site in the repA gene. A derivative lacking this site was created from three fragments. The first (left-most) fragment was the 7.8 kb AhdI fragment of NZAhd (SEQ ID NO:5) encompassing the left telomere, telN gene, and part of the repA gene. The second fragment was a region of approximately 4.5 kb amplified from NZTC2 by PCR, using as forward primers a mixture of NZg7847a-F2 (SEQ ID NO:10) and NZg7847a-F3 (SEQ ID NO:11), which introduce a mutation that destroys the AhdI site, and the reverse primer NZ-RevB (SEQ ID NO:12). This fragment was re-amplified with NZg7847a-F2 as the forward primer and a mixture of NZ-RevA (SEQ ID NO:13) and NZ-RevC (SEQ ID NO:14) as reverse primers. This fragment was treated with Tfl DNA polymerase in the presence of dGTP to add single 3' G overhangs to the ends, and further digested with SwaI to generate a blunt site on the right side of the fragment. The third fragment was the approximately 2.2 kb SwaI fragment of NZTC2 that contains the right telomere. The ligation reaction of these three fragments was transformed into E. CLONI BIGEASY TSA cells, and recombinants containing NZOC (also referred to as "NZTC3" or "pJAZZ-OC") (SEQ ID NO:2) were selected on plates containing chloramphenicol. The correct clone was confirmed by sequencing.

Example 3

Construction of a *Tetrahymena thermophila* 6-20 kb Genomic Library

*T. thermophila* is a free-living, widely distributed, ciliated protozoan. The cellular, structural, and functional complexity of this organism is comparable to that of human and other metazoan cells. The macronuclear (somatic) genome consists of 160 Mb processed in vivo into ~300 sub-chromosomal fragments. Constructing libraries with inserts of >6 kb is extremely problematic for this genome, presumably because the AT content ranges from 75-85%.

The linear pNZKA vector was used to successfully clone libraries of large AT-rich fragments. A library of 5-10 kb fragments of the *Tetrahymena* genome was created by ligation of sheared, end-repaired macronuclear DNA to a blunt digest of pNZKA. Of 54 clones analyzed, 51 had inserts of the expected size (data not shown).

Figure 2:
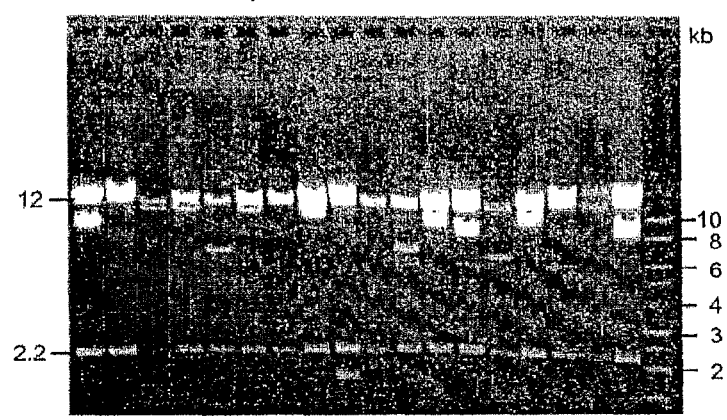
FIG. 2 is a photograph of an electrophoretic gel used to resolve NotI digests of clones of *Tetrahymena* genomic DNA clones produced in pNZKA, a linear vector of the invention. Migration of the left and right arms of the vector at 12 and 2.2 kb, respectively, is indicated.
Figure 3:
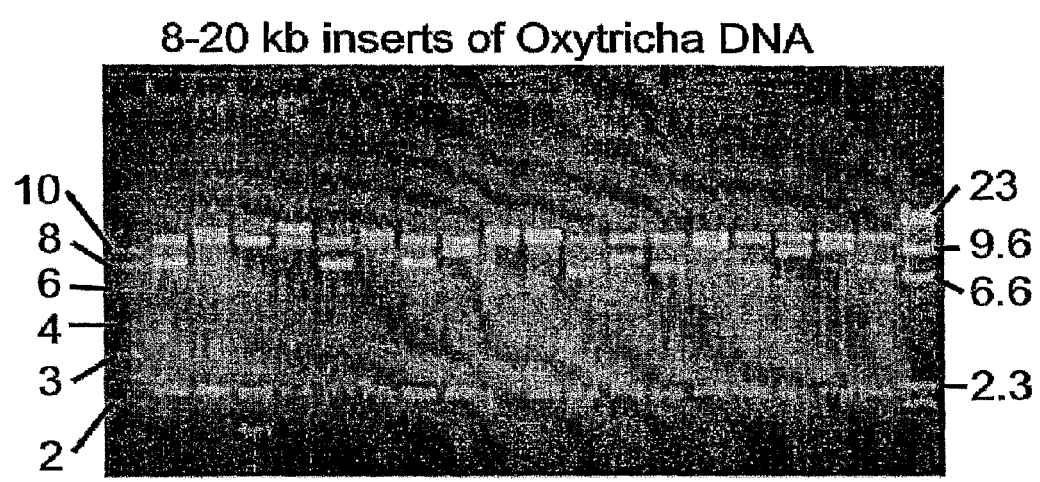
FIG. 3 is a photograph of an electrophoretic gel used to resolve NotI digests of *Oxytricha* genomic clones produced in pNZKA, a linear vector of the invention.

A library was also successfully created with clones in the range of 6-20 kb, which to our knowledge, represents a library of the largest *Tetrahymena* fragments ever cloned. Genomic DNA was sheared to 6-20 kb, end-repaired, gel-purified, and ligated to a SmaI digest of pNZKA. Ligations were electroporated into DH10B31sop cells and selected on plates containing kanamycin plus ampicillin. The clones produced large colonies on selective plates, grew vigorously in culture, and yielded relatively high amounts of linear plasmid DNA from standard alkaline lysis minipreps. One-fifth of the DNA from each miniprep was incubated with NotI to excise the insert and subjected to gel electrophoresis. The results are shown in FIG. 2. Vector bands are 12 kb and 2.2 kb. Inserts are in the range of 6-20 kb. Furthermore, sequencing reactions required only 150 ng of DNA from clones made with the linear vector.

Example 4

*Oxytricha trifallax* 8-20 kb Genomic Library

Another genome that has been very problematic to clone is that of the ciliated protozoan *Oxytricha trifallax*. The DNA in the somatic macronucleus of *Oxytricha* is processed in vivo into "nanochromosomes" of ~2-40 kb (75% AT), each fragment typically containing a single gene. Using circular vectors, previous attempts have been made to create a library of this DNA has been created for genomic sequencing, with the largest cloned insert being less than ~6 kb.

To make a large-insert genomic library of the *Oxytricha* macronuclear genome, the DNA was end-repaired to generate blunt ends, size selected to 8-20 kb, and ligated to pNZKA. The ligation was transformed into *E. coli* DH10B31sop cells, which contain the SopBA region, and into E. CLONI 10G-pTel, prepared as in Example 1. The transformed cells were plated on media containing kanamycin and ampicillin, to select for both arms of the vector. (Both cell lines are resistant to chloramphenicol.) E. CLONI 10G-pTel yielded approximately 12-fold more colonies than the DH10B31sop cells. For each library, 18 clones were analyzed. As shown in FIG. 3, 15-17 clones had inserts in the range of 8-20 kb, and vector bands are 12 kb and 2.2 kb. A library with *Oxytricha* inserts of this size has not been created previously.

Example 5

Construction of a *Pneumocystis carinii* 8-20 kb Genomic Library

The pNZKA vector was used to clone the genomic DNA from *Pneumocystis carinii*, the causative agent of a severe pneumonia in immuno-compromised patients. The epidemiology of *P. carinii* infection is poorly understood and its life cycle remains obscure. Large-scale sequencing of the *P. carinii* genome will help elucidate the molecular basis of the pathogenicity and speed development of drug and vaccine targets. Cloning the DNA of *P. carinii* into circular vectors has previously proven problematic, even for small fragments.

Figure 4:
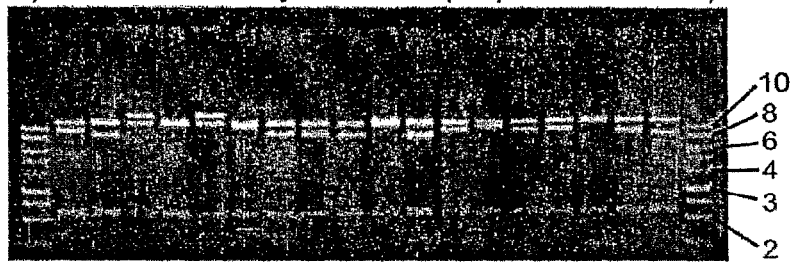
FIG. 4 is a photograph of an electrophoretic gel used to resolve NotI digests of *Pneumocystis* genomic clones produced in pNZKA, a linear vector of the invention.
Figure 4:
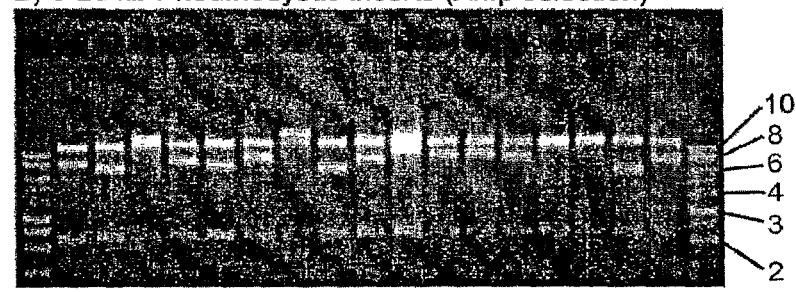

Genomic *P. carinii* DNA was sheared to 8-20 kb, end-repaired to generate blunt ends, size selected to 8-20 kb, and ligated to SmaI-digested pNZKA. The ligation was transformed into *E. coli* DH10B31sop and into E. CLONI 10G-pTel. To show that the origin of replication can be used successfully as a selectable marker, the library was plated on media containing kanamycin plus ampicillin (FIG. 4A) and on media containing only ampicillin (FIG. 4B). Colonies were randomly picked for analysis. Each lane in FIG. 4 contains $\frac{1}{5}^{th}$ of the DNA from a 1.5 ml miniprep, cut with NotI to excise the insert. Vector bands are 12 kb and 2-2 kb. Inserts were in the range of 8-20 kb. As shown in FIG. 4, both the number of colonies and the fraction of recombinants clones with the correct structure remained unchanged, regardless of the presence of kanamycin. This result indicates that the origin of replication can serve as a selectable marker, as it is essential for viability of the clones. Therefore, drug selection for the left arm of the vector, which contains the origin of replication, is redundant.

Example 6

Introduction of a Selectable Marker on the Right Arm Results in Fewer Non-Recombinants To investigate the effects of a selectable marker on the right arm of the vector, a control insert of 2 kb, containing the lacZα gene fragment, was ligated to the vector pNZKC. Both the vector and the insert were digested with NotI, and the vector was further treated by dephosphorylation. The vector preparation was also self-ligated or unligated (i.e., incubated without ligase or insert DNA). The ligations were transformed into E. CLONI 10G-iTel cells, which are ampicillin resistant, and plated on chloramphenicol to select for the right arm of the vector. They were also transformed into E. CLONI 10G-pTel cells, which are chloramphenicol resistant, eliminating any selection for the right arm of the vector. Transformation into cells that allow selection for the right arm of the vector resulted in fewer than 0.1% non-recombinants, whereas lack of right arm selection led to nearly 20% non-recombinant, white colonies, as shown in Table 1:

TABLE 1

Cloning into the linear vector pNZKC with or without selection for the right vector arm.

| E. cloni 10G-iTel(AmpR) | | | E. cloni 10G-iTel(CamR) |
|---|---|---|---|
| Pos. Control | Self-ligated | Unligated | Pos. Control |
| 1360 Blue | 0 Blue | 1 Blue | 300 Blue |
| 1 White | 0 White | 0 White | 70 White |

Example 7

Construction of a Cone Snail cDNA Library

An example of a particularly difficult insert to clone is the cDNA derived from the poison duct of the cone snail (*Conus* sp.). cDNA was generated from cone snail poison duct RNA, end-repaired, and fractionated into size ranges of 0.3-0.7 kb ("set A") and 0.7-2 kb ("set B"). Linkers were ligated to the cDNA, and it was amplified by PCR using primers complementary to the linkers. The PCR products were ligated into pNZKC, transformed into E. CLONI iTel cells, and plated on kanamycin plus chloramphenicol media. Plasmid DNA was isolated from randomly chosen colonies, digested with NotI, and size fractionated using gel electrophoresis.

Figure 5:
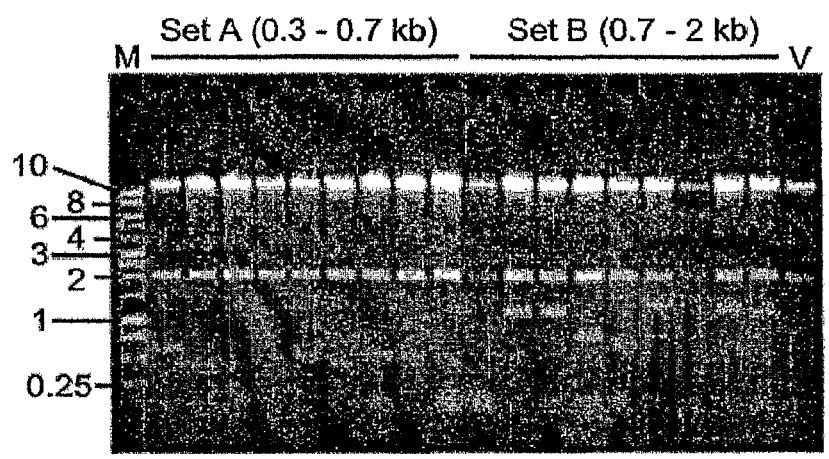
FIG. 5 is a photograph of an electrophoretic gel used to resolve NotI digests of a cone snail cDNA library contained in pNZKC vectors. Set A shows 0.3-0.7 kb inserts; set B shows 0.7-2 kb inserts. The lane labeled "M" designates a size marker; "V" designates empty vector control.

As shown in FIG. 5, the linear vector produced only clones in the expected size range of 0.3 to 2 kb. Ligation and transformation of the cone snail cDNAs into conventional circular plasmids resulted in predominantly empty vectors or inserts of <100 bp (data not shown).

Example 8

Linear Vectors Containing Only the Left Arm Convert to a Circular Plasmid pNZKC was digested with SmaI, and the 12 kb left arm was gel purified away from the lacZ stuffer region and the right arm. 1-2 kb fragments of DNA isolated from the genome of *Thauera selenatis* were prepared by shearing (using a HYDROSHEAR device, Gene Machines, San Carlos, Calif.). The fragments were end-repaired, gel-purified, and ligated to a SmaI digest of the purified left arm of pNZKC. Ligations were electroporated into E. CLONI 10G-iTel cells and selected on plates containing kanamycin. Eighteen kanamycin resistant colonies were randomly picked for analysis and $\frac{1}{5}^{th}$ of the DNA from a 1.5 ml miniprep was resolved using agarose gel electrophoresis.

Figure 6:
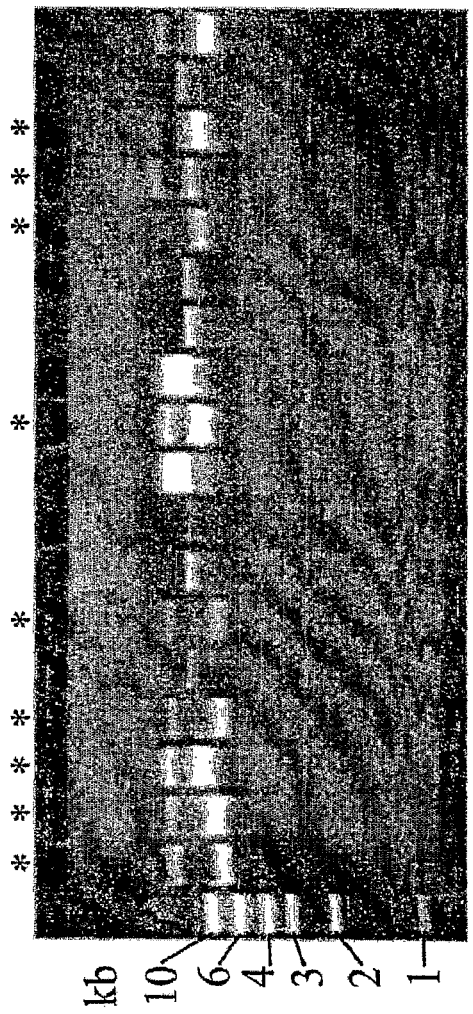
FIG. 6 is a photograph of an electrophoretic gel used to resolve uncut *Thauera selenatis* genomic DNA clones ligated in the presence of purified left arms of pNZKC. Aberrant clones migrating as circular molecules are indicated.

The results, shown in FIG. 6, show that at least 10 out of the 18 clones were converted to a circular plasmid, showing supercoiled and relaxed circular forms, while the remaining 8 clones appeared to be linear. In all 18 cases, the clones were not able to survive on plates containing chloramphenicol, indicating they lacked a right arm. Aberrant clones are indicated by "*" in FIG. 6.

Example 9

Selection for Both Left and Right Arms Favors the Linear Vector Form

*Tetrahymena* genomic DNA was sheared to 4-10 kb, end-repaired, gel-purified, and ligated to the left and right arm of a SmaI digest of pNZKC. Ligations were electroporated into E. CLONI 10G-iTel cells and selected on plates containing kanamycin only (which selects only for the left arm of the vector) or kanamycin plus chloramphenicol (which selects for both arms of the vector). Colonies were randomly picked for analysis, and ⅕ of the DNA from a 1.5 ml miniprep was cut with NotI to excise the insert and resolved using agarose gel electrophoresis.

Figure 7:
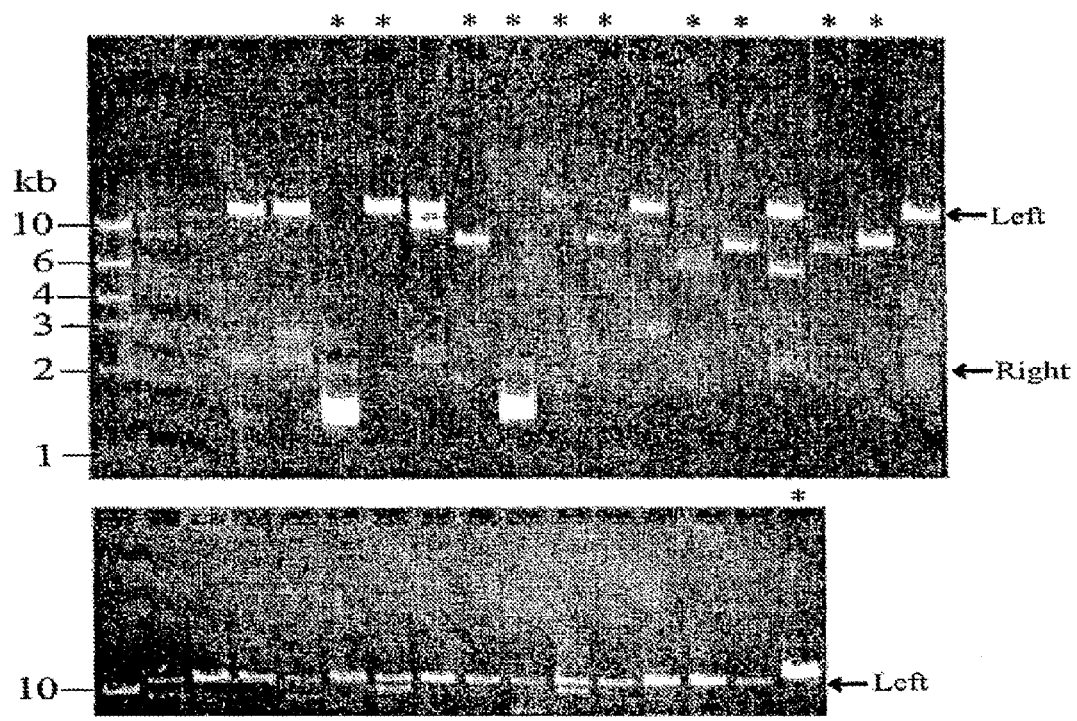
FIG. 7 is a photograph of an electrophoretic gel used to resolve NotI digests of *Tetrahymena* genomic DNA clones produced in pNZKC and selected on kanamycin plates (upper panel) or chloramphenicol plates (lower panel). Aberrant clones migrating as circular or deleted linear molecules are indicated. Migration of left and right arms of the linear vector are indicated.

As shown in FIG. 7, when the right arm was not selected by chloramphenicol, 8 out of 18 clones appeared to be linear molecules missing the expected 2.2 kb NotI fragment, which represents the right arm of the vector (FIG. 7, upper panel), and 2 of the clones (lanes 6 and 10) appeared to be circular plasmids instead of linear vector. In contrast, when the right arm was under selection by chloramphenicol, 17 out of 18 clones contained the expected 2.2 kb NotI right arm fragment (FIG. 7, lower panel). Since the origin of replication is essential for viability of the vector, the left arm is under selection regardless of the antibiotic used.

Example 10

Improved Transformation Efficiency with Strains Containing the telN Gene

Genomic DNA from *Oxytricha trifallax* and from *Pneumocystis carinii* was sheared to 8-20 kb, end-repaired, gel fractionated, and purified. The linear vector pNZKA was digested with SmaI and dephosphorylated. Approximately 300 ng of each prepared genomic DNA was ligated in separate reactions to 50 nanograms of the prepared linear vector. The ligation reactions were heat-inactivated and transformed into host strains that had been rendered electrocompetent. The host strains included E. CLONI 10G-pTel, which contains a telN protelomerase coding sequence, and DH10B31sop cells, which does not contain a telN coding sequence. One-tenth of the transformed cells were plated onto media containing kanamycin, ampicillin, XGAL, and IPTG. After overnight growth, each ligation reaction yielded ~12-fold more colonies in the telN strain (Table 2).

TABLE 2

Improved transformation efficiency of the linear vector in a host strain containing telN.

| | pNZKA plus *Pneumocystis* DNA | pNZKA plus *Oxytricha* DNA |
|---|---|---|
| E. CLONI 10G-ptelN | 800 | 2400 |
| DH10B31sop | 62 | 200 |

In separate experiments, the two host strains were shown to have similar transformation efficiency when electroporated with pUC19 DNA, indicating the ability to take up DNA was similar for the two strains. The linear vector was maintained in both strains of cells after several rounds of freezing, dilution, and re-growth, indicating that the linear plasmid was stably maintained in both strains.

Example 11

Construction and Use of a Single-Antibiotic-Resistant Linear Vector

*Piromyces* sp. E2 is a fungus of the phylum Chytridiomycota. The genomic DNA from this microbe is approximately 85% AT, and cloning fragments even as small as 2 kb is very difficult in standard circular vectors. In contrast, fragments of this genome as large as 2-6 kb could be successfully cloned in the NZOC vector.

Figure 8:
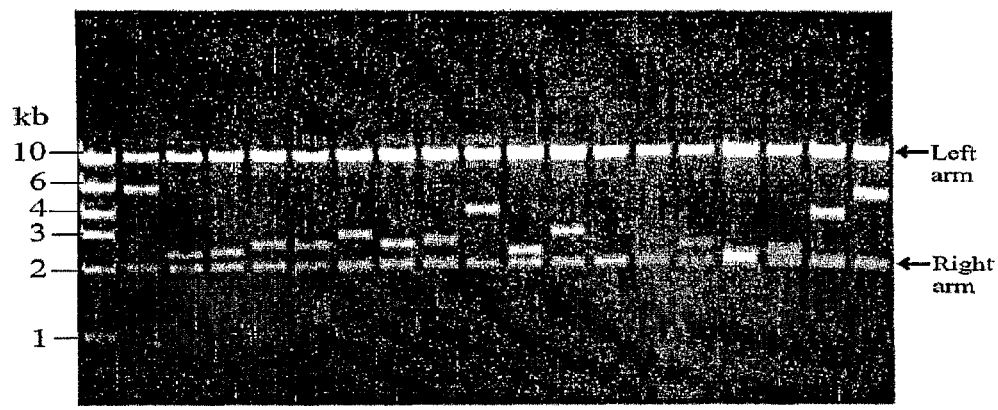
FIG. 8 is a photograph of an electrophoretic gel used to resolve NotI digests of *Piromyces* sp. E2 genomic DNA clones produced in pNZOC and selected on chloramphenicol plates.

Ten micrograms of *Piromyces* DNA was physically sheared to 2-6 kb using a HydroShear Device (Gene Machines), and the ends were repaired using the DNATERMINATOR® kit (Lucigen, Middleton, Wis.). The DNA was quantitated against a DNA mass standard using gel densitometry software (Alpha Innotech, San Leandro, Calif.), and ligated to a blunt digest of the pJAZZ® OC vector. The ligation reaction contained approximately 100 ng of insert DNA, 50 ng of digested pJAZZ® OC, ligase buffer, and 2 U T4 DNA ligase. The reaction was incubated at room temperature for 2 hours, heat treated for 15 minutes at 70 .degree. C., and used to transform electrocompetent E. CLONI® BIGEASY™ TSA cells. Cells were spread on to an agar plate containing 12.5 ug/ml chloramphenicol, XGAL, and IPTG. Linear plasmid DNA was isolated using standard alkaline lysis purification with binding to diatomaceous earth. The DNA was digested with Not I and assayed by agarose gel electrophoresis. As shown in FIG. 8, nearly all of the recombinant clones contained inserts of 2-6 kb. Twelve samples were sequenced to confirm that they contained genomic DNA from *Piromyces*. The AT content of some of these clones approached 96%; obtaining clones with this level of AT content has not been reported previously.

Example 12

Dual-Insert Cloning in a Linear Vector

The present Example describes construction of a dual-insert library in a linear vector. The insert DNAs were defined fragments of 10 kb amplified from *E. coli* genomic DNA by PCR using the Phusion polymerase (New England Biolabs) according to the manufacturer's recommendations. The primers used for PCR amplification were:

```
Primer 1:
                                       (SEQ ID NO: 33)
TTCTTATGGCCAGGGAGGCCGCTCTGGGTATAAGCGTAAGG Primer 2:
                                       SEQ ID NO: 34)
AACTAGTGGCCAGGGAGGCCATCAGCCAGGCGACGAATCAG Primer 3:
                                       (SEQ ID NO: 35)
GGACTTGGGCCACCCAGGCCTTGTAAATGCAGTATGGATTG Primer 4:
                                       (SEQ ID NO: 36)
ATCCTAGGGCCACCCAGGCCAGATATTGGAGAGTTGGACCAG
```

One PCR product, termed "EC39" was amplified using Primers 1 and 2; a second product, "EC40," was amplified using Primers 3 and 4. The primers also contain the recognition site for the restriction enzyme SfiI (underlined above), which after digestion leaves a 3 base pair overhang on the 3' strand of the double-stranded DNA amplification product.

EC39 was digested with SfiI to produce a 3' extension of -CCC; digestion of EC40 by SfiI created a 3' extension of -GGG. The digested products of the EC39 insert are therefore not able to ligate to themselves to form concatamers. Similarly, the digested EC40 products cannot self-ligate. Consistent with the scarcity of SfiI sites in most genomes, the regions chosen for amplification do not have internal SfiI sites. The 10 kb SfiI digestion products were purified and quantitated.

Vector pNZ-Sfi (SEQ ID NO:37) was derived from pNZKA by replacing the multiple cloning sites and the lacZ stuffer of pNZKA with a DNA fragment containing the lacZ stuffer flanked by different multiple cloning sites, including sites for the restriction enzyme SfiI. The new lacZ stuffer was generated by PCR amplification of the lacZ region of the vector NZAhd using the primers lacFSfi (SEQ ID NO:38) and lacRSfi (SEQ ID NO:39). The primers were phosphorylated with T4 polynucleotide kinase prior to performing the PCR. The resulting PCR product was purified and ligated to a SmaI digest of the vector NZAhd.

The ligation reaction was transformed into E. cloni GTS-8 cells, and transformants were selected on agar plates containing ampicillin, kanamycin, XGAL, and IPTG. The correct pNZ-Sfi clone was confirmed by sequencing.

The SfiI sites of the vector were designed such that digestion with SfiI creates a 10-kb left arm with a 3' extension of -GGG, a 2-kb right arm with a 3' extension of -CCC, and a 0.5 kb lacZ stuffer fragment. The -GGG extension on the left arm is compatible with the -CCC extension created by SfiI digestion of EC39; similarly, the right arm is compatible with the SfiI digest of EC40. The 5' phosphates were removed from the vector SfiI fragments by treatment with Calf Intestinal Phosphatase to prevent re-ligation of the vector arms. The digested vector fragments were fractionated on an agarose gel, and the bands were individually excised, purified, and quantitated.

Figure 9:
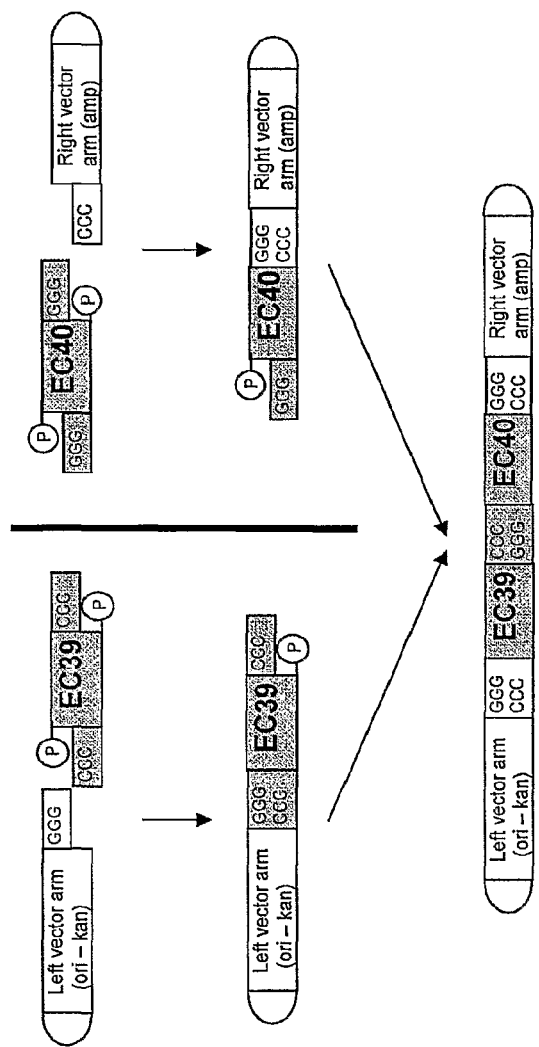
FIG. 9 is a schematic diagram showing the process of dual insert cloning using a linear vector of the invention (pNZSfi). Vector and insert fragments are not drawn to scale.

Dual insert cloning was performed as diagrammed in FIG. 9. The SfiI-digested left arm was ligated to an equimolar amount of SfiI-digested EC39. In a separate ligation reaction, the SfiI-digested right arm was ligated to an equimolar amount of SfiI-digested EC40. After allowing the ligation reactions to proceed to at least 50% completion, aliquots of the two ligation reactions were combined with each other. Further incubation was carried out to facilitate ligation of the left arm/EC39 molecules to the EC40/right arm molecules. The final ligation reaction was heat-inactivated, and the products were transformed into GTS 8 cells (Lucigen, Middleton, Wis.). An additional ligation reaction was performed with only the Sfi-I-digested left and right vector arms to measure the frequency of self-ligation.

One-tenth of the transformants were plated on media containing kanamycin and ampicillin to select for both arms of the linear vector. The plates also contained XGAL plus IPTG to screen against uncut vector or recombinants containing the lacZ stuffer fragment. The dual-insert ligation/transformation reaction produced ~2200 white colonies and 26 blue colonies. The self-ligation/transformation yielded 208 white colonies and 23 blue colonies.

Figure 10:
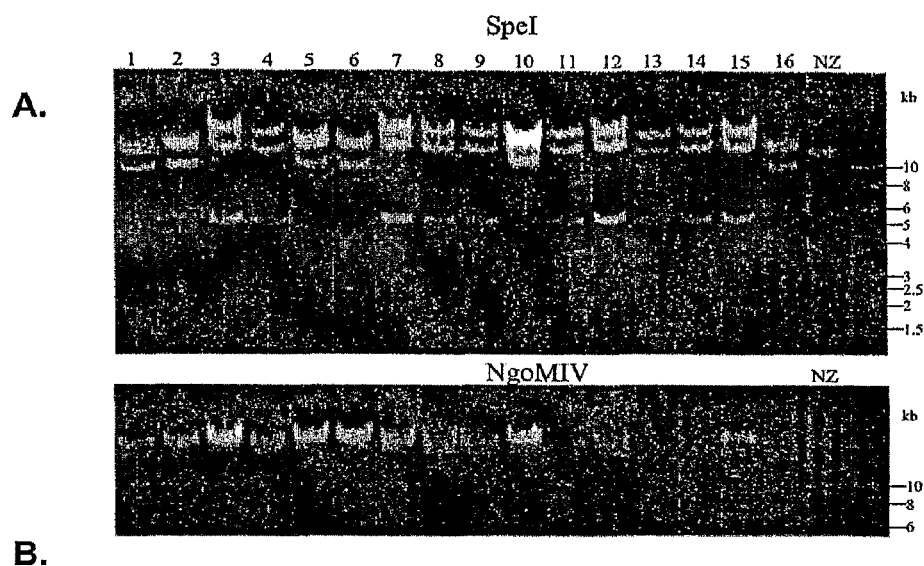
FIG. 10 shows (A) a photograph of an electrophoretic gel used to resolve restriction digests of NZSfi dual-insert recombinants and (B) a schematic diagram showing expected restriction fragments.
Figure 10:
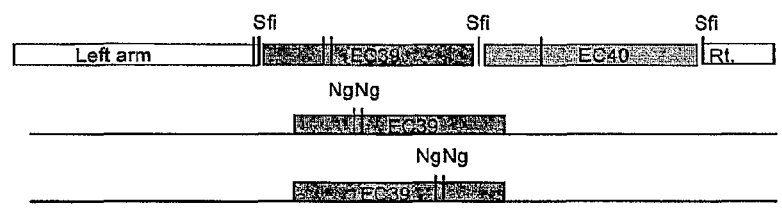
Figure 10:
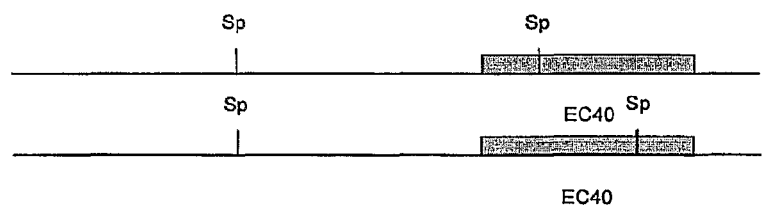

Thirty white colonies were randomly selected from the dual-insert plate, and grown overnight in TB media containing kanamycin plus arabinose Plasmid DNA was isolated by standard alkaline lysis methods, and restriction-digested with SpeI, NgoMIV, or NotI. SpeI has a single recognition site near the cloning site of the left arm and one site within the EC40 fragment. NgoMIV has a single site within the EC39 fragment, but no sites in the vector or in EC40. NotI has a site near each of the cloning sites, and no sites within EC39 or EC40; it therefore excises the entire dual insert. In all thirty clones analyzed, restriction analysis with these enzymes confirmed the presence of exactly one copy of each fragment and each vector arm in the expected relative positions of Left arm-EC39-EC40-Right arm, as shown in FIG. 10.

Example 13

Derivation of a Linear Vector from Phage PRD1

Genomic DNA from phage PRD1 is digested with BsrBI to remove the left telomere and its associated terminal protein from the genomic DNA. The 3-kb BsrBI fragment is isolated by agarose gel electrophoresis. Another aliquot of phage genomic DNA is digested with Xmni to remove the right telomere and its associated protein. The 1-kb XmnI fragment is isolated by agarose gel electrophoresis. PCR is used to amplify a DNA fragment containing a selectable marker and, optionally, a visual screening marker. Creation of such a fragment, containing the TAmpT and TerZ segments, is described in Example 2.

The DNA polymerase of phage PRD1 (GenBank ACCESSION NC 001421) is amplified by PCR with the primers PRD1 POL-F (SEQ ID NO:40) and PRD POL R (SEQ ID NO:41). The 1.7 kb PCR product is purified, digested with SphI, and cloned into a bacterial expression vector (e.g., pET24, Novagen).

The PRD POL expression vector is transformed into E. CLONI cells, and a clone expressing the PRD1 polymerase gene is confirmed by sequence analysis. Expression of the PRD1 polymerase is verified by presence of an additional band at approximately 65 kD on an acrylamide gel.

Alternatively, the PRD1 polymerase gene is appended to a promoter sequence and integrated into the genome of E. CLONI cells, using e.g. methods described for integration of the telN gene in Example 1.

The PRD1 expression clone is made competent by standard techniques. A ligation reaction containing the 1-kb BsrBI fragment, the TAmpT-TerZ fragment, and the 3-kb XmnI fragment is transformed into the competent PRD1 expression cells. Colonies that express blue color and are ampicillin resistant are selected for further growth. The presence of the PRD-AmpLacZ vector is confirmed by restriction analysis and sequencing of plasmid DNA.

The invention claimed is:

1. A linear cloning vector comprising:
a left arm comprising a left telomere and a first selectable marker, wherein the left telomere comprises a covalently closed end comprising a protelomerase target site;
a right arm comprising a right telomere and a second selectable marker, wherein the right telomere comprises a covalently closed end comprising a protelomerase target site;
a cloning region located between the left arm and the right arm; and
an origin of replication.

2. The vector of claim 1, further comprising a pair of transcriptional terminator regions flanking the cloning region, wherein the transcriptional terminator regions are the same or different and are unidirectional or bidirectional.

3. The vector of claim 2, further comprising a transcriptional terminator region after the second selectable marker, wherein one of the pair of transcriptional terminator regions flanking the cloning region and the transcriptional terminator region after the second selectable marker together flank the second selectable marker.

4. The vector of claim 1, wherein the cloning region comprises one or more restriction sites, wherein each of the one or more restriction sites is unique.

5. The vector of claim 1, wherein the cloning region comprises a multiple cloning region, wherein the multiple cloning region comprises a plurality of restriction sites, wherein each of the plurality of restriction sites in the multiple cloning region is unique.

6. The vector of claim 1, wherein the cloning region comprises a stuffer region.

7. The vector of claim 6, wherein the stuffer region comprises a reporter gene flanked by a pair of restriction sites which are the same or different.

8. The vector of claim 1, wherein the first and second selectable markers are antibiotic resistance markers or wherein the first or second selectable marker is the origin of replication.

9. The vector of claim 1, further comprising one or more genes outside the cloning region, the one or more genes being selected from the group consisting of a replication initiation protein gene and a prophage repressor gene.

10. The vector of claim 1, further comprising genes outside the cloning region, the genes comprising a replication initiation protein gene and a prophage repressor gene.

11. The vector of claim 10, wherein the cloning region comprises one or more restriction sites, wherein each of the one or more restriction sites is unique.

12. The vector of claim 1, wherein the first and second selectable markers are antibiotic resistance markers.

13. A host cell comprising:
a linear cloning vector comprising:
a left arm comprising a left telomere and a first selectable marker, wherein the left telomere comprises a covalently closed end comprising a protelomerase target site and wherein the first selectable marker is an origin of replication;

a right arm comprising a right telomere and a second selectable marker, wherein the right telomere comprises a covalently closed end comprising a protelomerase target site; and a cloning region located between the left arm and the right arm; and a polynucleotide sequence encoding a protelomerase, wherein the polynucleotide sequence encoding the protelomerase is integrated into the host cell genome.

14. A kit comprising:

a linear cloning vector comprising:

a left arm comprising a left telomere and a first selectable marker, wherein the left telomere comprises a covalently closed end comprising a protelomerase target site and wherein the first selectable marker is an origin of replication;

a right arm comprising a right telomere and a second selectable marker, wherein the right telomere comprises a covalently closed end comprising a protelomerase target site; and a cloning region located between the left arm and the right arm; and a recombinant host cell comprising a polynucleotide sequence encoding a protelomerase, wherein the polynucleotide sequence is integrated into the host cell genome.

15. A method of cloning a polynucleotide sequence having a first end and a second end using a linear cloning vector, the linear cloning vector comprising: a left arm comprising a left telomere and a first selectable marker, wherein the left telomere comprises a covalently closed end comprising a protelomerase target site and wherein the first selectable marker is an origin of replication; a right arm comprising a right telomere and a second selectable marker, wherein the right telomere comprises a covalently closed end comprising a protelomerase target site; and a cloning region located between the left arm and the right arm, the method comprising:

a) processing the linear cloning vector in the cloning region to separate the right arm from the left arm;

b) joining the first end of the polynucleotide sequence to the right arm and the second end of the polynucleotide sequence to the left arm to provide a joined product;

c) transforming a host cell with the joined product; and d) growing the transformed host cell on medium, such that selection is provided for the first and second selectable markers of the linear cloning vector.

16. The method of claim 15, wherein the host cell used in step c) is a recombinant host cell comprising a polynucleotide sequence encoding a protelomerase, wherein the polynucleotide sequence is integrated into the host cell genome.

17. The method of claim 15, wherein the cloning region comprises one or more restriction sites, wherein each of the one or more restriction sites is unique.

18. A linear cloning vector comprising:

a left arm comprising a left telomere and a first selectable marker, wherein the left telomere comprises a covalently closed end comprising a protelomerase target site and wherein the first selectable marker is an origin of replication;

a right arm comprising a right telomere and a second selectable marker, wherein the right telomere comprises a covalently closed end comprising a protelomerase target site; and a cloning region located between the left arm and the right arm, wherein the cloning region comprises one or more restriction sites, wherein each of the one or more restriction sites is unique.

19. A host cell comprising the vector of claim 18.

20. The host cell of claim 19, further comprising a polynucleotide sequence encoding a protelomerase integrated into the host cell genome.

21. The host cell of claim 19, further comprising a polynucleotide sequence encoding a partitioning protein, a polynucleotide sequence encoding an antirepressor, or combinations thereof.

22. The vector of claim 18, further comprising a pair of transcriptional terminator regions flanking the cloning region, wherein the transcriptional terminator regions are the same or different and are unidirectional or bidirectional.

23. The vector of claim 22, further comprising a transcriptional terminator region on a side of the second selectable marker distal from the cloning region, wherein one of the pair of transcriptional terminator regions flanking the cloning region and the transcriptional terminator region on the side of the second selectable marker distal from the cloning region together flank the second selectable marker.

24. The vector of claim 18, wherein the cloning region comprises a multiple cloning region, wherein the multiple cloning region comprises a plurality of restriction sites, wherein each of the plurality of restriction sites in the multiple cloning region is unique.

25. The vector of claim 18, wherein the cloning region comprises a stuffer region.

26. The vector of claim 25, wherein the stuffer region comprises a reporter gene flanked by a pair of restriction sites which are the same or different.

27. The vector of claim 18, wherein the second selectable marker is an antibiotic resistance marker.

28. The vector of claim 18, further comprising one or more genes outside the cloning region, the one or more genes being selected from the group consisting of a replication initiation protein gene and a prophage repressor gene.

29. The vector of claim 18, further comprising genes outside the cloning region, the genes comprising a replication initiation protein gene and a prophage repressor gene.

30. A method of cloning at least two distinct polynucleotides using a linear cloning vector, the linear cloning vector comprising: a left arm comprising a left telomere and a first selectable marker, wherein the left telomere comprises a covalently closed end comprising a protelomerase target site and wherein the first selectable marker is an origin of replication; a right arm comprising a right telomere and a second selectable marker, wherein the right telomere comprises a covalently closed end comprising a protelomerase target site; and a cloning region located between the left arm and the right arm, the method comprising:

a) processing each of the polynucleotides to provide a linking sequence on both termini of the polynucleotides;

b) processing the linear cloning vector in the cloning region to provide a linking sequence on a terminus opposite the telomere of each arm;

c) forming a joined product comprising the polynucleotides and the right and left arms, wherein the arms are noncontiguous with each other and are separated by the polynucleotides;

d) transforming a host cell with the joined product; and e) growing the transformed host cell on medium, such that selection is provided for the first and second selectable markers of the linear cloning vector, wherein multiplication of the host cell results in cloning of the polynucleotides.

31. A method of cloning a polynucleotide sequence using a linear cloning vector, the linear cloning vector comprising: a left arm comprising a left telomere and a first selectable marker, wherein the left telomere comprises a covalently closed end comprising a protelomerase target site and wherein the first selectable marker is an origin of replication; a right arm comprising a right telomere and a second selectable marker, wherein the right telomere comprises a covalently closed end comprising a protelomerase target site; and a cloning region located between the left arm and the right arm, the method comprising:
- a) inserting the polynucleotide sequence between the right arm and the left arm of the linear cloning vector to provide a joined product; and
- b) growing a host cell comprising the joined product, such that selection is provided for the first and second selectable markers of the linear cloning vector.

32. The method of claim 31, wherein the cloning region comprises one or more restriction sites, wherein each of the one or more restriction sites is unique.

* * * * *